United States Patent
Milne-Robertson et al.

(10) Patent No.: US 7,511,123 B2
(45) Date of Patent: Mar. 31, 2009

(54) IMMUNO-INTERACTIVE FRAGMENTS OF THE ALPHA-C SUBUNIT OF INHIBIN

(75) Inventors: David Mark Milne-Robertson, Glen Waverley (AU); Peter Gordon Stanton, Nunawading (AU); Nicholas Francis Cahir, Blackburn (AU)

(73) Assignee: Prince Henry's Institute of Medical Research, Clayton, Victoria (AU)

( * ) Notice: Subject to any disclaimer, the term of this patent is extended or adjusted under 35 U.S.C. 154(b) by 222 days.

(21) Appl. No.: 10/125,187

(22) Filed: Apr. 18, 2002

(65) Prior Publication Data

US 2003/0162229 A1    Aug. 28, 2003

Related U.S. Application Data

(63) Continuation of application No. PCT/AU00/01258, filed on Oct. 18, 2000.

(30) Foreign Application Priority Data

Oct. 18, 1999  (AU) .................................... PQ3485
Aug. 3, 2000   (AU) .................................... PQ9162

(51) Int. Cl.
G01N 33/574   (2006.01)
G01N 33/577   (2006.01)
C07K 16/26    (2006.01)
C12P 21/08    (2006.01)
G01N 33/543   (2006.01)
G01N 33/74    (2006.01)

(52) U.S. Cl. .............. 530/388.24; 435/7.94; 435/70.21; 435/330; 435/331; 435/336; 435/344; 435/975; 436/518; 436/547; 436/548; 436/64; 436/813; 530/387.3; 530/387.7; 530/387.9; 530/388.8; 530/828; 530/850

(58) Field of Classification Search ................ 435/7.94, 435/70.21, 452, 330, 331, 336, 344; 436/518, 436/547, 548, 64, 813; 530/387.3, 387.7, 530/387.9, 388.24, 388.8, 828, 850
See application file for complete search history.

(56) References Cited

U.S. PATENT DOCUMENTS 4,737,578 A    4/1988    Evans et al.

FOREIGN PATENT DOCUMENTS

WO    WO 95/32431    11/1995
WO    WO 99/57289    11/1999

OTHER PUBLICATIONS

Saito et al., 1989. Synthetic Peptide segments of inhibin alpha- and beta-subunits: preparation and characterization of polyclonal antibodies. Endocrinology 125: 898-905.*

Groome, 1991. Ultrasensitive two-site assays for inhibin-A and activin-A using monoclonal antibodies raised to synthetic peptides. J. Immunological Meth. 145: 65-69.*
Campbell, 1991. Monoclonal Antibody and Immunosensor Technology. Elsevier, Amsterdam, pp. 3-6, 45.*
Robertson et al., May 1999. Combined inhibin and CA125 assays in the detection of ovarian cancer. Clinical Chemistry 45: 651-658.*
Kelly E. Mayo et al., "Inhibin A-subunit cDNAs from porcine ovary and human plancenta," *Proc. Natl. Acad. Sci. USA*, 83:5849-5853 (Aug. 1986).
Anthony J. Mason et al., "Structure of Two Human Ovarian Inhibins," *Biochemical and Biophysical Research Communications*, 135(3):957-964 (Mar. 28, 1986).
D. Robertson et al., "Biological and Immunological Characterization of Inhibin Forms in Human Plasma," *Journal of Clinical Endocrinology and Metabolism*, 81(2):669-676 (1996).
Richard E. Lappöhn, M.D., et al., "Inhibin as a Marker for Granulosa-Cell Tumors," *The New England Journal of Meicine*, 321(12):790-793 (Sep. 21, 1989).
Nigel Groome et al., "Immunoassays for inhibin and its subunits—Further applications of the synthetic peptide approach," *Journal of Immunological Methods*, 165:167-176 (1993); and.
N.P. Groome et al., "Detection of dimeric inhibin throughout the human menstrual cycle by two-site enzyme immunoassay," *Clinical Endocrinology*, 40:717-723 (1994).
Groome, N., et al., "Immunoassays for Inhibin and Its Subunits Further Applications of the Synthetic Peptide Approach," *Journal of Immunological Methods*, Elsevier Science Publishers B.V., Amsterdam, NL, 165(2):167-176 (1993)—XP000564557—ISSN: 0022-1759, Abstract, p. 171, col. 2, last paragraph.
Sewani, C.R., et al., "Display of an Inhibin Epitope in a Surface-Exposed Loop of the *E. coli* Heat-Labile Enterotoxin B Subunit," *Vaccine*, Butterworth Scientific Guildford, GB, 16(17):1611-1619 (Oct. 1, 1998)—XP00413699—ISSN: 0264-410X, p. 1161.
Sheng, W., et al., "Synthesis of a Fragment of Human Inhibin.alpha.-Subunit and Preparation of Its Antibody," Abstract retrieved from Online Database of Chemical Abstracts Service, Columbus, OH, STN Database accession No. 120:96001 CA—XP002268782 and Shengzhi Yu Biyun (1993), 13(2), 90-4 (1993).
Saito, S., et al., "Synthetic Peptide Segments of Inhibin alpha- and beta-Subunits: Preparation and Characterization of Polyclonal Antibodies," Abstract retrieved from Medline Database, U.S. National Library of Medicine (NLM), Bethesda, MD, Database accession No. NLM2752983—XP002268783 and *Endocrinology*, United States, 125(2):898-905 (Aug. 1989)—ISSN: 0013-7227.

(Continued)

*Primary Examiner*—Mark L Shibuya
*Assistant Examiner*—James L Grun
(74) *Attorney, Agent, or Firm*—Panitch Schwarze Belisario & Nadel LLP

(57) ABSTRACT

Novels immuno-interactive fragments of the (alpha)C portion of a mammalian inhibin alpha subunit are disclosed, together with their variants and derivatives for producing antigen-binding molecules that are interactive with said (alpha)C portion, which are chemically well defined and which can be produced in commercially significant quantities. The antigen-binding molecules of the invention can be used for the detection of a mammalian inhibin and for the treatment and/or prevention of conditions associated with aberrant levels of a mammalian inhibin.

12 Claims, 19 Drawing Sheets

OTHER PUBLICATIONS

Mason, Anthony J., et al., "Characterization and Determination of the Biological Activities of Noncleavable High Molecular Weight Forms of Inhibin A and Activin A," *Molecular Endocrinology*, 10(9):1055-1065 (1996)—XP002268781—ISSN: 0888-8809, p. 1063, col. 2, last paragraph.

Stenman, U-H, et al., "Markers Supplementing CA 125 in Ovarian Cancer," *Annals of Medicine*, Finnish Medical Society Duodecim, Helsinki, FI, 27(1):115-120 (1995—XP009007535—ISSN: 0785-3890.

Matzuk, M. M., et al., "Alpha-Inhibin is a Tumour-Suppressor Gene with Gonadal Specificity in Mice," *Nature*, Macmillan Journals Ltd., London, GB, 360(6402):313-319 (Nov. 26, 1992)—XP001145972—ISSN: 0028-0836.

Mellor, S. L., et al., "Loss of the Expression and Localization of Inhibin Alpha-Subunit in High Grade Prostate Cancer," *Journal of Clinical Endocrinology and Metabolism*, New York, NY, 83(3)969-975 (Mar. 1998)—XP001145982—ISSN: 0021-972X.

Schlunegger, Michael P., et al., "An Unusual Feature Revealed by the Crystal Structure at 2.2 ÅResolution of Human Transforming Growth Factor-$\beta 2$," *Nature*, 358:430-434 (Jul. 30, 1992)—XP002110204.

Morris, D.G., et al., "Effect of Immunization Against Synthetic Peptide Sequences of Bovine Inhibin $\alpha$-Subunit on Ovulation Rate and Twin-Calving Rate in Heifers," *Journal of Reproduction and Fertility*, 97:255-261 (1993)—XP009033087.

\* cited by examiner

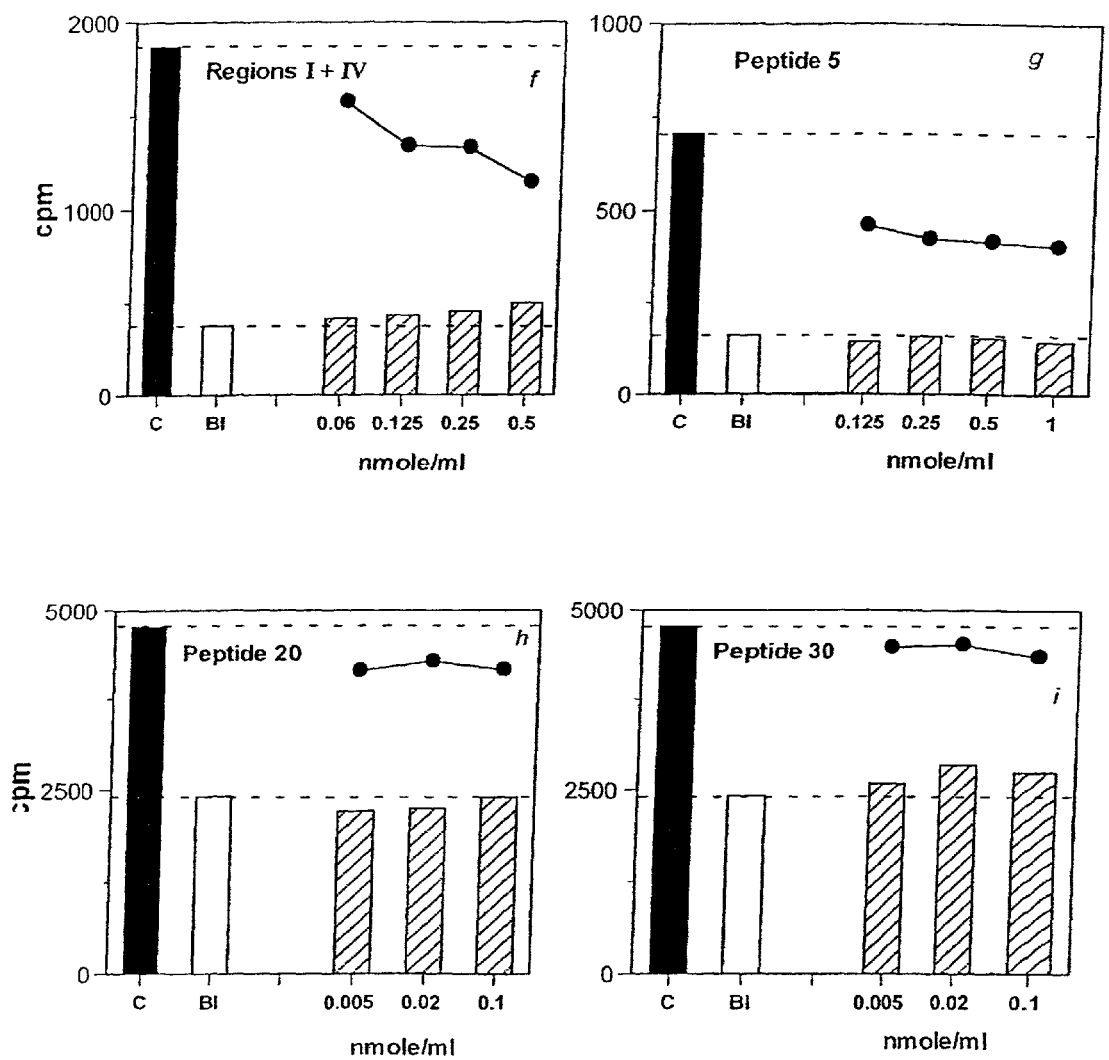
FIGURE 3 (cont..)

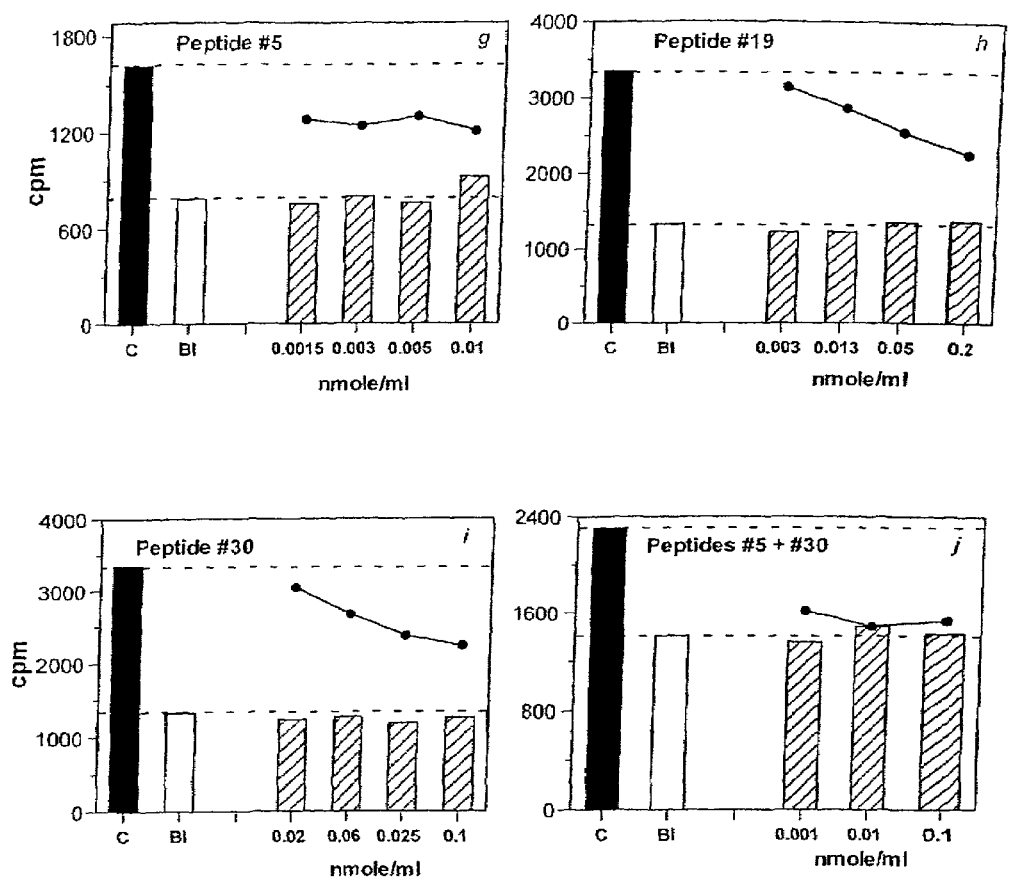
FIGURE 4 (cont..)

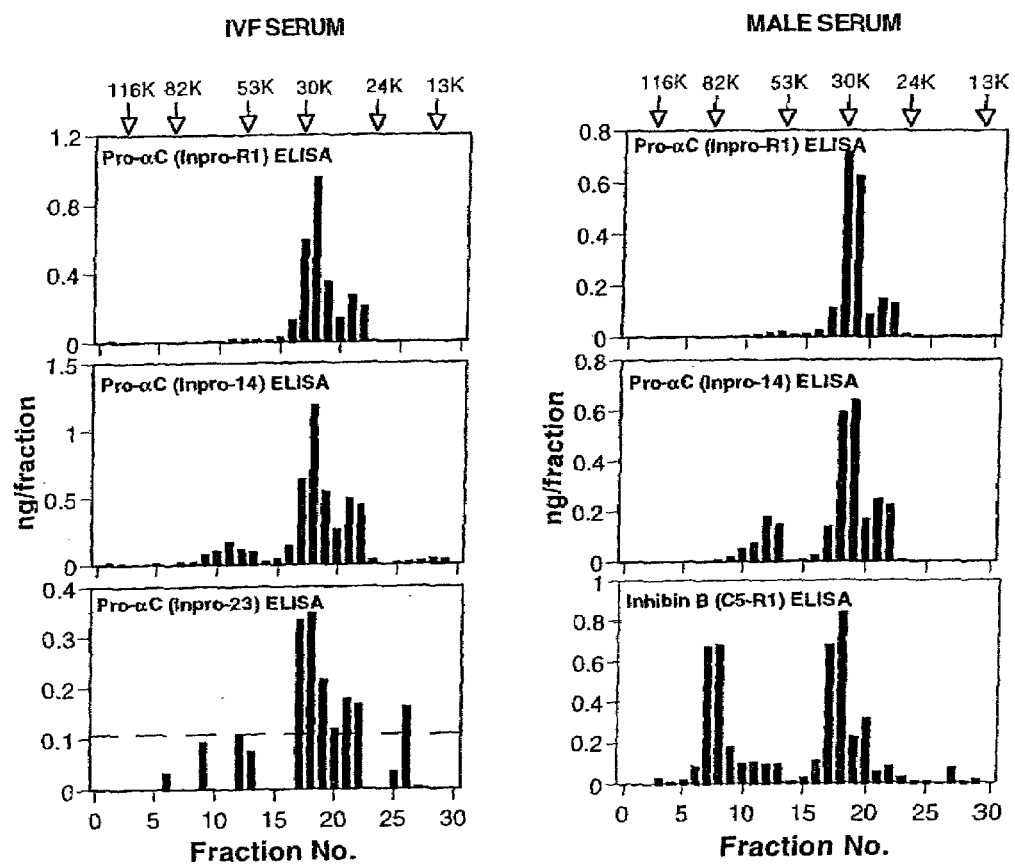
FIGURE 11 (cont..)

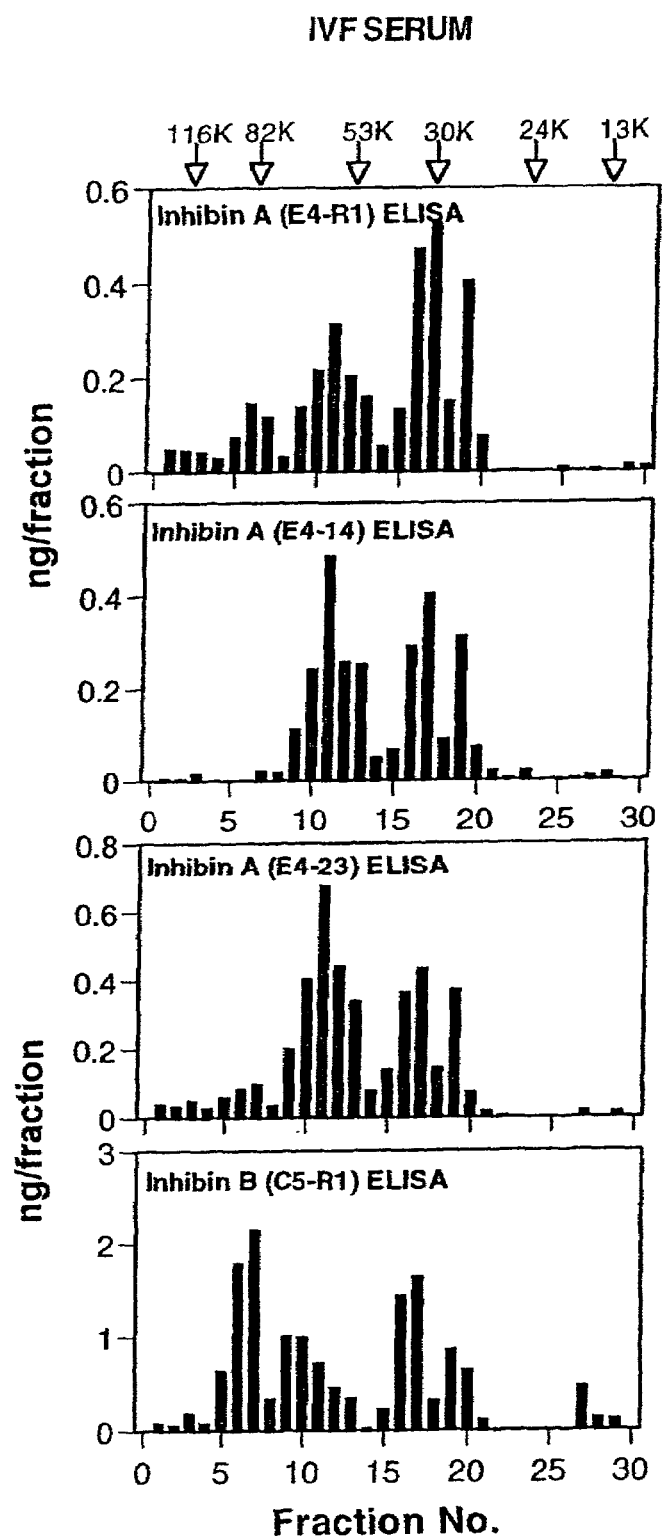
FIGURE 11 (cont..)

IMMUNO-INTERACTIVE FRAGMENTS OF THE ALPHA-C SUBUNIT OF INHIBIN

CROSS-REFERENCE TO RELATED APPLICATIONS

This application is a continuation of International Application No. PCT/AU00/01258, filed Oct. 18, 2000, which was published in the English language on Apr. 26, 2001, under International Publication No. WO 01/29079, and the disclosure of which is incorporated herein by reference.

BACKGROUND OF THE INVENTION

The present invention relates generally to novel antigens for developing antigen-binding molecules that are interactive with mammalian inhibins. More particularly, the present invention relates to immuno-interactive fragments of the (alpha)C portion of a mammalian inhibin alpha subunit and to variants and derivatives of these immuno-interactive fragments for producing novel antigen-binding molecules that recognize the said (alpha)C portion. The invention is also concerned with the use of these antigen-binding molecules for detecting a mammalian inhibin and for treating or preventing conditions associated with aberrant levels of a mammalian inhibin.

Inhibin is a dimeric glycoprotein produced by diverse tissues including the gonads, pituitary, brain, bone marrow, placenta, and adrenal gland. It was initially identified by its ability to inhibit the secretion of follicle stimulating hormone (FSH) by the pituitary (for reviews, see Vale et al., 1990, The inhibin/activin family of hormone and growth factors. In Peptide growth factors and their receptors: Handbook of Experimental Physiology 95:211-248 (Eds. Spom and Roberts) Springer-Verlag, Berlin; Burger, 1992, Reproductive Medicine Review 1:1-20; Baird & Smith, 1993, Oxford Rev. Reprod. Biol. 15:191-232). However, it was also found subsequently to be secreted by mucinous and granulosa cell cancers of the ovary. Thus, measurement of serum inhibin in women, particularly postmenopausal women, provides a good diagnostic test for detecting these cancers (Lapphorn et al., 1989, New England 0.1 Med. 321:790-793; Healy et al., 1993, N. Eng. J. Med. 329:1539-420) and for monitoring their recurrence after surgery. The mucinous and granulosa cell cancers represent 20-30% of all ovarian cancers. Serum inhibin is less effective as a marker of serous cancer, which is the major (40%) ovarian cancer. In contrast, a widely used cancer marker, CA125, is effective in the detection of serous cancers and less so with the mucinous and granulosa cell cancers.

Inhibin consists of two chains, the alpha subunit (made up of 3 regions, Pro, (alpha)N and (alpha)C) and either the (beta)A subunit (inhibin A) or (beta)B subunit (inhibin B), of varying molecular weight. Various inhibin assays with specificities directed towards different regions of the inhibin molecule have been developed for diagnosis of ovarian cancer.

Initial studies by Lapphorn et al. (1989, supra) and Healy et al. (1993, supra) suggested that measurement of serum inhibin by radioimmunoassay (RIA) which detects (alpha)C inhibin forms may be of diagnostic value in monitoring mucinous and granuloma cell tumours. Whilst this method is reliable, it is less sensitive and practical in comparison to two-site or sandwich antibody assays using, for example, colorimetric or fluorescent labels for detection.

A two-site immunofluorometric assay ((alpha)C IFMA) for the (alpha)C portion of the alpha subunit of inhibin has been developed by Robertson et al. (1996, J. Clin. Endocrinol. Metab. 81:669-676). This assay, which utilizes sheep polyclonal antisera and the fluorescent label Europium (Eu), detects all known inhibin alpha subunit-containing proteins. Compared to other inhibin assays specific for the alpha subunit or the (alpha)(beta) dimers (inhibin A and B), the (alpha)C IFMA and the (alpha)C RIA have been shown to be more effective in detecting different ovarian cancers (Robertson et al., 1999, Clin. Endocrinol. 50:381-387; ibid, Clin. Chemistry 45:651-658).

Robertson et al. (1999, Clin. Chemistry 45:651-658) have also shown that 89-90% of all ovarian cancers can be detected by the (alpha)C IFMA in combination with an immunoassay for the ovarian cancer marker CA125. This combined detection value was considerably higher than for each assay alone or a combination of CA125 with other inhibin assays, and is clinically useful in the diagnosis of the majority of ovarian cancers. Furthermore, in view of its increased sensitivity, the (alpha)C IFMA is able to detect the increase in serum inhibin associated with a recurrence of granulosa cell tumours at an earlier time following surgery. The earlier detection of the cancer is desirable for successful treatment.

Despite the clinical utility of the (alpha)C IFMA, the use of polyclonal antisera in this immunoassay or other types of multi-site assays in the diagnostic market is a disadvantage owing to the inherent limited supply of polyclonal antisera and the difficulties of quality control including specificity between antiserum batches. It would therefore be beneficial to utilize monoclonal antisera or other antigen-binding molecules where the stocks are potentially limitless and the quality can be more easily monitored.

BRIEF SUMMARY OF THE INVENTION

The present invention is predicated in part on the determination of various immuno-interactive fragments of the (alpha)C portion of an inhibin alpha subunit, which fragments interact with polyclonal antisera raised against the (alpha)C portion. These fragments have utility in producing antigen-binding molecules that are interactive with said (alpha)C portion, that are chemically well defined and that can be produced in commercially significant quantities. The antigen-binding molecules so produced can be used for the detection of a mammalian inhibin and for the treatment and/or prevention of conditions associated with aberrant levels of a mammalian inhibin.

Accordingly, in one aspect of the invention, there is provided an immuno-interactive fragment of the (alpha)C portion of a mammalian inhibin alpha subunit, or variant or derivative of said fragment, wherein said fragment is interactive with a polyclonal antibody raised against said (alpha)C portion.

Preferably, the polyclonal antibody is an ovine polyclonal antibody. In a preferred embodiment, the ovine polyclonal antibody is selected from the group consisting of As #41, As #128 (Robertson et al., 1996, supra) and As #1989 (Lapphorn et al., 1989, supra).

Suitably, the mammalian inhibin alpha subunit is a human inhibin alpha subunit.

The (alpha)C portion preferably comprises the sequence set forth in SEQ ID NO: 2.

Suitably, said immuno-interactive fragment comprises a sequence selected from any one or more of SEQ ID NOs: 3, 4, 5, 6, 18, 19, 20, 21, 22, 23, 30, 31, 32, 35, 36, 37, 38, 39, 40, 55, 56, 57, 58, 59, 60, 68, 69, 70, 71, 72 and 73.

In one embodiment, said immuno-interactive fragment preferably comprises a sequence selected from any one or more of SEQ ID NOs: 5, 35, 36, 37, 38, 39 and 40.

In another embodiment, said immuno-interactive fragment preferably comprises a sequence selected from any one or more of SEQ ID NOs: 18, 19, 20, 21, 22, 23, 31, 32, 55, 56, 57, 58, 59 and 60.

In yet another embodiment, said immuno-interactive fragment preferably comprises a sequence selected from any one or more of SEQ ID NOs: 68, 69, 70, 71, 72 and 73.

In another aspect, the invention contemplates a method of producing a variant of an immuno-interactive fragment as broadly described above, including the steps of:

(a) combining a compound suspected of being said variant with at least one antigen-binding molecule that binds to said immuno-interactive fragment; and (b) detecting the presence of a conjugate comprising said compound and said antigen-binding molecule, which indicates that said compound is a said variant.

In yet another aspect, the invention resides in an antigen-binding molecule that binds specifically to an immuno-interactive fragment of inhibin (alpha)C as broadly described above or variant or derivative thereof, with the proviso that said antigen-binding molecule is other than a member selected from the group consisting of a polyclonal antibody and the R1 monoclonal antibody described by Groome et al (1993, J. Immunol. Meth. 165:167-176; 1994, Clin. Endocrinol. 40:717-723).

In a further aspect, the invention provides a method of producing an antigen-binding molecule that binds specifically to an immuno-interactive fragment of inhibin (alpha)C as broadly described above or variant or derivative thereof, comprising:

(a) producing an antigen-binding molecule against inhibin (alpha)C or fragment thereof;

(b) combining the antigen-binding molecule with said immuno-interactive fragment, variant or derivative; and (c) detecting the presence of a conjugate comprising said antigen-binding molecule and said fragment.

In yet another aspect, the invention resides in the use of an immuno-interactive fragment, variant or derivative according to the present invention to produce an antigen-binding molecule that binds specifically to the (alpha)C portion of a mammalian inhibin alpha subunit and preferably to a region of said (alpha)C portion corresponding to said immuno-interactive fragment.

In yet another aspect, the invention provides antigen-binding molecules so produced, with the proviso that said antigen-binding molecule is other than a member selected from the group consisting of a polyclonal antibody and the R1 monoclonal antibody described by Groome et al (1993, J. Immunol. Meth. 165:167-176; 1994, Clin. Endocrinol. 40:717-723).

In another aspect, the invention provides a composition for use in eliciting an immune response in a mammal which response includes production of elements that specifically bind the (alpha)C portion of a mammalian inhibin alpha subunit, said composition comprising an immuno-interactive fragment, variant or derivative as broadly described above, together with a pharmaceutically acceptable carrier.

Optionally, said composition further comprises an adjuvant.

In yet another aspect of the invention there is provided a method for eliciting an immune response in a mammal which response includes production of elements that specifically bind the (alpha)C portion of a mammalian inhibin alpha subunit, comprising administering to said mammal an immunogenically effective amount of a composition as broadly described above.

In another aspect, the invention provides an isolated polynucleotide encoding an immuno-interactive fragment, variant or derivative as broadly described above.

In yet another aspect, the invention features an expression vector comprising a polynucleotide as broadly described above wherein the polynucleotide is operably linked to a regulatory polynucleotide.

In a further aspect, the invention provides a host cell containing a said expression vector.

According to another aspect of the invention, there is provided a method of detecting a mammalian inhibin in a biological sample suspected of containing it, comprising:

(a) contacting the biological sample with an antigen-binding molecule as broadly described above; and (b) detecting the presence of a complex comprising the said antigen-binding molecule and the mammalian inhibin in said contacted sample.

In another aspect of the invention, there is provided a method of diagnosing a condition associated with an aberrant concentration of a mammalian inhibin in a biological sample of a patient, comprising:

(a) contacting the biological sample with an antigen-binding molecule as broadly described above;

(b) measuring the concentration of a complex comprising the said antigen-binding molecule and the mammalian inhibin in said contacted sample; and (c) relating said measured complex concentration to the concentration of mammalian inhibin in said sample, wherein the presence of said aberrant concentration is indicative of said condition.

Suitably, the condition is a cancer. Preferably, the cancer is of a tissue selected from the group consisting of ovary, uterus, breast, pituitary, testis and prostate. In a preferred embodiment, the cancer is ovarian cancer.

In yet another aspect, the invention contemplates a method of diagnosing a condition associated with an aberrant concentration of a mammalian inhibin and an aberrant concentration of another antigen in a biological sample of a patient, comprising:

(a) contacting a biological sample of the patient with a first antigen-binding molecule that binds specifically to the (alpha)C portion of a mammalian inhibin alpha subunit as broadly described above;

(b) contacting said biological sample or another biological sample obtained from said patient with a second antigen-binding molecule that is immuno-interactive with said other antigen;

(c) measuring the concentration of a first complex comprising the first antigen-binding molecule and the mammalian inhibin in said contacted sample;

(d) measuring the concentration of a second complex comprising the second antigen-binding molecule and the other antigen in said contacted sample; and (e) relating said measured complex concentrations to the concentration of mammalian inhibin and the concentration of the other antigen in said sample, wherein the presence of said aberrant concentrations is indicative of said condition.

In a preferred embodiment, the condition is ovarian cancer and the other antigen is an ovarian cancer marker. In this instance, the ovarian cancer marker is preferably CA125.

In yet another aspect of the invention, there is provided a method for treating or preventing a condition associated with an aberrant concentration of a mammalian inhibin in a mammal, comprising administering to said mammal a therapeutically effective amount of a composition as broadly described above.

The invention also extends to the use of the immunointeractive fragment, variant or derivative according to the present invention or the use of the antigen-binding molecule mentioned above in a kit for detecting and/or measuring mammalian inhibin in a biological sample.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings.

DETAILED DESCRIPTION OF THE INVENTION

1. Definitions

Figure 1:
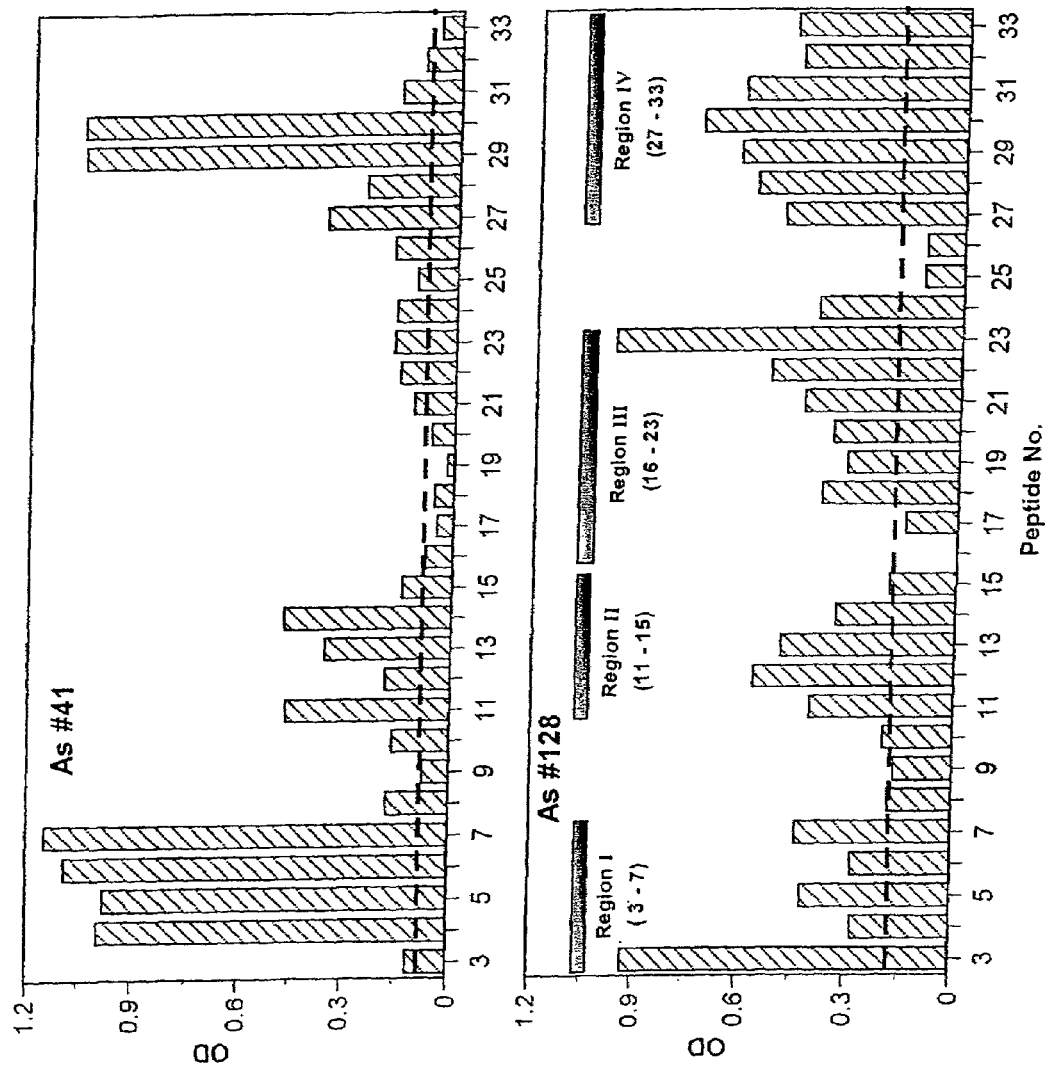
FIG. 1 depicts a pair of histograms showing the binding of antiserum (As) #41 and #128 to each of the 31 biotinylated peptides immobilized to streptavidin-coated surface. The binding was assessed by binding of an enzyme-linked anti-IgG antibody. Dashed lines refer to the assay sensitivity. See text for further details. Based on these and other studies, 4 pools were formed as shown (Regions I, II, III, IV) and used in further analysis with Assays 2 and 3.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

"Amplification product" refers to a nucleic acid product generated by nucleic acid amplification techniques.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

The term "biological sample" as used herein refers to a sample that may be extracted, untreated, treated, diluted or concentrated from a patient. The biological sample may be selected from the group consisting of whole blood, serum, plasma, saliva, urine, sweat, ascitic fluid, peritoneal fluid, synovial fluid, amniotic fluid, cerebrospinal fluid, skin biopsy, and the like. The biological sample preferably includes serum, whole blood, plasma, lymph and ovarian follicular fluid as well as other circulatory fluid and saliva, mucus secretion and respiratory fluid. More preferably, the biological sample is a circulatory fluid such as serum or whole blood or a fractionated portion thereof. Most preferably, the biological sample is serum or a fractionated portion thereof.

By "condition associated with an aberrant concentration" is meant any condition including a healthy condition or an unhealthy condition that is associated with a concentration of the (alpha)C portion of a mammalian inhibin alpha subunit which concentration deviates significantly from a corresponding normal concentration range. Suitably, the condition is a cancer including ovarian, prostate, testicular, pituitary, breast and uterine cancer.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions, or deletions that provide for functional equivalent molecules. Accordingly, the term derivative encompasses molecules that will elicit an immune response against the (alpha)C portion of a mammalian inhibin alpha subunit.

For the purposes of the present invention, the phrase "elicit(s) an immune response" refers to the ability of the aforementioned immuno-interactive fragment or variant to produce an immune response in a mammal to which it is administered, wherein the response includes the production of elements which specifically bind the (alpha)C portion of a mammalian inhibin alpha subunit.

"Homology" refers to the percentage number of amino acids that are identical or constitute conservative substitutions as defined in Table A below. Homology may be determined using sequence comparison programs such as GAP (Deveraux et al., 1984, Nucl. Acids Res. 12:387-395). In this way, sequences of a similar or substantially different length to those cited herein might be compared by insertion of gaps into the alignment, such gaps being determined, for example, by the comparison algorithm used by GAP.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

By "immunologically effective amount" is meant the administration to a mammal of an amount of an immuno-interactive fragment, variant or derivative of the invention, either in a single dose or as part of a series, that is effective for raising an immune response against the (alpha)C portion of a mammalian inhibin alpha subunit. The effective amount will vary depending upon the taxonomic group of mammal to be treated, the capacity of the individual's immune system to elicit an immune response (inclusive of a humoral and/or a cellular immune response), the formulation of the vaccine. It is expected that the amount will fall in a relatively broad range that can be determined through routine trials.

Reference herein to "immuno-interactive" includes reference to any interaction, reaction, or other form of association between molecules and in particular where one of the molecules is, or mimics, a component of the immune system.

By "immuno-interactive fragment" is meant a fragment of the (alpha)C portion of a mammalian inhibin alpha subunit which fragment elicits an immune response against the said alpha subunit, and preferably against a human inhibin alpha subunit. For example, in the case of an immuno-interactive fragment according to any one of SEQ ID NO: 3, 4, 5, 6, 21, 22, 23, 30, 31, 32, 35, 36, 37, 38, 39, 40, 55, 56, 57, 58, 59, 60, 68, 69, 70, 71, 72 and 73, the said fragment must elicit an immune response that includes the production of elements that specifically bind the (alpha)C portion of a mammalian inhibin alpha subunit. As used herein, the term "immuno-interactive fragment" includes deletion mutants and small peptides, for example of at least six, preferably at least 8 and more preferably at least 20 contiguous amino acids, which comprise antigenic determinants or epitopes. Several such fragments may be joined together. Peptides of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a polypeptide of the invention with proteinases such as endoLys-C, endoArg-C, endoGlu-C and staphylococcus V8-protease. The digested fragments can be purified by, for example, high performance liquid chromatographic (HPLC) techniques.

Reference herein to "inhibin" includes all forms of the molecule including its precursor forms. For example, the term "inhibin" includes inhibin A, inhibin B, free inhibin alpha subunit, Pro(alpha)N(alpha)C, Pro(alpha)C and (alpha)C. Dimeric and monomeric forms of inhibin are contemplated by the present invention. Furthermore, use of the term "inhibin" is not to impart any functional limitation on the molecule since subunits such as Pro(alpha)C or Pro(alpha)N (alpha)C may not have inhibin-like properties but are yet still useful in assays according to the present invention. Most preferably, the assays of the invention detect the inhibin alpha subunit and reference herein to "inhibin" includes, in a preferred embodiment, the alpha subunit alone or a variant or derivative thereof including, but not limited to, Pro(alpha)C and (alpha)C.

By "isolated" is meant material that is substantially or essentially free from components that normally accompany it in its native state. For example, an "isolated polynucleotide", as used herein, refers to a polynucleotide, which has been purified from the sequences which flank it in a naturally occurring state, e.g., a DNA fragment which has been removed from the sequences which are normally adjacent to the fragment.

By "obtained from" is meant that a sample such as, for example, a nucleic acid extract is isolated from, or derived from, a particular source of the host. For example, the nucleic acid extract may be obtained from tissue isolated directly from the host.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

By "operably linked" is meant that transcriptional and translational regulatory nucleic acids are positioned relative to a polypeptide-encoding polynucleotide in such a manner that the polynucleotide is transcribed and the polypeptide is translated.

The term "ovarian cancer" as used herein includes collectively all the major forms of the disease such as forms classified as serous, mucinous, granulosa cell tumor and miscellaneous as well as cancers related to ovarian cancer.

The term "patient" refers to patients of human or other mammal and includes any individual it is desired to examine or treat using the methods of the invention. However, it will be understood that "patient" does not imply that symptoms are present. Suitable mammals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes).

By "pharmaceutically-acceptable carrier" is meant a solid or liquid filler, diluent or encapsulating substance that may be safely used in topical or systemic administration.

The term "polynucleotide" or "nucleic acid" as used herein designates mRNA, RNA, cRNA, cDNA or DNA. The term typically refers to oligonucleotides greater than 30 nucleotides in length.

The terms "polynucleotide variant" refer to polynucleotides displaying substantial sequence identity with a reference polynucleotide sequence or polynucleotides that hybridize with a reference sequence under stringent conditions that are defined hereinafter. These terms also encompasses polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. The terms "polynucleotide sequence variant" and "variant" also include naturally occurring allelic variants.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

The term "polypeptide variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. Accordingly, polypeptide variants as used herein encompass polypeptides that will elicit an immune response against the (alpha)C portion of a mammalian inhibin alpha subunit.

By "primer" is meant an oligonucleotide which, when paired with a strand of DNA, is capable of initiating the synthesis of a primer extension product in the presence of a suitable polymerizing agent. The primer is preferably single-stranded for maximum efficiency in amplification but may alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridize and serve as a site for the initiation of synthesis. By "substantially complementary", it is meant that the primer is sufficiently complementary to hybridize with a target nucleotide sequence. Preferably, the primer contains no mismatches with the template to which it is designed to hybridize but this is not essential. For example, non-complementary nucleotides may be attached to the 5'-end of the primer, with the remainder of the primer sequence being complementary to the template. Alternatively, non-complementary nucleotides or a stretch of non-complementary nucleotides can be interspersed into a primer, provided that the primer sequence has sufficient complementarity with the sequence of the template to hybridize therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another nucleic acid, often called the "target nucleic acid", through complementary base pairing. Probes may bind target nucleic acids lacking complete sequence complementarity with the probe, depending on the stringency of the hybridization conditions. Probes can be labeled directly or indirectly.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

By "reporter molecule" as used in the present specification is meant a molecule that, by its chemical nature, provides an analytically identifiable signal that allows the detection of a complex comprising an antigen-binding molecule and its target antigen. The term "reporter molecule" also extends to use of cell agglutination or inhibition of agglutination such as red blood cells on latex beads, and the like.

Terms used to describe sequence relationships between two or more polynucleotides or polypeptides include "reference sequence", "comparison window", "sequence identity", "percentage of sequence identity" and "substantial identity". A "reference sequence" is at least 6 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology", John Wiley & Sons Inc, 1994-1998, Chapter 15.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

"Stringency" as used herein, refers to the temperature and ionic strength conditions, and presence or absence of certain organic solvents, during hybridization. The higher the stringency, the higher will be the degree of complementarity between immobilized nucleotide sequences and the labeled polynucleotide sequence.

"Stringent conditions" refers to temperature and ionic conditions under which only nucleotide sequences having a high frequency of complementary bases will hybridize. The stringency required is nucleotide sequence dependent and depends upon the various components present during hybridization. Generally, stringent conditions are selected to be about 10 to 20° C. lower than the thermal melting point ($T_m$) for the specific sequence at a defined ionic strength and pH. The $T_m$ is the temperature (under defined ionic strength and pH) at which 50% of a target sequence hybridizes to a complementary probe.

The term "substantially pure" as used herein describes a compound, e.g., a peptide that has been separated from components that naturally accompany it. Typically, a compound is substantially pure when at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis. A compound, e.g., a polypeptide is also substantially purified when it is essentially free of naturally associated components when it is separated from the native contaminants which accompany it in its natural state.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

Throughout this specification and the appended claims, unless the context requires otherwise, the words "comprise", "comprises" and "comprising" will be understood to imply the inclusion of a stated integer or step or group of integers or steps but not the exclusion of any other integer or step or group of integers or steps.

2. Immuno-interactive Molecules of the Invention 2.1. Immuno-interactive Fragments of the (alpha)C Portion of a Mammalian Inhibin Alpha Subunit The present invention provides an immuno-interactive fragment of the (alpha)C portion of a mammalian inhibin alpha subunit, which fragment is interactive with a polyclonal antiserum raised against the said (alpha)C portion. Preferably, the polyclonal antiserum is an ovine polyclonal antiserum as for example obtained by the method by Robertson et al. (1997, J. Clin. Endocrinol. Metabol. 82:889-896).

Suitably, the mammalian inhibin alpha subunit is a human inhibin alpha subunit. Accordingly, the said (alpha)C portion preferably comprises the sequence set forth in SEQ ID NO: 2. SEQ ID NO: 2 encodes the (alpha)C portion of human inhibin alpha subunit and corresponds to a 134-amino acid residue fragment of human inhibin alpha subunit, spanning residue 233 through residue 366 of the inhibin alpha subunit precursor as for example disclosed under Accession No. AAA59166 of the GenPept database (National Center for Biotechnology Information).

In a preferred embodiment, the immuno-interactive fragment comprises the sequence set forth in any one or more of SEQ ID NO: 3, 4, 5, 6, 18, 19, 20, 21, 22, 23, 30, 31, 32, 35, 36, 37, 38, 39, 40, 55, 56, 57, 58, 59, 60, 68, 69, 70, 71, 72 and 73. The corresponding positions of these immuno-interactive fragments relative to the amino acid sequence of the (alpha)C portion of human inhibin alpha subunit (set forth in SEQ ID NO: 2) are presented in Tables 1 and 7 infra.

2.2. Identification of Immuno-interactive Fragments

Immuno-interactive fragments may be identified according to any suitable procedure known in the art. For example, a suitable method may include generating a fragment of a polypeptide according to any one or more of SEQ ID NO: 3, 4, 5, 6, 18, 19, 20, 21, 22, 23, 30, 31, 32, 35, 36, 37, 38, 39, 40, 55, 56, 57, 58, 59, 60, 68, 69, 70, 71, 72 and 73, administering the fragment to a mammal, and detecting an immune response in the mammal. Such response will include production of elements that specifically bind the (alpha)C portion of a mammalian inhibin alpha subunit, preferably the (alpha)C portion of human inhibin alpha subunit.

Prior to testing a particular fragment for immunoreactivity in the above method, a variety of predictive methods may be used to deduce whether a particular fragment can be used to obtain an antibody that cross-reacts with the native antigen. These predictive methods may be based on amino-terminal or carboxyl-terminal sequences as for example described in Chapter 11.14 of Ausubel et al., (1994-1998, supra). Alternatively, these predictive methods may be based on predictions of hydrophilicity as for example described by Kyte and Doolittle (1982, J. Mol. Biol. 157:105-132) and Hopp and Woods (1983, Mol. Immunol. 20:483-489), or predictions of secondary structure as for example described by Choo and Fasman (1978, Ann. Rev. Biochem. 47:251-276).

Generally, peptide fragments consisting of 10 to 15 residues provide optimal results. Peptides as small as 6 or as large as 20 residues have worked successfully. Such peptide fragments may then be chemically coupled to a carrier molecule such as keyhole limpet hemocyanin (KLH) or bovine serum albumin (BSA) as for example described in Chapters 11.14 and 11.15 of Ausubel et al., (1994-1998, supra).

The peptides may be used to immunize a mammal as for example discussed above. Antibody titers against the native or parent polypeptide from which the peptide was selected may then be determined by radioimmunoassay or ELISA as for instance described in Chapters 11.16 and 114 of Ausubel et al., (1994-1998, supra).

Antibodies may then be purified from a suitable biological fluid of the animal by ammonium sulfate fractionation or by chromatography as is well known in the art. Exemplary protocols for antibody purification is given in Chapters 10.11 and 11.13 of Ausubel et al., (1994-1998, supra). Immunoreactivity of the antibody against the native or parent polypeptide may be determined by any suitable procedure such as, for example, western blot.

Polypeptide Variants

The invention also contemplates polypeptide variants of the immuno-interactive fragment of the invention wherein said variants elicit an immune response against the (alpha)C portion of a mammalian inhibin alpha subunit the (alpha)C portion of a mammalian inhibin alpha subunit. In general, variants will be at least 75% homologous, more suitably at least 80%, preferably at least 85%, and more preferably at least 90% homologous to an immuno-interactive fragment as for example shown in SEQ ID NO: 3, 4, 5, 6, 18, 19, 20, 21, 22, 23, 30, 31, 32, 35, 36, 37, 38, 39, 40, 55, 56, 57, 58, 59, 60, 68, 69, 70, 71, 72 and 73. It is preferred that variants display at least 60%, more suitably at least 70%, preferably at least 75%, more preferably at least 80%, more preferably at least 85%, more preferably at least 90% and still more preferably at least 95% sequence identity with an immuno-interactive fragment as for example shown in SEQ ID NO: 3, 4, 5, 6, 18, 19, 20, 21, 22, 23, 30, 31, 32, 35, 36, 37, 38, 39, 40, 55, 56, 57, 58, 59, 60, 68, 69, 70, 71, 72 and 73. In this respect, the window of comparison preferably spans about the full length of the immuno-interactive fragment.

Suitably, the polypeptide variants of the invention will cross-react with or mimic immunologically an epitope of the (alpha)C portion of a mammalian inhibin alpha subunit. Thus, polypeptide variants according to the invention may bind an antigen-binding molecule that also binds an epitope of the (alpha)C portion of a mammalian inhibin alpha subunit and preferably the (alpha)C portion of a human inhibin alpha subunit.

Suitable polypeptide variants may be identified by combining a compound suspected of being a variant with at least one antigen-binding molecule that binds to the said (alpha)C portion. If a conjugate is formed comprising the compound and the antigen-binding molecule, this is indicative of the compound being a variant of the aforementioned immuno-interactive fragment. In a preferred embodiment, the compound is preferably a polypeptide (e.g., a modified polypeptide) whose sequence is distinguished from the immuno-interactive fragment by substitution, deletion and/or addition of at least one amino acid.

2.3.1. Assay Formats for Detecting Polypeptide Variants

Any suitable technique for determining formation of the conjugate may be used. For example, the antigen-binding molecule may be utilized in conventional immunoassays. Such immunoassays may include, but are not limited to, radioimmunoassays (RIAs), enzyme-linked immunosorbent assays (ELISAs) and immunochromatographic techniques (ICTs) which are well known those of skill in the art. For example, reference may be made to Coligan et al. ("Current Protocols in Immunology", John Wiley & Sons, Inc, 1995-1997), in which a variety of immunoassays are described that may be used in accordance with the present invention. In this regard, the invention contemplates any immunoassay that can detect the presence of a conjugate as herein described. For example, immunoassays may include competitive and non-competitive assays as understood in the art. Such immunoassays may be carried out in solution or, at least in part, on solid supports, e.g., microtiter plates, polystyrene beads, nitrocellulose membranes, glass fiber membranes, immunochromatographic strips, and the like. The two most common formats for immunoassays are competitive and non-competitive (sandwich) formats.

In a competitive format, an antigen-binding molecule such as a polyclonal or monoclonal antibody is bound to a solid support. This antibody is suitably capable of binding a polypeptide according to SEQ ID NO: 2 or immuno-interactive fragment thereof. A solution of antigen labeled to permit detection (e.g., a labeled polypeptide or immuno-interactive fragment) is allowed to compete with unlabelled antigen (e.g., a compound suspected of being a variant) for the solid phase antibody. The extent to which the labeled antigen is bound to the solid phase or is detected in the solution phase can be used as a measure of the presence of said conjugate.

In a non-competitive, or sandwich format, a polyclonal or preferably a monoclonal antibody is bound to a solid support. Such antibody is suitably capable of binding a polypeptide according to SEQ ID NO: 2 or immuno-interactive fragment thereof. In the case of a polyclonal antibody bound to the solid support, the sample containing the suspected antigen (i.e., a compound suspected of being said variant) is allowed to contact the solid phase in order for the antigen to bind to the antibody on the solid phase. Typically, after an incubation step, the sample is separated from the solid phase, which is then washed and incubated in the presence of additional polyclonal antibody that has been labeled to permit detection. Subsequently, the unbound labeled antibody is separated from the solid phase and the amount of labeled antibody in either the solution phase or bound to the solid phase in an antibody:antigen:antibody sandwich is determined as a measure of the presence of said conjugate. In the case of a non-competitive format employing monoclonal antibodies, a pair of monoclonal antibodies is typically utilized, one bound to the solid support and the other labeled to permit detection. The use of monoclonal antibody pairs that recognize different epitopic sites on an antigen makes it possible to conduct simultaneous immunometric assays in which the antigen and labeled antibody incubations do not require the intermediate steps of prior processes.

Alternatively, solid phase detection of the conjugate may be determined by immunoaffinity chromatography, as for example described by Coligan et al., (supra, in particular Chapter 9.5) and Ausubel et al. ("Current Protocols in Molecular Biology", John Wiley & Sons Inc, 1994-1998, in particular Chapter 10.11), by immunoblotting, as for example described by Ausubel et al. (supra, in Chapter 10.8), or by immunoprecipitation, as for example described by Ausubel et al. (supra, in Chapter 10.16).

Solution-phase immunoassays are also contemplated by the present invention. For instance, detection of said conjugate may be carried out in solution using flow cytometric analysis as for example described in Shapiro ("Practical Flow Cytometry", 3rd ed., Wiley-Liss, New York, 1995).

2.3.2. Methods of Producing Polypeptide Variants 2.3.2.1. Mutagenesis

Polypeptide variants according to the invention can be identified either rationally, or via established methods of mutagenesis (see, for example, Watson et al., "Molecular Biology of the Gene", Fourth Edition, Benjamin/Cummings, Menlo Park, Calif., 1987). Significantly, a random mutagenesis approach requires no a priori information about the gene sequence that is to be mutated. This approach has the advantage that it assesses the desirability of a particular mutant based on its function, and thus does not require an understanding of how or why the resultant mutant protein has adopted a particular conformation. Indeed, the random mutation of target gene sequences has been one approach used to obtain mutant proteins having desired characteristics (Leatherbarrow, 1986, J. Prot. Eng. 1:7-16; Knowles, 1987, Science 236:1252-1258; Shaw, 1987, Biochem. J. 246:1-17; Gerit, 1987, Chem. Rev. 87:1079-1105). Alternatively, where a particular sequence alteration is desired, methods of site-directed mutagenesis can be employed. Thus, such methods may be used to selectively alter only those amino acids of the protein that are believed to be important (Craik, 1985, Science 228:291-297; Cronin, et al., 1988, Biochemistry 27:4572-4579; Wilks, et al., 1988, Science 242:1541-1544).

Variant peptides or polypeptides, resulting from rational or established methods of mutagenesis or from combinatorial chemistries as hereinafter described, may comprise conservative amino acid substitutions. Exemplary conservative substitutions in an immuno-interactive polypeptide or polypeptide fragment according to the invention may be made according to the following table:

TABLE A

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those shown in Table A. Other replacements would be non-conservative substitutions and relatively fewer of these may be tolerated. Generally, the substitutions which are likely to produce the greatest changes in a polypeptide's properties are those in which (a) a hydrophilic residue (e.g., Ser or Thr) is substituted for, or by, a hydrophobic residue (e.g., Ala, Leu, Ile, Phe or Val); (b) a cysteine or proline is substituted for, or by, any other residue; (c) a residue having an electropositive side chain (e.g., Arg, His or Lys) is substituted for, or by, an electronegative residue (e.g., Glu or Asp) or (d) a residue having a bulky side chain (e.g., Phe or Trp) is substituted for, or by, one having a smaller side chain (e.g., Ala, Ser)or no side chain (e.g., Gly).

What constitutes suitable variants may be determined by conventional techniques. For example, nucleic acids encoding a polypeptide according to any one or more of SEQ ID NO: 3, 4, 5, 6, 18, 19, 20, 21, 22, 23, 30, 31, 32, 35, 36, 37, 38, 39, 40, 55, 56, 57, 58, 59, 60, 68, 69, 70, 71, 72 and 73 can be mutated using either random mutagenesis for example using transposon mutagenesis, or site-directed mutagenesis as described, for example, in Section 3.2 herein.

2.3.2.2. Peptide Libraries Produced by Combinatorial Chemistry

A number of facile combinatorial technologies can be utilized to synthesize molecular libraries of immense diversity. In the present case, variants of an immuno-interactive polypeptide, preferably an immuno-interactive polypeptide fragment according to the invention, can be synthesized using such technologies. Variants can be screened subsequently using the methods described in Section 2.3.1.

Preferably, soluble synthetic peptide combinatorial libraries (SPCLs) are produced which offer the advantage of working with free peptides in solution, thus permitting adjustment of peptide concentration to accommodate a particular assay system. SPCLs are suitably prepared as hexamers. In this regard, a majority of binding sites is known to involve four to six residues. Cysteine is preferably excluded from the mixture positions to avoid the formation of disulfides and more difficult-to-define polymers. Exemplary methods of producing SPCLs are disclosed by Houghten et al. (1991, Nature 354:84-86; 1992, BioTechniques 13:412-421), Appel et al. (1992, Immunomethods 1:17-23), and Pinilla et al. (1992, BioTechniques 13:901-905; 1993, Gene 128:71-76).

Preparation of combinatorial synthetic peptide libraries may employ either t-butyloxycarbonyl (t-Boc) or 9-fluorenylmethyloxycarbonyl (Fmoc) chemistries (see Chapter 9.1, of Coligan et al., supra; Stewart and Young, 1984, Solid Phase Peptide Synthesis, 2nd ed. Pierce Chemical Co., Rockford, Ill; and Atherton and Sheppard, 1989, Solid Phase Peptide Synthesis: A Practical Approach. IRL Press, Oxford) preferably, but not exclusively, using one of two different approaches. The first of these approaches, suitably termed the "split-process-recombine" or "split synthesis" method, was described first by Furka et al. (1988, 14th Int. Congr. Biochem., Prague, Czechoslovakia 5:47; 1991, Int. J. Pept. Protein Res. 37:487-493) and Lam et al. (1991, Nature 354:82-84), and reviewed later by Eichler et al. (1995, Medicinal Research Reviews 15(6):481-496) and Balkenhohl et al. (1996, Angew. Chem. Int. Ed. Engl. 35:2288-2337). Briefly, the split synthesis method involves dividing a plurality of solid supports such as polymer beads into n equal fractions representative of the number of available amino acids for each step of the synthesis (e.g., 20 L-amino acids), coupling a single respective amino acid to each polymer bead of a corresponding fraction, and then thoroughly mixing the polymer beads of all the fractions together. This process is repeated for a total of x cycles to produce a stochastic collection of up to $N^x$ different compounds. The peptide library so produced may be screened with a suitably labeled monoclonal antibody. Upon detection, some of the positive beads are selected for sequencing to identify the active peptide. Such peptide may be subsequently cleaved from the beads, and assayed using the same antibody to identify the most active peptide sequence.

The second approach, the chemical ratio method, prepares mixed peptide resins using a specific ratio of amino acids empirically defined to give equimolar incorporation of each amino acid at each coupling step. Each resin bead contains a mixture of peptides. Approximate equimolar representation can be confirmed by amino acid analysis (Dooley and Houghten, 1993, Proc. Natl. Acad. Sci. USA 90:10811-10815; Eichler and Houghten, 1993, Biochemistry 32:11035-11041). Preferably, the synthetic peptide library is produced on polyethylene rods, or pins, as a solid support, as for example disclosed by Geysen et al. (1986, Mol. Immunol. 23:709-715). An exemplary peptide library of this type may consist of octapeptides in which the third and fourth position are defined with each of the 20 amino acids, whereas the remaining six positions are present as mixtures. This peptide library can be represented by the formula $Ac-XXO_1O_2XXXX-S_s$, where $S_s$ is the solid support. Peptide mixtures remain on the pins when assayed against a soluble receptor molecule. For example, the peptide library of Geysen (1986, Immunol. Today 6:364-369; and Geysen et al., Ibid), comprising for example dipeptides, is first screened for the ability to bind to a target molecule. The most active dipeptides are then selected for an additional round of testing comprising linking, to the starting dipeptide, an additional residue (or by internally modifying the components of the original starting dipeptide) and then screening this set of candidates for the desired activity. This process is reiterated until the binding partner having the desired properties is identified.

2.3.2.3. Alanine Scanning Mutagenesis

In one embodiment, the invention herein utilizes a systematic analysis of an immuno-interactive fragment according to the invention to determine the residues in the said (alpha)C portion that are involved in the interaction of the said fragment with an antigen-binding molecule that binds to said (alpha)C portion. Such analysis is conveniently performed using recombinant DNA technology. In general, the DNA sequence encoding the immuno-interactive fragment is cloned and manipulated so that it may be expressed in a convenient host. DNA encoding the immuno-interactive fragment can be obtained from a genomic library, from cDNA derived from mRNA in cells expressing the said (alpha)C portion, or by synthetically constructing the DNA sequence (Sambrook et al., supra; Ausubel et al., supra).

The wild-type DNA encoding the immuno-interactive fragment is then inserted into an appropriate plasmid or vector as described herein. In particular, prokaryotes are preferred for cloning and expressing DNA sequences to produce variants of the immuno-interactive fragment. For example, E. coli K12 strain 294 (ATCC No. 31446) may be used, as well as E. coli B, E. coli X1776 (ATCC No. 31537), and E. coli c600 and c600hfl, and E. coli W3110 (F⁻, gamma⁻, prototrophic, ATCC No. 27325), bacilli such as Bacillus subtilis, and other enterobacteriaceae such as Salmonella typhimurium or Serratia marcescens, and various Pseudomonas species. A preferred prokaryote is E. coli W3110 (ATCC 27325).

Once the immuno-interactive fragment is cloned, site-specific mutagenesis as for example described by Carter et al. (1986, Nucl. Acids Res., 13:4331) or by Zoller et al. (1987, Nucl. Acids Res., 10:6487), cassette mutagenesis as for example described by Wells et al. (1985, Gene 34:315), restriction selection mutagenesis as for example described by Wells et al. (1986, Philos. Trans. R. Soc. London Ser. A 317:415), or other known techniques may be performed on the cloned DNA to produce the variant DNA that encodes for the changes in amino acid sequence defined by the residues being substituted. When operably linked to an appropriate expression vector, variants are obtained. In some cases, recovery of the variant may be facilitated by expressing and secreting such molecules from the expression host by use of an appropriate signal sequence operably linked to the DNA sequence encoding the immuno-interactive fragment parent or variant. Such methods are well known to those skilled in the art. Of course, other methods may be employed to produce such polypeptides such as the in vitro chemical synthesis of the desired immuno-interactive fragment variant (Barany et al., 1979, In The Peptides, Gross et al., Eds., Academic Press, New York, Vol. 2, pp. 3-254).

Once the different the variants are produced, they are contacted with an antigen-binding molecule that binds to the said (alpha)C portion and the interaction, if any, between the antigen-binding molecule and each variant is determined. These activities are compared to the activity of the wild-type immuno-interactive fragment with the same antigen-binding molecule to determine which of the amino acid residues in the active domain or epitope are involved in the interaction with the antigen-binding molecule. The scanning amino acid used in such an analysis may be any different amino acid from that substituted, i.e., any of the 19 other naturally occurring amino acids.

The interaction between the antigen-binding molecule and parent and variant can be measured by any convenient assay as for example described herein. While any number of analytical measurements may be used to compare activities, a convenient one for binding of antigen-binding molecule is the dissociation constant $K_d$ of the complex formed between the variant and antigen-binding molecule as compared to the $K_d$ for the wild-type immuno-interactive fragment. Generally, a two-fold increase or decrease in $K_d$ per analogous residue substituted by the substitution indicates that the substituted residue(s) is active in the interaction of the wild-type immuno-interactive fragment with the target antigen-binding molecule.

When a suspected or known active amino acid residue is subjected to scanning amino acid analysis, the amino acid residues immediately adjacent thereto should be scanned. Three residue-substituted polypeptides can be made. One contains a scanning amino acid, preferably alanine, at position N that is the suspected or known active amino acid. The two others contain the scanning amino acid at position N+1 and N−1. If each substituted immuno-interactive fragment causes a greater than about two-fold effect on $K_d$ for the receptor, the scanning amino acid is substituted at position N+2 and N−2. This is repeated until at least one, and preferably four, residues are identified in each direction which have less than about a two-fold effect on $K_d$ or either of the ends of the wild-type immuno-interactive fragment are reached. In this manner, one or more amino acids along a continuous amino acid sequence that are involved in the interaction with the particular antigen-binding molecule can be identified.

The active amino acid residue identified by amino acid scan is typically one that contacts the receptor target directly. However, active amino acids may also indirectly contact the target through salt bridges formed with other residues or small molecules such as $H_2O$ or ionic species such as $Na^+$, $Ca^{+2}$, $Mg^{+2}$, or $Zn^{+2}$.

In some cases, the substitution of a scanning amino acid at one or more residues results in a residue-substituted polypeptide which is not expressed at levels that allow for the isolation of quantities sufficient to carry out analysis of its activity with the receptor. In such cases, a different scanning amino acid, preferably an isosteric amino acid, can be used.

Among the preferred scanning amino acids are relatively small, neutral amino acids. Such amino acids include alanine, glycine, serine, and cysteine. Alanine is the preferred scanning amino acid among this group because it eliminates the side-chain beyond the beta-carbon and is less likely to alter the main-chain conformation of the variant. Alanine is also preferred because it is the most common amino acid. Further, it is frequently found in both buried and exposed positions (Creighton, The Proteins, W. H. Freeman & Co., New York.; Chothia, 1976, J. Mol. Biol. 150:1). If alanine substitution does not yield adequate amounts of variant, an isosteric amino acid can be used. Alternatively, the following amino acids in decreasing order of preference may be used: Ser, Asn, and Leu.

Once the active amino acid residues are identified, isosteric amino acids may be substituted. Such isosteric substitutions need not occur in all instances and may be performed before any active amino acid is identified. Such isosteric amino acid substitution is performed to minimize the potential disruptive effects on conformation that some substitutions can cause. Isosteric amino acids are shown in the table below:

TABLE B

| Polypeptide Amino Acid | Isosteric Scanning Amino Acid |
|---|---|
| Ala (A) | Ser, Gly |
| Glu (E) | Gln, Asp |
| Gln (Q) | Asn, Glu |
| Asp (D) | Asn, Glu |
| Asn (N) | Ala, Asp |
| Leu (L) | Met, Ile |
| Gly (G) | Pro, Ala |
| Lys (K) | Met, Arg |
| Ser (S) | Thr, Ala |

TABLE B-continued

| Polypeptide Amino Acid | Isosteric Scanning Amino Acid |
|---|---|
| Val (V) | Ile, Thr |
| Arg (R) | Lys, Met, Asn |
| Thr (T) | Ser, Val |
| Pro (P) | Gly |
| Ile (I) | Met, Leu, Val |
| Met (M) | Ile, Leu |
| Phe (F) | Tyr |
| Tyr (Y) | Phe |
| Cys (C) | Ser, Ala |
| Trp (W) | Phe |
| His (H) | Asn, Gln |

The method herein can be used to detect active amino acid residues within different epitopes of an immuno-interactive fragment according to the invention. Once this identification is made, various modifications to the wild-type immuno-interactive fragment may be made to modify the interaction between the parent immuno-interactive fragment and one or more of the targets.

2.3.2.4. Polypeptide or Peptide Libraries Produced by Phage Display

The identification of variants can also be facilitated through the use of a phage (or phagemid) display protein ligand screening system as for example described by Lowman, et al. (1991, Biochemistry 30:10832-10838), Markland, et al. (1991, Gene 109:13-19), Roberts, et al. (1992, Proc. Natl. Acad. Sci. USA 89:2429-2433), Smith (1985, Science 228:1315-1317), Smith et al. (1990, Science 248:1126-1128) and Lardner et al. (U.S. Pat. No. 5,223,409). In general, this method involves expressing a fusion protein in which the desired protein ligand is fused to the N-terminus of a viral coat protein (such as the M13 Gene III coat protein, or a lambda coat protein).

In one embodiment, a library of phage is engineered to display novel peptides within the phage coat protein sequences. Novel peptide sequences are generated by random mutagenesis of gene fragments encoding an immuno-interactive polypeptide fragment using error-prone PCR, or by in vivo mutation by *E. coli* mutator cells. The novel peptides displayed on the surface of the phage are placed in contact, with an antigen binding molecule such as an antibody or antibody fragment against the particular immuno-interactive fragment on which the novel peptide sequences are based. Phage that display coat protein having peptides that are capable of binding to such antibodies are immobilized by such treatment, whereas all other phage can be washed away. After the removal of unbound phage, the bound phage can be amplified, and the DNA encoding their coat proteins can be sequenced. In this manner, the amino acid sequence of the embedded peptide or polypeptide can be deduced.

In more detail, the method involves:

(a) constructing a replicable expression vector comprising a first polynucleotide encoding an immuno-interactive fragment of the invention, a second polynucleotide encoding at least a portion of a natural or wild-type phage coat protein wherein the first and second polynucleotides are heterologous, and a transcription regulatory element operably linked to the first and second polynucleotides, thereby forming a polynucleotide fusion encoding a fusion protein;

(b) mutating the vector at one or more selected positions within the first polynucleotide thereby forming a family of related vectors;

(c) transforming suitable host cells with the vectors;

(d) infecting the transformed host cells with a helper phage having a polynucleotide encoding the phage coat protein;

(e) culturing the transformed infected host cells under conditions suitable for forming recombinant phagemid particles containing at least a portion of the vector and capable of transforming the host, the conditions preferably adjusted so that no more than a minor amount of phagemid particles display more than one copy of the fusion protein on the surface of the particle;

(f) contacting the phagemid particles with an antigen-binding molecule that binds to the immuno-interactive fragment so that at least a portion of the phagemid particles bind to the antigen-binding molecule; and (g) separating the phagemid particles that bind from those that do not.

Preferably, the method further comprises transforming suitable host cells with recombinant phagemid particles that bind to the antigen-binding molecule and repeating steps (d) through (g) one or more times.

Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Even more preferably, the amount is less than 20%.

Typically in this method, the expression vector will further contain a secretory signal sequence fused to the DNA encoding each subunit of the polypeptide and the transcription regulatory element will be a promoter. Preferred promoters are selected from lac Z, lambdaPL, tac, T7 polymerase, tryptophan, and alkaline phosphatase promoters and combinations thereof. The method can also typically employ a helper phage selected from M13K07, M13R408, M13-VCS, and Phi X 174. The preferred helper phage is M13K07, and the preferred coat protein is the M13 Phage gene III coat protein. The preferred host is $E.$ $coli$, and protease-deficient strains of $E.$ $coli$.

Repeated cycles of variant selection are used to select for higher and higher affinity binding by the phagemid selection of multiple amino acid changes that are selected by multiple selection cycles. Following a first round of phagemid selection, involving a first region or selection of amino acids in the ligand polypeptide, additional rounds of phagemid selection in other regions or amino acids of the ligand polypeptide are conducted. The cycles of phagemid selection are repeated until the desired affinity properties of the ligand polypeptide are achieved.

It will be appreciated that the amino acid residues that form the binding domain of the immuno-interactive fragment may not be sequentially linked and may reside on different subunits of the polypeptide. That is, the binding domain tracks with the particular secondary structure at the binding site and not the primary structure. Thus, generally, mutations will be introduced into codons encoding amino acids within a particular secondary structure at sites directed away from the interior of the polypeptide so that they will have the potential to interact with the antigen-binding molecule.

The phagemid-display method herein contemplates fusing a polynucleotide encoding the immuno-interactive fragment (polynucleotide 1) to a second polynucleotide (polynucleotide 2) such that a fusion protein is generated during transcription. Polynucleotide 2 is typically a coat protein gene of a phage, and preferably it is the phage M13 gene III coat protein, or a fragment thereof. Fusion of polynucleotides 1 and 2 may be accomplished by inserting polynucleotide 2 into a particular site on a vector that contains polynucleotide 1, or by inserting polynucleotide 1 into a particular site on a vector that contains polynucleotide 2.

Between polynucleotide 1 and polynucleotide 2, DNA encoding a termination codon may be inserted, which termination codons include UAG (amber), UAA (ocher), and UGA (opel) (see for example, Davis et al., 1980, Microbiology, Harper and Row, New York, pp. 237, 245-247, and 274). The termination codon expressed in a wild-type host cell results in the synthesis of the polynucleotide 1 protein product without the polynucleotide 2 protein fused thereto. However, growth in a suppressor host cell results in the synthesis of detectable quantities of the fusion protein. In this regard, suppressor host cells contain a tRNA modified to insert an amino acid in the termination codon position of the mRNA, thereby resulting in production of detectable amounts of the fusion protein. Such suppressor host cells are well known and described, such as *E. coli* suppressor strain (Bullock et al., 1987, BioTechniques, 5:376-379). Any acceptable method may be used to place such a termination codon into the mRNA encoding the fusion polypeptide.

Accordingly, the suppressible codon can be inserted between the polynucleotide encoding the immuno-interactive fragment and a second polynucleotide encoding at least a portion of a phage coat protein. Alternatively, the suppressible termination codon may be inserted adjacent to the fusion site by replacing the last amino acid triplet in the polypeptide or the first amino acid triplet in the phage coat protein. When the phagemid containing the suppressible codon is grown in a suppressor host cell, it results in the detectable production of a fusion polypeptide containing the immuno-interactive fragment and the coat protein. When the phagemid is grown in a non-suppressor host cell, the immuno-interactive fragment is synthesized substantially without fusion to the phage coat protein due to termination at the inserted suppressible triplet encoding UAG, UAA, or UGA. In the non-suppressor cell the polypeptide is synthesized and secreted from the host cell due to the absence of the fused phage coat protein which otherwise anchored it to the host cell.

The immuno-interactive fragment may be altered at one or more selected codons. An alteration is defined as a substitution, deletion, or insertion of one or more codons in the gene encoding the immuno-interactive fragment that results in a change in the amino acid sequence of the immuno-interactive fragment as compared with the unaltered or native sequence of the said fragment. Preferably, the alterations will be by substitution of at least one amino acid with any other amino acid in one or more regions of the molecule. The alterations may be produced by a variety of methods known in the art. These methods include, but are not limited to, oligonucleotide-mediated mutagenesis and cassette mutagenesis as described for example herein.

For preparing the antigen-binding molecule and binding it with the phagemid, the antigen-binding molecule is attached to a suitable matrix such as agarose beads, acrylamide beads, glass beads, cellulose, various acrylic copolymers, hydroxyalkyl methacrylate gels, polyacrylic acid, polymethacrylic copolymers, nylon, neutral and ionic carriers, and the like. Attachment of the antigen-binding molecule to the matrix may be accomplished by methods described in Methods Enzymol., 44:(1976), or by other means known in the art.

After attachment of the antigen-binding molecule to the matrix, the immobilized target is contacted with the library of phagemid particles under conditions suitable for binding of at least a portion of the phagemid particles with the immobilized target. Normally, the conditions, including pH, ionic strength, temperature, and the like will mimic physiological conditions.

Bound phagemid particles ("binders") having high affinity for the immobilized target are separated from those having a low affinity (and thus do not bind to the target) by washing. Binders may be dissociated from the immobilized target by a variety of methods. These methods include competitive dissociation using the wild-type ligand, altering pH and/or ionic strength, and methods known in the art.

Suitable host cells are infected with the binders and helper phage, and the host cells are cultured under conditions suitable for amplification of the phagemid particles. The phagemid particles are then collected and the selection process is repeated one or more times until binders having the desired affinity for the target molecule are selected.

2.3.2.5. Rational Drug Design

Variants of naturally occurring immuno-interactive polypeptides or polypeptide fragments according to the invention may also be obtained using the principles of conventional or of rational drug design as for example described by Andrews, et al. (In: "Proceedings of the Alfred Benzon Symposium," vol. 28, pp. 145-165, Munksgaard, Copenhagen, 1990), McPherson (1990, Eur. J. Biochem. 189:1-24), Hol et al. (1989, In: "Molecular Recognition: Chemical and Biochemical Problems", Roberts, Ed., R. Soc. Chem. pp. 84-93), Hol (1989, Arzneim-Forsch. 39:1016-1018), Hol (1986, Angew. Chem. Int. Ed. Engl. 25:767-778).

In accordance with the methods of conventional drug design, the desired variant molecules are obtained by randomly testing molecules whose structures have an attribute in common with the structure of a "native" immuno-interactive fragment according to the invention. The quantitative contribution that results from a change in a particular group of a binding molecule can be determined by measuring the capacity of competition or cooperativity between the native immuno-interactive polypeptide or polypeptide fragment and the putative polypeptide variant.

In one embodiment of rational drug design, the polypeptide variant is designed to share an attribute of the most stable three-dimensional conformation of an immuno-interactive polypeptide or polypeptide fragment according to the invention. Thus, the variant may be designed to possess chemical groups that are oriented in a way sufficient to cause ionic, hydrophobic, or van der Waals interactions that are similar to those exhibited by the immuno-interactive polypeptide or polypeptide fragment. In a second method of rational design, the capacity of a particular immuno-interactive polypeptide or polypeptide fragment to undergo conformational "breathing" is exploited. Such "breathing"—the transient and reversible assumption of a different molecular conformation—is a well-appreciated phenomenon, and results from temperature, thermodynamic factors, and from the catalytic activity of the molecule. Knowledge of the 3-dimensional structure of the immuno-interactive polypeptide or polypeptide fragment facilitates such an evaluation. An evaluation of the natural conformational changes of an immuno-interactive polypeptide or polypeptide fragment facilitates the recognition of potential hinge sites, potential sites at which hydrogen bonding, ionic bonds or van der Waals bonds might form or might be eliminated due to the breathing of the molecule, etc. Such recognition permits the identification of the additional conformations that the immuno-interactive polypeptide or polypeptide fragment could assume, and enables the rational design and production of immunomimetics that share such conformations.

The preferred method for performing rational immunomimetic design employs a computer system capable of forming a representation of the three-dimensional structure of the immuno-interactive polypeptide or polypeptide fragment (such as those obtained using RIBBON (Priestle, J., 1988, J. Mol. Graphics 21:572), QUANTA (Polygen), InSite (Biosyn), or Nanovision (American Chemical Society)). Such analyses are exemplified by Hol et al. (In: "Molecular Recognition: Chemical and Biochemical Problems", supra, Hol (1989, supra) and Hol (1986, supra).

In lieu of such direct comparative evaluations of putative polypeptide variants, screening assays may be used to identify such molecules. Such assays will preferably exploit the capacity of the variant to bind to an antigen-binding molecule as described in Section 2.3.1.

2.4. Polypeptide Derivatives

With reference to suitable derivatives of the invention, such derivatives include amino acid deletions and/or additions to the immuno-interactive fragment or variant of the invention, wherein said derivatives elicit an immune response in a mammal which response includes elements that specifically bind to the said (alpha)C portion. "Additions" of amino acids may include fusion of the immuno-interactive fragments and polypeptide variants of the invention with other polypeptides or proteins. For example, it will be appreciated that said immuno-interactive fragments or variants may be incorporated into larger polypeptides, and that such larger polypeptides may also be expected to elicit the said immune response.

The immuno-interactive fragments or variants of the invention may be fused to a further protein, for example, which is not derived from the original host. The further protein may assist in the purification of the fusion protein. For instance, a polyhistidine tag or a maltose binding protein may be used in this respect as described in more detail below. Other possible fusion proteins are those which produce an immunomodulatory response. Particular examples of such proteins include Protein A or glutathione S-transferase (GST).

Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the immuno-interactive fragments and variants of the invention.

Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2,4,6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulfhydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulfides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulfonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. A list of unnatural amino acids contemplated by the present invention is shown in Table C.

TABLE C

| Non-conventional amino acid |
| --- |
| alpha-aminobutyric acid |
| alpha-amino-alpha-methylbutyrate |
| Aminocyclopropane-carboxylate |
| Aminoisobutyric acid |
| Aminonorbornyl-carboxylate |
| Cyclohexylalanine |
| Cyclopentylalanine |
| L-N-methylisoleucine |
| D-alanine |
| D-arginine |
| D-aspartic acid |
| D-cysteine |
| D-glutamate |
| D-glutamic acid |
| D-histidine |
| D-isoleucine |
| D-leucine |
| D-lysine |
| D-methionine |
| D-ornithine |
| D-phenylalanine |
| D-proline |
| D-serine |
| D-threonine |
| D-tryptophan |
| D-tyrosine |
| D-valine |
| D-alpha-methylalanine |
| D-alpha-methylarginine |
| D-alpha-methylasparagine |
| D-alpha-methylaspartate |
| D-alpha-methylcysteine |
| D-alpha-methylglutamine |
| D-alpha-methylhistidine |
| D-alpha-methylisoleucine |
| D-alpha-methylleucine |
| D-alpha-methyllysine |
| D-alpha-methylmethionine |
| D-alpha-methylornithiine |
| D-alpha-methylphenylalanine |
| D-alpha-methylproline |
| D-alpha-methylserine |
| D-alpha-methylthreonine |
| D-alpha-methyltryptophan |
| D-alpha-methyltyrosine |
| L-alpha-methylleucine |
| L-alpha-methylmethionine |
| L-alpha-methylnorvatine |
| L-alpha-methylphenylalanine |
| L-alpha-methylserine |

TABLE C-continued

| Non-conventional amino acid |
| --- |
| L-alpha-methyltryptophan |
| L-alpha-methylvaline |
| N-(N-(2,2-diphenylethyl carbamylmethyl)glycine |
| 1-carboxy-1-(2,2-diphenyl-ethyl amino)cyclopropane |
| L-N-methylalanine |
| L-N-methylarginine |
| L-N-methylasparagine |
| L-N-methylaspartic acid |
| L-N-methylcysteine |
| L-N-methylglutamine |
| L-N-methylglutamic acid |
| L-N-methylhistidine |
| L-N-methylleucine |
| L-N-methyllysine |
| L-N-methylmethionine |
| L-N-methylnorleucine |
| L-N-methylnorvaline |
| L-N-methylornithine |
| L-N-methylphenylalanine |
| L-N-methylproline |
| L-N-medlylserine |
| L-N-methylthreonine |
| L-N-methyltryptophan |
| L-N-methyltyrosine |
| L-N-methylvaline |
| L-N-methylethylglycine |
| L-N-methyl-t-butylglycine |
| L-norleucine |
| L-norvaline |
| alpha-methyl-aminoisobutyrate |
| alpha-methyl-gamma-aminobutyrate |
| alpha-methylcyclohexylalanine |
| alpha-methylcylcopentylalanine |
| alpha-methyl-alpha-napthylalanine |
| alpha-methylpenicillamine |
| N-(4-aminobutyl)glycine |
| N-(2-aminoethyl)glycine |
| N-(3-aminopropyl)glycine |
| N-amino-alpha-methylbutyrate |
| alpha-napthylalanine |
| N-benzylglycine |
| N-(2-carbamylediyl)glycine |
| N-(carbamylmethyl)glycine |
| N-(2-carboxyethyl)glycine |
| N-(carboxymethyl)glycine |
| N-cyclobutylglycine |
| N-cycloheptylglycine |
| N-cyclohexylglycine |
| N-cyclodecylglycine |
| L-alpha-methyllysine |
| L-alpha-methylnorleucine |
| L-alpha-methylornithine |
| L-alpha-methylproline |
| L-alpha-methylthreonine |
| L-alpha-methyltyrosine |
| L-N-methylhomophenylalanine |
| N-(N-(3,3-diphenylpropyl carbamylmethyl)glycine |

The invention also extends to covalently modifying an immuno-interactive fragment or variant of the invention with dinitrophenol, in order to render it immunogenic in humans.

Also contemplated is the use of crosslinkers, for example, to stabilize 3D conformations of the immuno-interactive fragments or variants of the invention, using homo-bifunctional cross linkers such as bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety or carbodiimide. In addition, peptides can be conformationally constrained, for example, by introduction of double bonds between $C_{alpha}$ and $C_{beta}$ atoms of amino acids, by incorporation of $C_{alpha}$ and $N_{alpha}$-methylamino acids, and by formation of cyclic peptides or analogues by introducing covalent bonds such as forming an amide bond between the N and C termini between two side chains or between a side chain and the N or C terminus of the peptides or analogues. For example, reference may be made to Marlowe (1993, Biorg. Med. Chem. Lett. 3:437-44) who describes peptide cyclization on TFA resin using trimethylsilyl (TMSE) ester as an orthogonal protecting group; Pallin and Tam (1995, J. Chem. Soc. Chem. Comm. 2021-2022) who describe the cyclization of unprotected peptides in aqueous solution by oxime formation; Algin et al (1994, Tetrahedron Lett. 35:9633-9636) who disclose solid-phase synthesis of head-to-tail cyclic peptides via lysine side-chain anchoring; Kates et al (1993, Tetrahedron Lett. 34:1549-1552) who describe the production of head-to-tail cyclic peptides by three-dimensional solid phase strategy; Tumelty et al (1994, J. Chem. Soc. Chem. Comm. 1067-1068) who describe the synthesis of cyclic peptides from an immobilized activated intermediate, wherein activation of the immobilized peptide is carried out with N-protecting group intact and subsequent removal leading to cyclization; McMurray et al (1994, Peptide Res. 7:195-206) who disclose head-to-tail cyclization of peptides attached to insoluble supports by means of the side chains of aspartic and glutamic acid; Hruby et al (1994, Reactive Polymers 22:231-241) who teach an alternate method for cyclizing peptides via solid supports; and Schmidt and Langer (1997, J. Peptide Res. 49:67-73) who disclose a method for synthesizing cyclotetrapeptides and cyclopentapeptides. The foregoing methods may be used to produce conformationally constrained polypeptides that elicit an immune response against the said (alpha)C portion.

The invention also contemplates immuno-interactive fragments or variants of the invention that have been modified using ordinary molecular biological techniques so as to improve their resistance to proteolytic degradation or to optimize solubility properties or to render them more suitable as an immunogenic agent.

2.5. Methods of Preparing the Polypeptides of the Invention

Polypeptides of the inventions may be prepared by any suitable procedure known to those of skill in the art. For example, the polypeptides may be prepared by a procedure including the steps of:

(a) preparing a recombinant polynucleotide comprising a nucleotide sequence encoding an immuno-interactive fragment of the polypeptide set forth in SEQ ID NO: 2 or preferably the polypeptide set forth in any one or more of SEQ ID NO: 3, 4, 5, 6, 18, 19, 20, 21, 22, 23, 30, 31, 32, 35, 36, 37, 38, 39, 40, 55, 56, 57, 58, 59, 60, 68, 69, 70, 71, 72 and 73, or a variant or derivative of these, which nucleotide sequence is operably linked to a regulatory polynucleotide which typically comprises transcriptional and translational regulatory nucleic acid;

(b) introducing the recombinant polynucleotide into a suitable host cell;

(c) culturing the host cell to express recombinant polypeptide from said recombinant polynucleotide; and (d) isolating the recombinant polypeptide.

The recombinant polynucleotide preferably comprises either an expression vector that may be a self-replicating extra-chromosomal vector such as a plasmid, or a vector that integrates into a host genome.

The transcriptional and translational regulatory nucleic acid will generally be appropriate for the host cell used for expression. Numerous types of appropriate expression vectors and suitable regulatory sequences are known in the art for a variety of host cells.

Typically, the transcriptional and translational regulatory nucleic acid may include, but is not limited to, promoter sequences, leader or signal sequences, ribosomal binding sites, transcriptional start and stop sequences, translational start and termination sequences, and enhancer or activator sequences.

Constitutive or inducible promoters as known in the art are contemplated by the invention. The promoters may be either naturally occurring promoters, or hybrid promoters that combine elements of more than one promoter.

In a preferred embodiment, the expression vector contains a selectable marker gene to allow the selection of transformed host cells. Selection genes are well known in the art and will vary with the host cell used.

The expression vector may also include a fusion partner (typically provided by the expression vector) so that the recombinant polypeptide of the invention is expressed as a fusion polypeptide with said fusion partner. The main advantage of fusion partners is that they assist identification and/or purification of said fusion polypeptide.

In order to express said fusion polypeptide, it is necessary to ligate a polynucleotide according to the invention into the expression vector so that the translational reading frames of the fusion partner and the polynucleotide coincide.

Well known examples of fusion partners include, but are not limited to, glutathione-S-transferase (GST), Fc potion of human IgG, maltose binding protein (MBP) and hexahistidine (HIS6), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with (HIS6) fusion partners and the Pharmacia GST purification system.

Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion polypeptide of the invention, or for isolating cells which express the fusion polypeptide of the invention. Flow cytometric methods such as fluorescence activated cell sorting (FACS) are particularly useful in this latter application.

Preferably, the fusion partners also have protease cleavage sites, such as for Factor $X_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-Myc, influenza virus, hemagglutinin and FLAG™ tags.

The step of introducing into the host cell the recombinant polynucleotide may be effected by any suitable method including transfection, and transformation, the choice of which will be dependent on the host cell employed. Such methods are well known to those of skill in the art.

Recombinant polypeptides of the invention may be produced by culturing a host cell transformed with an expression vector containing nucleic acid encoding an immuno-interactive fragment, variant or derivative according to the invention. The conditions appropriate for protein expression will vary with the choice of expression vector and the host cell. This is easily ascertained by one skilled in the art through routine experimentation.

Suitable host cells for expression may be prokaryotic or eukaryotic. One preferred host cell for expression of a polypeptide according to the invention is a bacterium. The bacterium used may be *Escherichia coli*. Alternatively, the host cell may be an insect cell such as, for example, SF9 cells that may be utilized with a baculovirus expression system.

The recombinant protein may be conveniently prepared by a person skilled in the art using standard protocols as for example described in Sambrook, et al., Molecular Cloning, a Laboratory Manual (Cold Spring Harbor Press, 1989), in particular Sections 16 and 17; Ausubel et al., Current Protocols in Molecular Biology (John Wiley & Sons, Inc. 1994-1998), in particular Chapters 10 and 16; and Coligan et al., Current Protocols in Protein Science (John Wiley & Sons, Inc. 1995-1997), in particular Chapters 1, 5 and 6.

In some cases, the recombinant polypeptide may require refolding. Methods of refolding are well known to those of skill in the art.

Alternatively, the polypeptide fragments, variants or derivatives of the invention may be synthesized using solution synthesis or solid phase synthesis as described, for example, in Chapter 9 of Atherton and Shephard (supra).

3. Polynucleotides of the Invention 3.1. Polynucleotides Encoding Immuno-interactive Fragments of the Invention The invention further provides a polynucleotide that encodes an immuno-interactive fragment, variant or derivative as defined above. Suitably, the polynucleotide comprises a fragment of the full-length nucleic acid sequence encoding the (alpha)C portion of the human inhibin alpha-subunit which fragment encodes an immuno-interactive fragment according to the invention. In this regard, reference may be made to SEQ ID NO: 1, which corresponds to nucleotide 841 through nucleotide 1245 of the full-length human inhibin alpha-subunit mRNA as for example disclosed under Accession No. M13981 of the GenBank database (supra), and which encodes the (alpha)C portion of the human inhibin alpha-subunit.

Preferably, the polynucleotide comprises a nucleic acid sequence encoding a polypeptide according to any one or more of SEQ ID NOs: 3, 4, 5, 6, 18, 19, 20, 21, 22, 23, 30, 31, 32, 35, 36, 37, 38, 39, 40, 55, 56, 57, 58, 59, 60, 68, 69, 70, 71, 72 and 73. Conveniently, such polynucleotide can be obtained from SEQ ID NO: 1, which encodes the (alpha)C portion of the human inhibin alpha-subunit set forth in SEQ ID NO: 2.

3.2. Polynucleotides Variants

In general, polynucleotide variants according to the invention comprise regions that show at least 60%, more suitably at least 70%, preferably at least 80%, and most preferably at least 90% sequence identity over a reference polynucleotide sequence of identical size ("comparison window") or when compared to an aligned sequence in which the alignment is performed by a computer homology program known in the art. What constitutes suitable variants may be determined by conventional techniques. For example, a polynucleotide fragment of SEQ ID NO: 1 or a polynucleotide encoding a polypeptide according to any one or more of SEQ ID NOs: 3, 4, 5, 6, 18, 19, 20, 21, 22, 23, 30, 31, 32, 35, 36, 37, 38, 39, 40, 55, 56, 57, 58, 59, 60, 68, 69, 70, 71, 72 and 73 can be mutated using random mutagenesis (e.g., transposon mutagenesis), oligonucleotide-mediated (or site-directed) mutagenesis, PCR mutagenesis and cassette mutagenesis of an earlier prepared variant or non-variant version of an isolated natural promoter according to the invention.

Oligonucleotide-mediated mutagenesis is a preferred method for preparing nucleotide substitution variants of a polynucleotide of the invention. This technique is well known in the art as, for example, described by Adelman et al. (1983, DNA 2:183). Briefly, a polynucleotide fragment of SEQ ID NO: 1 or a polynucleotide encoding a polypeptide according to any one or more of SEQ ID NOs: 3, 4, 5, 6, 18, 19, 20, 21, 22, 23, 30, 31, 32, 35, 36, 37, 38, 39, 40, 55, 56, 57, 58, 59, 60, 68, 69, 70, 71, 72 and 73 is altered by hybridizing an oligonucleotide encoding the desired mutation to a template DNA, where the template is the single-stranded form of a plasmid or bacteriophage containing the unaltered or parent DNA sequence. After hybridization, a DNA polymerase is used to synthesize an entire second complementary strand of the template that will thus incorporate the oligonucleotide primer, and will code for the selected alteration in said parent DNA sequence.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule.

The DNA template can be generated by those vectors that are either derived from bacteriophage M13 vectors, or those vectors that contain a single-stranded phage origin of replication as described by Viera et al. (1987, Methods Enzymol. 153:3). Thus, the DNA that is to be mutated may be inserted into one of the vectors to generate single-stranded template. Production of single-stranded template is described, for example, in Sections 4.21-4.41 of Sambrook et al. (1989, supra).

Alternatively, the single-stranded template may be generated by denaturing double-stranded plasmid (or other DNA) using standard techniques.

For alteration of the native DNA sequence, the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the immuno-interactive fragment under test, and the other strand (the original template) encodes the native unaltered sequence of the immuno-interactive fragment under test. This heteroduplex molecule is then transformed into a suitable host cell, usually a prokaryote such as *E. coli*. After the cells are grown, they are plated onto agarose plates and screened using the oligonucleotide primer having a detectable label to identify the bacterial colonies having the mutated DNA. The resultant mutated DNA fragments are then cloned into suitable expression hosts such as *E. coli* using conventional technology and clones that retain the desired antigenic activity are detected. Where the clones have been derived using random mutagenesis techniques, positive clones would have to be sequenced in order to detect the mutation.

Alternatively, linker-scanning mutagenesis of DNA may be used to introduce clusters of point mutations throughout a sequence of interest that has been cloned into a plasmid vector. For example, reference may be made to Ausubel et al., supra, (in particular, Chapter 8.4) which describes a first protocol that uses complementary oligonucleotides and requires a unique restriction site adjacent to the region that is to be mutagenized. A nested series of deletion mutations is first generated in the region. A pair of complementary oligonucleotides is synthesized to fill in the gap in the sequence of interest between the linker at the deletion endpoint and the nearby restriction site. The linker sequence actually provides the desired clusters of point mutations as it is moved or "scanned" across the region by its position at the varied endpoints of the deletion mutation series. An alternate protocol is also described by Ausubel et al., supra, which makes use of site directed mutagenesis procedures to introduce small clusters of point mutations throughout the target region. Briefly, mutations are introduced into a sequence by annealing a synthetic oligonucleotide containing one or more mismatches to the sequence of interest cloned into a single-stranded M13 vector. This template is grown in an $E.\ coli$ $dut^-$ $ung^-$ strain, which allows the incorporation of uracil into the template strand. The oligonucleotide is annealed to the template and extended with T4 DNA polymerase to create a double-stranded heteroduplex. Finally, the heteroduplex is introduced into a wild-type $E.\ coli$ strain, which will prevent replication of the template strand due to the presence of apurinic sites (generated where uracil is incorporated), thereby resulting in plaques containing only mutated DNA.

Region-specific mutagenesis and directed mutagenesis using PCR may also be employed to construct polynucleotide variants according to the invention. In this regard, reference may be made, for example, to Ausubel et al., supra, in particular Chapters 8.2A and 8.5.

Alternatively, suitable polynucleotide sequence variants of the invention may be prepared according to the following procedure:

(a) creating primers which are optionally degenerate wherein each comprises a portion of a reference polynucleotide encoding a reference immuno-interactive fragment of the invention, preferably encoding the sequence set forth in any one or more of SEQ ID NO: 3, 4, 5, 6, 18, 19, 20, 21, 22, 23, 30, 31, 32, 35, 36, 37, 38, 39, 40, 55, 56, 57, 58, 59, 60, 68, 69, 70, 71, 72 and 73;

(b) obtaining a nucleic acid extract from a different mammal from which said reference polynucleotide is derived; and (c) using said primers to amplify, via nucleic acid amplification techniques, at least one amplification product from said nucleic acid extract, wherein said amplification product corresponds to a polynucleotide variant.

Suitable nucleic acid amplification techniques are well known to the skilled addressee, and include polymerase chain reaction (PCR) as for example described in Ausubel et al. (supra); strand displacement amplification (SDA) as for example described in U.S. Pat. No. 5,422,252; rolling circle replication (RCR) as for example described in Liu et al., (1996, J. Am. Chem. Soc. 118:1587-1594 and International application WO 92/01813) and Lizardi et al., (international Application WO 97/19193); nucleic acid sequence-based amplification (NASBA) as for example described by Sooknanan et al., (1994, Biotechniques 17:1077-1080); and Q-beta replicase amplification as for example described by Tyagi et al., (1996, Proc. Natl. Acad. Sci. USA 93:5395-5400).

Typically, polynucleotide variants that are substantially complementary to a reference polynucleotide are identified by blotting techniques that include a step whereby nucleic acids are immobilized on a matrix (preferably a synthetic membrane such as nitrocellulose), followed by a hybridization step, and a detection step. Southern blotting is used to identify a complementary DNA sequence; northern blotting is used to identify a complementary RNA sequence. Dot blotting and slot blotting can be used to identify complementary DNA/DNA, DNA/RNA or RNA/RNA polynucleotide sequences. Such techniques are well known by those skilled in the art, and have been described in Ausubel et al. (1994-1998, supra) at pages 2.9.1 through 2.9.20.

According to such methods, Southern blotting involves separating DNA molecules according to size by gel electrophoresis, transferring the size-separated DNA to a synthetic membrane, and hybridizing the membrane-bound DNA to a complementary nucleotide sequence labeled radioactively, enzymatically or fluorochromatically. In dot blotting and slot blotting, DNA samples are directly applied to a synthetic membrane prior to hybridization as above.

An alternative blotting step is used when identifying complementary polynucleotides in a cDNA or genomic DNA library, such as through the process of plaque or colony hybridization. A typical example of this procedure is described in Sambrook et al. ("Molecular Cloning, A Laboratory Manual", Cold Spring Harbour Press, 1989) Chapters 8-12.

Typically, the following general procedure can be used to determine hybridization conditions. Polynucleotides are blotted/transferred to a synthetic membrane, as described above. A reference polynucleotide such as a polynucleotide of the invention is labeled as described above, and the ability of this labeled polynucleotide to hybridize with an immobilized polynucleotide is analyzed.

A skilled addressee will recognize that a number of factors influence hybridization. The specific activity of radioactively labeled polynucleotide sequence should typically be greater than or equal to about 108 dpm/mg to provide a detectable signal. A radiolabeled nucleotide sequence of specific activity 108 to 109 dpm/mg can detect approximately 0.5 pg of DNA. It is well known in the art that sufficient DNA must be immobilized on the membrane to permit detection. It is desirable to have excess immobilized DNA, usually 10 micrograms. Adding an inert polymer such as 10% (w/v) dextran sulfate (MW 500,000) or polyethylene glycol 6000 during hybridization can also increase the sensitivity of hybridization (see Ausubel supra at 2.10.10).

To achieve meaningful results from hybridization between a polynucleotide immobilized on a membrane and a labeled polynucleotide, a sufficient amount of the labeled polynucleotide must be hybridized to the immobilized polynucleotide following washing. Washing ensures that the labeled polynucleotide is hybridized only to the immobilized polynucleotide with a desired degree of complementarity to the labeled polynucleotide.

It will be understood that polynucleotide variants according to the invention will hybridize to a reference polynucleotide under at least low stringency conditions. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NAHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature.

Suitably, the polynucleotide variants hybridize to a reference polynucleotide under at least medium stringency conditions. Medium stringency conditions include and encompass from at least about 16% v/v to at least about 30% v/v formamide and from at least about 0.5 M to at least about 0.9 M salt for hybridization at 42° C., and at least about 0.5 M to at least about 0.9 M salt for washing at 42° C. Medium stringency conditions also may include 1% Bovine Serum Albumin (BSA), 1 mM EDTA, 0.5 M NAHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 42° C.

Preferably, the polynucleotide variants hybridize to a reference polynucleotide under high stringency conditions. High stringency conditions include and encompass from at least about 31% v/v to at least about 50% v/v formamide and from at least about 0.01 M to at least about 0.15 M salt for hybridization at 42° C., and at least about 0.01 M to at least about 0.15 M salt for washing at 42° C. High stringency conditions also may include 1% BSA, 1 MM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C.

Other stringent conditions are well known in the art. A skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, washing is carried out at T=69.3+0.41 (G+C) % −12° C. However, the $T_m$ of a duplex DNA decreases by 1° C. with every increase of 1% in the number of mismatched base pairs.

In a preferred hybridization procedure, a membrane (e.g., a nitrocellulose membrane or a nylon membrane) containing immobilized DNA is hybridized overnight at 42° C. in a hybridization buffer (50% deionized formamide, 5×SSC, 5× Denhardt's solution (0.1% Ficoll, 0.1% polyvinylpyrollidone and 0.1% bovine serum albumin), 0.1% SDS and 200 mg/mL denatured salmon sperm DNA) containing labeled probe. The membrane is then subjected to two sequential medium stringency washes (i.e., 2×SSC/0.1% SDS for 15 min at 45° C., followed by 2×SSC/0.1% SDS for 15 min at 50° C.), followed by two sequential high stringency washes (i.e., 0.2×SSC/0.1% SDS for 12 min at 55° C. followed by 0.2×SSC and 0.1% SDS solution for 12 min).

Methods for detecting a labeled polynucleotide hybridized to an immobilized polynucleotide are well known to practitioners in the art. Such methods include autoradiography, phosphorimaging, and chemiluminescent, fluorescent and calorimetric detection.

4. Antigen-binding Molecules

The invention also contemplates antigen-binding molecules against the aforementioned fragments, variants and derivatives. Antigen-binding molecules contemplated by the present invention include monoclonal antibodies. Such antibodies may be produced using the standard method as described, for example, by Kohler and Milstein (1975, Nature 256, 495-497), or by more recent modifications thereof as described, for example, in Coligan et al., (1991, supra) by immortalizing spleen or other antibody producing cells derived from a production species which has been inoculated with one or more of the immuno-interactive fragments, variants or derivatives of the invention. Exemplary methods for producing monoclonal antibodies, which are immuno-interactive with the polypeptides of the invention, are described in Groome et al. (1994, In "Inhibin and inhibin-related proteins," Burger, Ed. Frontiers in Endocrinology, Vol. 3 Ares Serono Symposia) and in Groome et al. (1994, Clin. Endocrinol. 40:717-723).

The invention also contemplates as antigen-binding molecules Fv, Fab, Fab' and F(ab')$_2$ immunoglobulin fragments.

Alternatively, the antigen-binding molecule may comprise a synthetic stabilized Fv fragment. Exemplary fragments of this type include single chain Fv fragments (sFv, frequently termed scFv) in which a peptide linker is used to bridge the N terminus or C terminus of a $V_H$ domain with the C terminus or N-terminus, respectively, of a $V_L$ domain. ScFv lack all constant parts of whole antibodies and are not able to activate complement. Suitable peptide linkers for joining the $V_H$ and $V_L$ domains are those which allow the $V_H$ and $V_L$ domains to fold into a single polypeptide chain having an antigen binding site with a three dimensional structure similar to that of the antigen binding site of a whole antibody from which the Fv fragment is derived. Linkers having the desired properties may be obtained by the method disclosed in U.S. Pat. No. 4,946,778. However, in some cases a linker is absent. ScFvs may be prepared, for example, in accordance with methods outlined in Krebber et al. (1997, J. Immunol. Meth. 201(1): 35-55). Alternatively, they may be prepared by methods described in U.S. Pat. No. 5,091,513, European Patent No. 239,400 or the articles by Winter and Milstein (1991, Nature 349:293) and Plückthun et al (1996, In Antibody engineering: A practical approach, pp. 203-252).

Alternatively, the synthetic stabilized Fv fragment comprises a disulfide stabilized Fv (dsFv) in which cysteine residues are introduced into the $V_H$ and $V_L$ domains such that in the fully folded Fv molecule the two residues will form a disulfide bond therebetween. Suitable methods of producing dsFv are described for example in (Glockscuther et al., Biochemistry 29:1363-1367; Reiter et al., 1994, J. Biol. Chem. 269:18327-18331; Reiter et al., 1994, Biochemistry 33:5451-5459; Reiter et al., 1994, Cancer Res. 54:2714-2718; Webber et al., 1995, Mol. Immunol. 32:249-258).

Also contemplated as antigen-binding molecules are single variable region domains (termed dAbs) as for example disclosed in (Ward et al., 1989, Nature 341:544-546; Hamers-Casterman et al., 1993, Nature 363:446-448; Davies et al., 1994, FEBS Lett. 339:285-290).

Alternatively, the antigen-binding molecule may comprise a "minibody." In this regard, minibodies are small versions of whole antibodies, which encode in a single chain the essential elements of a whole antibody. Suitably, the minibody is comprised of the $V_H$ and $V_L$ domains of a native antibody fused to the hinge region and CH3 domain of the immunoglobulin molecule as, for example, disclosed in U.S. Pat. No. 5,837,821.

In an alternate embodiment, the antigen binding molecule may comprise non-immunoglobulin derived, protein frameworks. For example, reference may be made to (Ku et al., 1995, Proc. Natl. Acad. Sci. USA 92:652-6556) which discloses a four-helix bundle protein cytochrome b562 having two loops randomized to create complementarity determining regions (CDRs), which have been selected for antigen binding.

The antigen-binding molecule may be multivalent (i.e., having more than one antigen binding site). Such multivalent molecules may be specific for one or more antigens. Multivalent molecules of this type may be prepared by dimerization of two antibody fragments through a cysteinyl-containing peptide as, for example disclosed by (Adams et al., 1993, Cancer Res. 53:4026-4034; Cumber et al., 1992, J. Immunol. 149:120-126). Alternatively, dimerization may be facilitated by fusion of the antibody fragments to amphiphilic helices that naturally dimerize (Plunckthun, 1992, Biochemistry 31:1579-1584), or by use of domains (such as leucine zippers jun and fos) that preferentially heterodimerize (Kostelny et al., 1992, J. Immunol. 148:1547-1553).

In an alternate embodiment, the multivalent molecule may comprise a multivalent single chain antibody (multi-scFv) comprising at least two scFvs linked together by a peptide linker. In this regard, non-covalently or covalently linked scFv dimers termed "diabodies" may be used. Multi-scFvs may be bispecific or greater depending on the number of scFvs employed having different antigen-binding specificities. Multi-scFvs may be prepared for example by methods disclosed in U.S. Pat. No. 5,892,020.

The monoclonal antibodies, immunoglobulin fragments and immunoglobulin-like fragments described above are particularly preferred as antigen-binding molecules to replace polyclonal antibodies used in current two-site assays for inhibin A, B and Pro-(alpha)C, as well as inhibin alpha subunit assays.

The antigen-binding molecules of the invention may be used for affinity chromatography in isolating a natural or recombinant mammalian inhibin and in particular, a natural or recombinant mammalian inhibin alpha subunit. For example reference may be made to immunoaffinity chromatographic procedures described in Chapter 9.5 of Coligan et al., (Current Protocols in Immunology, (John Wiley & Sons, Inc, 1991-1997).

The antigen-binding molecules can be used to screen expression libraries for variant polypeptides of the invention as described herein. They can also be used to detect mammalian inhibin, preferably mammalian inhibin alpha subunit, as described hereinafter. In addition, the antigen-binding molecules of the invention can be used to treat a condition associated with aberrant concentrations of the (alpha)C portion of a mammalian inhibin alpha subunit in a biological sample, as described hereinafter.

5. Detection of Mammalian Inhibin

The presence or absence of a mammalian inhibin in a patient may be determined by isolating the biological sample from the patient, contacting the biological sample with an antigen-binding molecule as described in Section 4, and detecting the presence of a complex comprising the said antigen-binding molecule and the mammalian inhibin. In this regard, the antigen-binding molecule may be species-specific, that is specific to an inhibin of a particular mammal. Preferably, the antigen-binding molecule detects inhibin from a plurality of mammalian species.

There is also provided a method of diagnosing a condition associated with an aberrant concentration of a mammalian inhibin in a biological sample of a patient. The method comprises contacting the biological sample with an antigen-binding molecule as described in Section 4, measuring the concentration of a complex comprising the said antigen-binding molecule and the mammalian inhibin in said contacted sample, and relating said measured complex concentration to the concentration of mammalian inhibin in said sample, wherein the presence of said aberrant concentration is indicative of said condition. Suitably, the condition is a cancer, more preferably an endocrine-related cancer. Preferably, the endocrine-related cancer is a cancer of a reproductive organ. In a preferred embodiment, the endocrine-related cancer is ovarian cancer. Alternatively, the endocrine-related cancer may be breast, uterine, endometrial, prostate or testicular cancer.

Any suitable technique for determining formation of the complex may be used. For example, an antigen-binding molecule according to the invention, having a reporter molecule associated therewith may be utilized in immunoassays. Such immunoassays include, but are not limited to, radioimmunoassays (RIAs), enzyme-linked immunosorbent assays (ELISAS) and immunochromatographic techniques (ICTs), Western blotting which are well known those of skill in the art. For example, reference may be made to "Current Protocols in Immunology" (1994, supra) which discloses a variety of immunoassays that may be used in accordance with the present invention. Immunoassays may include competitive assays as understood in the art or as for example described infra. It will be understood that the present invention encompasses qualitative and quantitative immunoassays.

Suitable immunoassay techniques are described for example in U.S. Pat. Nos. 4,016,043; 4,424,279; and 4,018,653. These include both single-site and two-site assays of the non-competitive types, as well as the traditional competitive binding assays. These assays also include direct binding of a labeled antigen-binding molecule to a target antigen.

Two site assays are particularly favored for use in the present invention. A number of variations of these assays exist all of which are intended to be encompassed by the present invention. Briefly, in a typical forward assay, an unlabelled antigen-binding molecule such as an unlabelled antibody is immobilized on a solid substrate and the sample to be tested brought into contact with the bound molecule. After a suitable period of incubation, for a period of time sufficient to allow formation of an antibody-antigen complex, another antigen-binding molecule, suitably a second antibody specific to the antigen, labeled with a reporter molecule capable of producing a detectable signal is then added and incubated, allowing time sufficient for the formation of another complex of antibody-antigen-labeled antibody. Any unreacted material is washed away and the presence of the antigen is determined by observation of a signal produced by the reporter molecule. The results may be either qualitative, by simple observation of the visible signal, or may be quantitated by comparing with a control sample containing known amounts of antigen. Variations on the forward assay include a simultaneous assay, in which both sample and labeled antibody are added simultaneously to the bound antibody. These techniques are well known to those skilled in the art, including minor variations as will be readily apparent. In accordance with the present invention, the sample is one that might contain an antigen including serum, whole blood, and plasma or lymph fluid. The sample is, therefore, generally a circulatory sample comprising circulatory fluid.

In the typical forward assay, a first antibody having specificity for the antigen or antigenic parts thereof is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well known in the art and generally consist of cross-linking covalently binding or physically adsorbing, the polymer-antibody complex is washed in preparation for the test sample. An aliquot of the sample to be tested is then added to the solid phase complex and incubated for a period of time sufficient and under suitable conditions to allow binding of any antigen present to the antibody. Following the incubation period, the antigen-antibody complex is washed and dried and incubated with a second antibody specific for a portion of the antigen. The second antibody has generally a reporter molecule associated therewith that is used to indicate the binding of the second antibody to the antigen. The amount of labeled antibody that binds, as determined by the associated reporter molecule, is proportional to the amount of antigen bound to the immobilized first antibody.

An alternative method involves immobilizing the antigen in the biological sample and then exposing the immobilized antigen to specific antibody that may or may not be labeled with a reporter molecule. Depending on the amount of target and the strength of the reporter molecule signal, a bound antigen may be detectable by direct labeling with the antibody. Alternatively, a second labeled antibody, specific to the first antibody is exposed to the target-first antibody complex to form a target-first antibody-second antibody tertiary complex. The complex is detected by the signal emitted by the reporter molecule.

From the foregoing, it will be appreciated that the reporter molecule associated with the antigen-binding molecule may include the following:

(a) direct attachment of the reporter molecule to the antigen-binding molecule;

(b) indirect attachment of the reporter molecule to the antigen-binding molecule; i.e., attachment of the reporter molecule to another assay reagent which subsequently binds to the antigen-binding molecule; and (c) attachment to a subsequent reaction product of the antigen-binding molecule.

The reporter molecule may be selected from a group including a chromogen, a catalyst, an enzyme, a fluorochrome, a chemiluminescent molecule, a lanthamide ion such as Europium (Eu34), a radioisotope and a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes suitable for use as reporter molecules is disclosed in U.S. Pat. Nos. 4,366,241; 4,843,000; and 4,849,338. Suitable enzymes useful in the present invention include alkaline phosphatase, horseradish peroxidase, luciferase, beta-galactosidase, glucose oxidase, lysozyme, malate dehydrogenase and the like. The enzymes may be used alone or in combination with a second enzyme that is in solution.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al. (International Publication WO 93/06121). Reference also may be made to the fluorochromes described in U.S. Pat. Nos. 5,573,909 (Singer et al.) and 5,326,692 (Brinkley et al.). Alternatively, reference may be made to the fluorochromes described in U.S. Pat. Nos. 5,227,487; 5,274,113; 5,405,975; 5,433,896; 5,442,045; 5,451,663; 5,453,517; 5,459,276; 5,516,864; 5,648,270; and 5,723,218.

In the case of an enzyme immunoassay, an enzyme is conjugated to the second antibody, generally by means of glutaraldehyde or periodate. As will be readily recognized, however, a wide variety of different conjugation techniques exist which are readily available to the skilled artisan. The substrates to be used with the specific enzymes are generally chosen for the production of, upon hydrolysis by the corresponding enzyme, a detectable color change. Examples of suitable enzymes include those described supra. It is also possible to employ fluorogenic substrates, which yield a fluorescent product rather than the chromogenic substrates noted above. In all cases, the enzyme-labeled antibody is added to the first antibody-antigen complex, allowed to bind, and then the excess reagent washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample.

Alternately, fluorescent compounds, such as fluorescein, rhodamine and the lanthamide, europium (Eu), may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. The fluorescent-labeled antibody is allowed to bind to the first antibody-antigen complex. After washing off the unbound reagent, the remaining tertiary complex is then exposed to light of an appropriate wavelength. The fluorescence observed indicates the presence of the antigen of interest. Immunofluorometric assays (IFMA) are well established in the art and are particularly useful for the present method. However, other reporter molecules, such as radioisotope, chemiluminescent or bioluminescent molecules may also be employed.

In a particularly preferred embodiment, the condition for diagnosis is ovarian cancer. In this instance, a combination immunoenzymemetric assay is preferably employed which makes use of an antigen-binding molecule as described for example in Section 4 together with an antigen-binding molecule against an ovarian cancer antigen such as CA125. For example, the CA125 or other antigen is immobilized on a solid support such as magnetic beads with a first antibody and then a second antibody labeled with an enzyme is allowed to bind to the CA125 or to the other antigen. After appropriate washing, the complex is incubated in the presence of a fluorogenic substrate. The amount of enzyme-labeled antibody that binds to the solid support is directly proportional to the concentration of CA125 or other antigen in the test sample. A standard curve may also be constructed and concentrations of CA125 or other antigens may be determined in an unknown sample using the standard curve. An exemplary protocol for performing this assay is described, for example, by Robertson et al (1999, Clin. Chem. 45:651-658).

Inhibin may be determined in a similar manner to CA125 or to the other antigen. Particularly useful assays include an (alpha)C IFMA, a Pro(alpha)C ELISA or a RIA. For example, in a preferred embodiment, an antigen-binding molecule to the Pro region of the alpha subunit is used to immobilize inhibin molecules containing this region to a solid support such as a microtiter plate, magnetic bead or other suitable surface. A second antigen-binding molecule as described in Section 4 and labeled with an enzyme such as alkaline phosphatase is used to detect bound inhibin. A similar assay is described in Groome et al., (1996, supra) with the exception that an antigen-binding molecule directed to the carboxyl terminal end of the alpha subunit ((alpha)C) was used instead of an antigen-binding molecule according to the invention.

The antigen-binding molecules of the invention can also be applied to the conventional (alpha)C IFMA. For example, these antigen-binding molecules may be used for the capture antibody in place of the caprylic acid/ammonium polyclonal antibody raised against human inhibin (alpha)C subunit fusion protein (Forage et al., 1987, In Inhibin: Non-Steroidal Regulation of Follicle Stimulating Hormone Secretion, Burger et al., Eds., Raven Press. Serono Symposium 42:89-103). The subject antigen-binding molecules can also be used as the reporter or labeled antigen-binding molecule in place of the immunopurified sheep polyclonal antibody raised against human inhibin (alpha)C subunit fusion protein (Forage et al., 1987, supra; Robertson et al., 1997, supra).

6. Compositions

The invention also encompasses a composition for use in eliciting an immune response in a mammal which response includes production of elements that specifically bind the (alpha)C portion of a mammalian inhibin alpha subunit, comprising an immuno-interactive fragment, variant or derivative as broadly described above ("immunogenic agents"), together with a pharmaceutically acceptable carrier. Optionally, said composition further comprises an adjuvant.

A further feature of the invention is the use of the antigen-binding molecules of the invention ("therapeutic agents") as actives, together with a pharmaceutically acceptable carrier, in a composition for protecting or treating patients against a condition associated with aberrant concentrations of a mammalian inhibin in a mammal.

Depending upon the particular route of administration, a variety of pharmaceutically acceptable carriers, well known in the art, may be used. These carriers may be selected from sugars, starches, cellulose and its derivatives, malt, gelatin, talc, calcium sulfate, vegetable oils, synthetic oils, polyols, alginic acid, phosphate buffered solutions, emulsifiers, isotonic saline, and pyrogen-free water.

Any suitable route of administration may be employed for providing a mammal or a patient with a composition of the invention. For example, oral, rectal, parenteral, sublingual, buccal, intravenous, intra-articular, intramuscular, intra-dermal, subcutaneous, inhalational, intraocular, intraperitoneal, intracerebroventricular, transdermal and the like may be employed. Intra-muscular and subcutaneous injection is appropriate, for example, for administration of immunogenic compositions, vaccines and DNA vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of an immunogenic or a therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by using other polymer matrices, liposomes and/or microspheres.

Compositions suitable for oral or parenteral administration may be presented as discrete units such as capsules, sachets or tablets each containing a pre-determined amount of one or more immunogenic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more immunogenic agents as described above with the carrier which constitutes one or more necessary ingredients. In general, the compositions are prepared by uniformly and intimately admixing the immunogenic agents of the invention with liquid carriers or finely divided solid carriers or both, and then, if necessary, shaping the product into the desired presentation.

The above compositions may be administered in a manner compatible with the dosage formulation, and in such amount as is therapeutically effective or immunogenically effective as the case may be. In this regard, the dose of immunogenic agent administered to a mammal should be sufficient to elicit an immune response that includes the production of elements that specifically bind to the (alpha)C potion of a mammalian inhibin alpha-subunit.

Alternatively, the dose of therapeutic agent administered to a patient should be sufficient to effect a beneficial response in the patient over time such as a reduction in the level of a mammalian inhibin or to ameliorate the condition to be treated. The quantity of the therapeutic agent(s) to be administered may depend on the subject to be treated inclusive of the age, sex, weight and general health condition thereof. In this regard, precise amounts of the therapeutic agent(s) for administration will depend on the judgement of the practitioner. In determining the effective amount of the therapeutic agent to be administered in the treatment or prophylaxis of the condition associated with aberrant levels of a mammalian inhibin, the physician may evaluate circulating plasma levels, progression of the condition, and the production of anti-inhibin antibodies.

In any event, those of skill in the art may readily determine suitable dosages of the immunogenic and therapeutic agents of the invention. Such dosages may be in the order of nanograms to milligrams of the immunogenic agents of the invention.

An immunogenic agent according to the invention can be mixed, conjugated or fused with other antigens, including B or T cell epitopes of other antigens. In addition, it can be conjugated to a carrier as described below.

When an haptenic peptide is used (i.e., a peptide which reacts with cognate antibodies, but cannot itself elicit an immune response), it can be conjugated with an immunogenic carrier. Useful carriers are well known in the art and include for example: thyroglobulin; albumins such as human serum albumin; toxins, toxoids or any mutant cross-reactive material (CRM) of the toxin from tetanus, diphtheria, pertussis, Pseudomonas, *E. coli*, Staphylococcus, and Streptococcus; polyamino acids such as poly(lysine:glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immunogenic protein may be used. For example, an haptenic peptide can be coupled to a T cell epitope of a bacterial toxin, toxoid or CRM. In this regard, reference may be made to U.S. Pat. No. 5,785,973.

The immunogenic compositions may include an adjuvant as is well known in the art. Suitable adjuvants include, but are not limited to: surface active substances such as bexadecylamine, octadecylamine, octadecyl amino acid esters, lysolecithin, dimethyldioctadecylammonium bromide, N,N-dioctadecyl-N', N'bis(2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; lymphokines, and QuilA.

In a further embodiment, a polynucleotide of the invention may be used as an immunogenic composition in the form of a "naked DNA" composition as is known in the art. For example, an expression vector of the invention may be introduced into a mammal, where it causes production of an immuno-interactive fragment according to the invention in vivo, against which the host mounts an immune response as for example described in Barry et al. (1995, Nature 377:632-635).

7. Detection Kits

The present invention also provides kits for the detection of a mammalian inhibin in a biological sample. These will contain one or more agents described above depending upon the nature of the test method employed. In this regard, the kits may include one or more of an immuno-interactive fragment, variant, derivative, or antigen-binding molecule according to the invention. The kits may also optionally include appropriate reagents for detection of labels, positive and negative controls, washing solutions, dilution buffers and the like.

In order that the invention may be readily understood and put into practical effect, particular preferred embodiments will now be described by way of the following non-limiting examples.

EXAMPLES

Example 1

Inhibin Immunofluorometric Assay (IFMA)

This IFMA is used in the measurement of inhibin in serum from women with ovarian cancer and is presented at this juncture as a reference to the following procedures. The IFMA is a sandwich antibody assay in 96-well microtiter plates. The capture antiserum is As #128 and the labeled antiserum As #41, both raised in sheep to the alpha subunit of human inhibin. Sheep As #128 was also boosted with human recombinant 30-kDa inhibin. The microtiter plates were coated with a caprylic acid IgG cut of antiserum #128. Inhibin standard and serum samples were added and incubated for 2 hours at room temperature. A biotinylated antiserum (As #41) which has been immunopurified by absorption to a column of bovine (alpha)C subunit fusion protein (as previously described, Robertson et al., 1997, supra) followed by elution with a glycine (pH 2.5) buffer, was added to bind to the antibody-bound inhibin (2-hour incubation at room temperature). Fluorescently (Eu) labeled-streptavidin that has a high affinity for biotin is added (30 minutes at room temperature) and the Eu-bound streptavidin is counted in a time-resolved fluorimeter. The Eu measured is proportional to the inhibin bound by the two antisera.

Example 2

Studies Involving Inhibin Alpha Subunit Peptides

The human inhibin alpha subunit sequence can be divided into three parts, Pro (amino acids 19-61), (alpha)N (62-232) and (alpha)C (233-366, see Mason et al., 1986, Biochem. Biophys. Res. Commun. 135:957-964 for sequence data) based on the known presence of proteolytic cleavage sites and known isolation of these parts from biological samples. Since the (alpha)C subunit is common to the vast majority of inhibin forms, it has been used as the antigen for producing antisera (#128 and #41) in sheep.

To identify the various epitopes, 31 overlapping peptides (14 amino acids long) of the human (alpha)C subunit were synthesized by Chiron Mimotopes, Clayton, Vic (the sequences are presented in Table 1) with an N-terminal biotin attached. These peptides were then tested for their interaction with As #41 and #128 in the following assays in comparison with the native inhibin molecule (human recombinant 30 kDa inhibin (hr-inhibin)).

Assay 1: Solid Phase Assay

This assay is a broad screen of the binding of the 31 biotinylated peptides to As #41 and #128 as recommended by Chiron Mimotopes.

Methods

The biotinylated peptides were initially bound to streptavidin-coated 96-well plates (2 hours at room temperature), antiserum #41 or #128 was then added (2 hours room temperature) to bind to the peptides. Detection of antiserum binding was assessed by a further incubation with an anti-ovine IgG serum labeled with the enzyme, horseradish peroxidase. The enzyme activity was assessed by conversion of a colorless substrate to a colored product that is detected in a spectrophotometer. The enzyme activity measured was proportional to the extent of the binding of the peptides.

Results

The results, as presented in FIG. 1, show that As #41 and As #128 bind in general to 4 peptide regions designated Region I (peptides 3-7), II(11-15), III (16-23) and IV (27-33). Region II peptides were of limited solubility and as such the results were treated with caution particularly at high peptide concentrations. Peptides from this region showed limited responses or no response in any of the assays.

Assay 2: RIA Using Antisera #41, #128 and Rabbit Antiserum #1989 as Reference

This assay was used to determine which peptides compete with iodinated 30 kDa inhibin for As #41, #128 and #1989 (used in the original inhibin RIA, Lapphorn et al., 1989, supra) in a RIA format. This assay identifies those peptides that bind to inhibin-binding antibodies in the antiserum and provides a stricter affinity and specificity assessment in identifying the appropriate epitopes than that found with Assay 1. The competition between peptide and hr-inhibin (used as the standard) was assessed from their $ED_{50}$ values.

Methods

The RIA consisted of the competition of iodinated inhibin and either hr-inhibin reference preparation, individual peptides or pools from the 4 peptide regions, with As #41, #128 and in some instances, As #1989. The peptides/inhibin/iodinated inhibin and antisera (at a prescribed dilution) were incubated overnight at 4° C. using standard methodologies. The antibody-bound iodinated inhibin was immunoprecipitated with the addition of an anti-sheep IgG serum raised in goats and the radioactivity was measured in a gamma counter. The concentration of peptide that gives a 50% fall in binding of iodinated inhibin ($ED_{50}$) was determined and this value was used to give a measure of the affinity of the peptide for the antiserum.

Results

Figure 2:
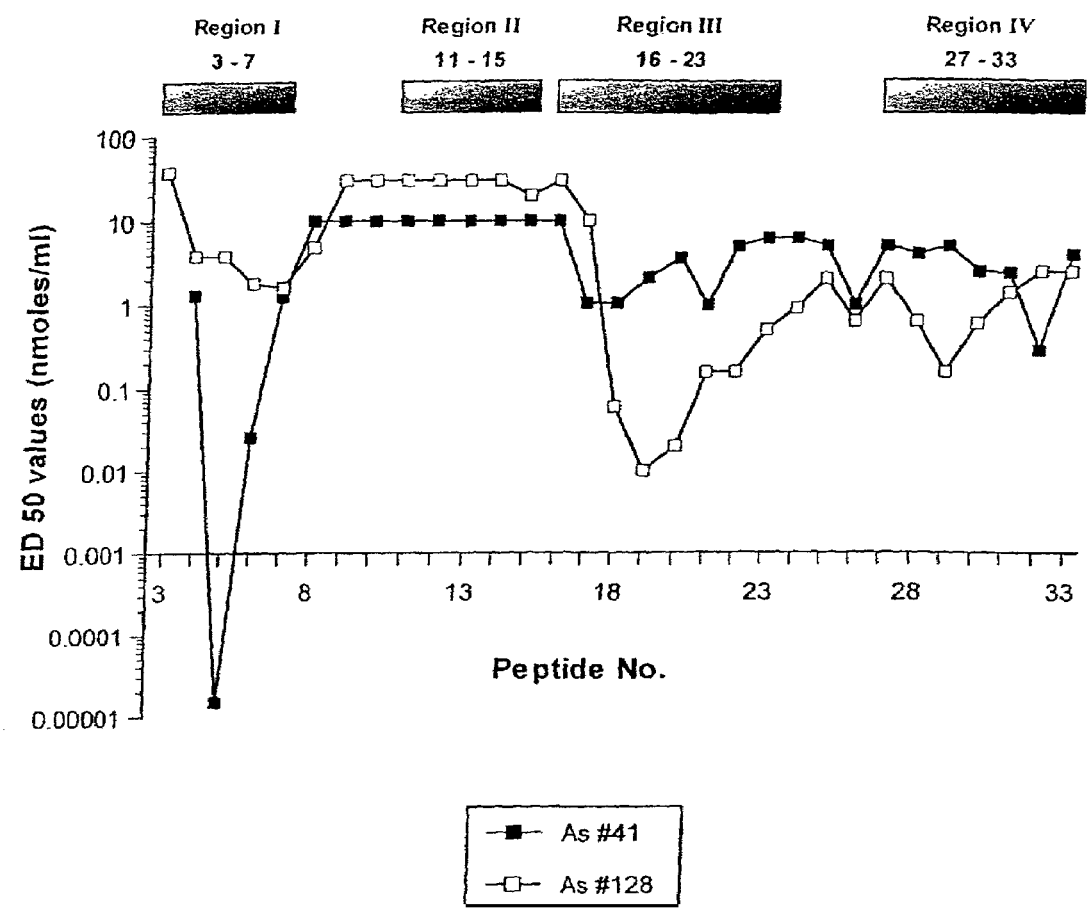
FIG. 2 is a graph showing $ED_{50}$ values obtained for the 31 biotinylated peptides with As #41 and As #128 in the RIA format. The RIA provides a measure of both specificity and affinity of the binding of the biotinylated peptides to the antisera.

The results presented in FIG. 2 and Table 2 indicate that peptides from Region 1, Region 3, and Region 4 show the lowest $ED_{50}$, indicating that these antisera bind peptides from these regions with the highest affinity. As #41 showed a different range of affinities in comparison with As #128 with peptides #4-6 and #30-33 showing the highest cross-reactions. As #128 showed cross-reaction with peptides #18-20 and #28-30. With regard to As #1989, the only peptide to show competition with hr-inhibin was peptide #30 ($ED_{50}$<0.01 mmole/mL) with the others showing little or no evidence of competition ($ED_{50}$>2.5 mmole/mL) (Table 2).

Assay 3: Competitive 2-site Assay

This assay was developed to establish the relative importance of the individual peptides and peptide pools (identified as epitopes in Assays 1 and 2) in the sandwich antibody format used in the IFMA with As #128 as capture antibody and As #41 as detection antibody. Two approaches (a and b) were considered, Approach (a) explores the cross-reaction of peptides with inhibin for the immobilized As #128 while Approach (b) assesses their cross-reaction with inhibin for As #41.

Approach (a). The biotinylated peptide pools and/or individual peptides at various concentrations, in combination with a fixed concentration of hr-inhibin, were incubated for 2 hours with As #128-coated plates. The plates were then washed to remove any unbound material. Iodinated As #41 was then added to bind to the bound hr-inhibin, the plates washed and the bound radioactivity was measured in a gamma counter. The counts measured were proportional to the amount of hr-inhibin bound to both antisera. The possibility that a peptide contained two epitopes capable of linking As #128 and #41 was assessed in the absence of added hr-inhibin.

Results

Figure 3:
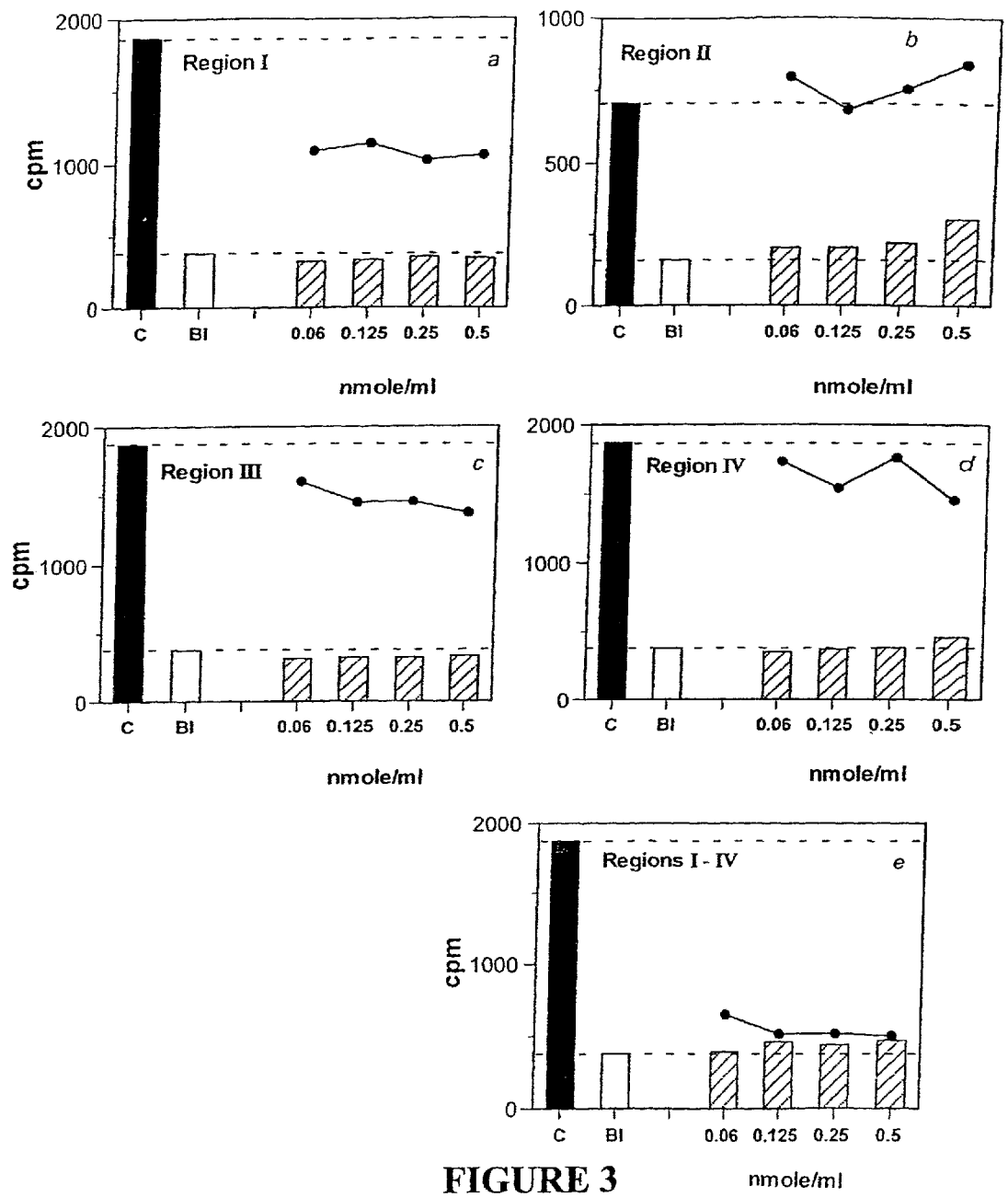
FIG. 3 shows nine histograms relating to a competitive 2-site assay. These histograms show the inhibition of inhibin binding by biotinylated peptide pools from Regions I-IV, I, IIII, IV, peptide #5, #20 and #30 with As #128. This assay design enables the assessment of the epitopes identified in the various antisera in a two-antibody sandwich assay design. Legend: C, control; Bl, blank; hatched areas, peptide alone.

The results, presented in FIG. 3, show that the binding of Region I (FIG. 3a) and III (FIG. 3c) peptide pools and possibly Region IV (FIG. 3d) peptide pools with As #128 partially competed (10-50%) with hr-inhibin while Region II pool showed no competition. The combination of Region I-IV peptide pools totally suppressed binding (FIG. 3e). Individual peptides (peptide #5, #20 and #30, FIGS. 3f-h) showed a similar range of binding to that seen with the corresponding Region peptide pools. These results suggest that the main epitopes on As #128 are positioned around peptides #5, #20 and #30.

Approach (b). In this approach, the competition of peptides with the As #41 antiserum using the sandwich antibody format was assessed. Hr-Inhibin was initially incubated with the As #128 coated wells for 1 hour at room temperature. The biotinylated peptide pools and/or individual peptides were incubated together with iodinated As #41 for 1 hour and then added to the inhibin bound As #128 coated plates and incubated for 2 hours at room temperature. Plates were then washed to remove any unbound material and the resulting activity was measured in the gamma counter.

Results

Figure 4:
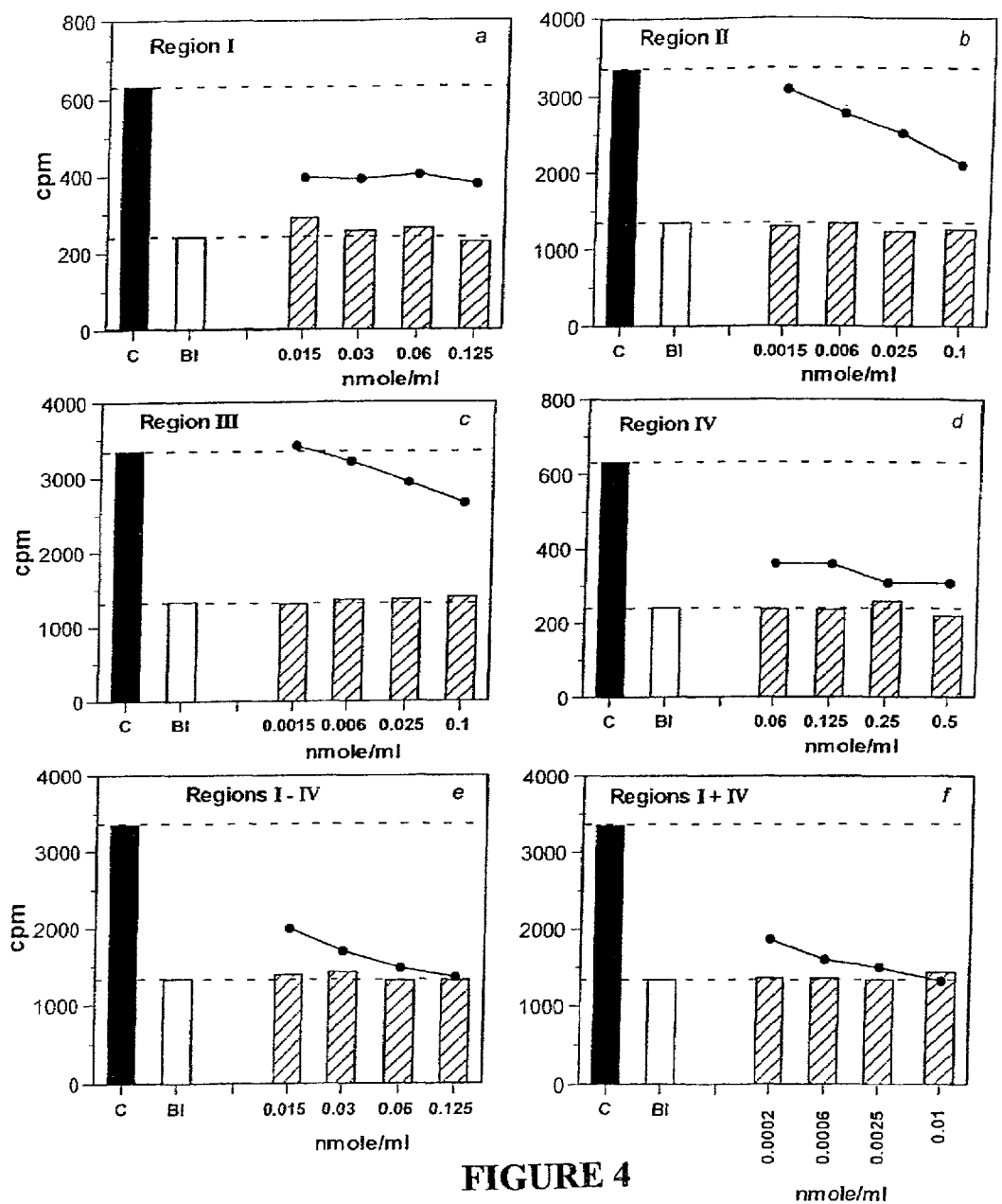
FIG. 4 shows ten histograms relating to a competitive 2-site assay. These histograms show the inhibition of inhibin binding by peptide pools from Regions I-IV, I, IIII, IV, peptide #5, #20 and #30 with As #41. Legend: C, control; Bl, blank; hatched areas peptide alone.

The results, presented in FIG. 4, showed that the binding of Region I (FIG. 4a) and IV (FIG. 4d) peptide pools to As #41 partially blocked the binding of As #41 to the inhibin-As#128 complex while the combination of Regions I–IV or I+IV peptide pools totally suppressed binding (FIG. 4e,f). Both Region pools II and III have limited effects at high doses. Further data showed that individually, peptide #5 and #30 each contributed 50% (FIG. 4g,i) while the combination of peptide #5 and either peptide #29 (not shown) or #30 (FIG. 4j) competed totally with inhibin for As #41. These results indicate that the main epitopes on As #41 are located within peptides #5 and #29-30.

Example 3

Studies Utilizing Non-biotinylated Peptide #5, #20 and #30

The above studies (Example 2) were undertaken using biotinylated peptides of approximate mass. The studies presented in Example 2 identified 3 main peptides, #5, #20 and #30 as likely epitopes. A second phase study was undertaken with these peptides synthesized in mg amounts with 95% purity by Chiron Mimotopes with an $NH_2$-Cys-Ser-Lys-Lys-Gly-amino terminal-spacer and a more precise mass determination. The following studies were undertaken using these 3 peptides.

RIA

This methodology consisted of determining the $ED_{50}$ of the peptide in the RIA using iodinated human recombinant inhibin as tracer with either As #41, As #128 or As #1989 and graded doses of either hr-inhibin or peptide as described in Example 2.

As seen in Table 3, based on the $ED_{50}$ values, peptide #5 cross-reacted strongly with hr-inhibin for As #41 while the other peptides were less reactive.

Two-site Assay Design

The above RIA design is not directly comparable to the sandwich antibody design used in the IFMA as the RIA design is based on competition of peptide with inhibin. On the other hand, the IFMA design is based on the total amount of inhibin bound which is a combination of both antibody affinity and concentration. In order to establish to what extent epitopes to these peptides contribute to the overall IFMA, the following two-site assay designs were used.

(i) Peptides #5, #20 and #30 (0, 0.1-1 micromolar) were incubated with the As #128 coated plate for 1.5 hours at RT and the wells washed. The highest dose of peptide used was saturating.

(ii) Hr-Inhibin was then added as a saturating or near saturating dose to the As #128 coated plate and incubated for 2 hours at room temperature and the plate washed.

(iii) Biotinylated As #41 was added to the above wells and incubated for 2 hours at RT. Plates were then washed and counted.

Figure 5:
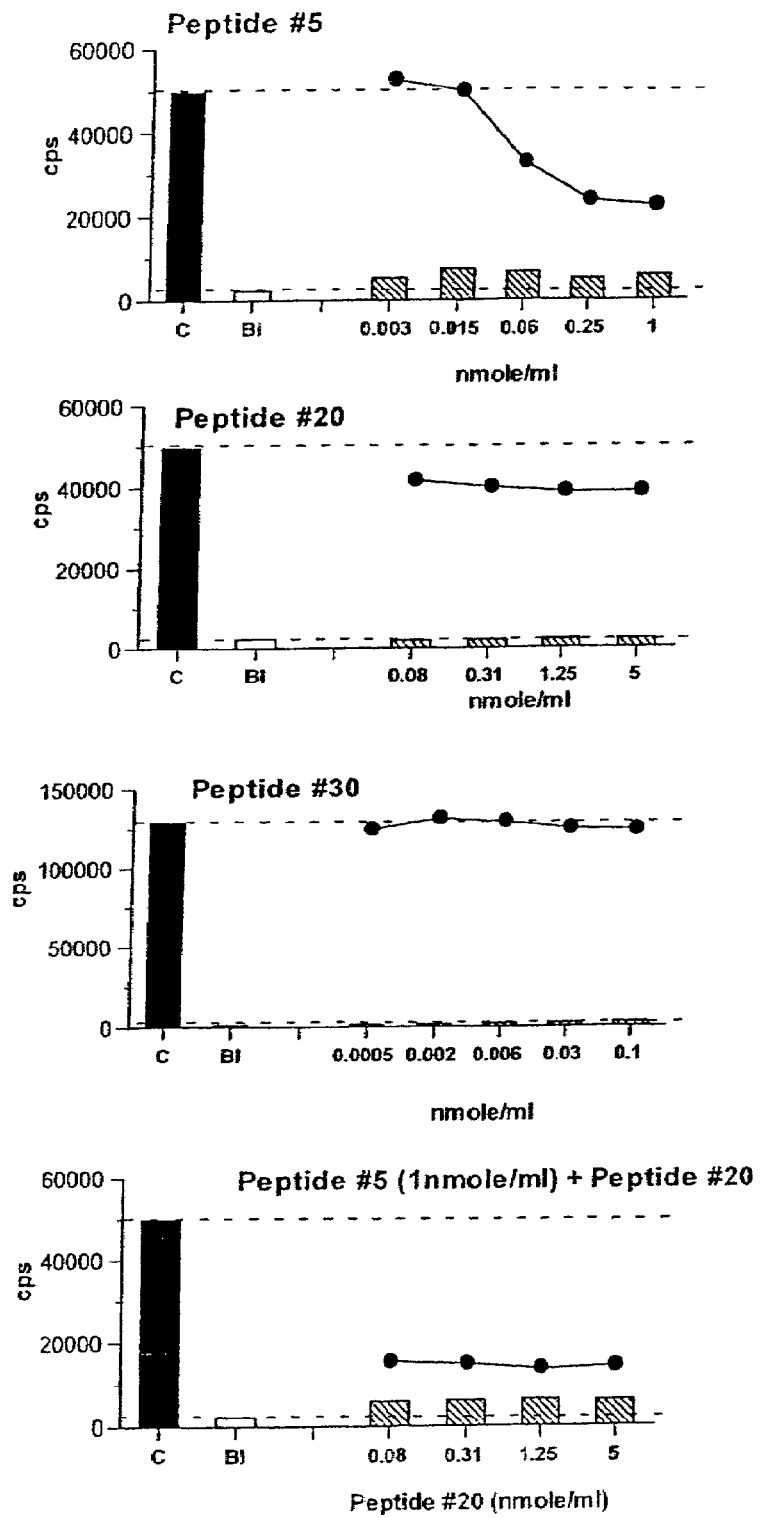
FIG. 5 shows four histograms relating to a competitive 2-site assay. These histograms show the inhibition of inhibin binding by peptide #5, #20 and #29 with As #128. Legend: C, control; Bl, blank, hatched areas peptide alone.

The contribution of each of the peptides to the overall binding was then assessed. As seen in Table 4 and FIG. 5, peptide #5 and #20 showed a graded suppression in binding (65% and 23% respectively) with As #128 while a combination of peptide #5 and #20 gave 83% suppression. Peptide #30 showed no suppression at all.

Figure 6:
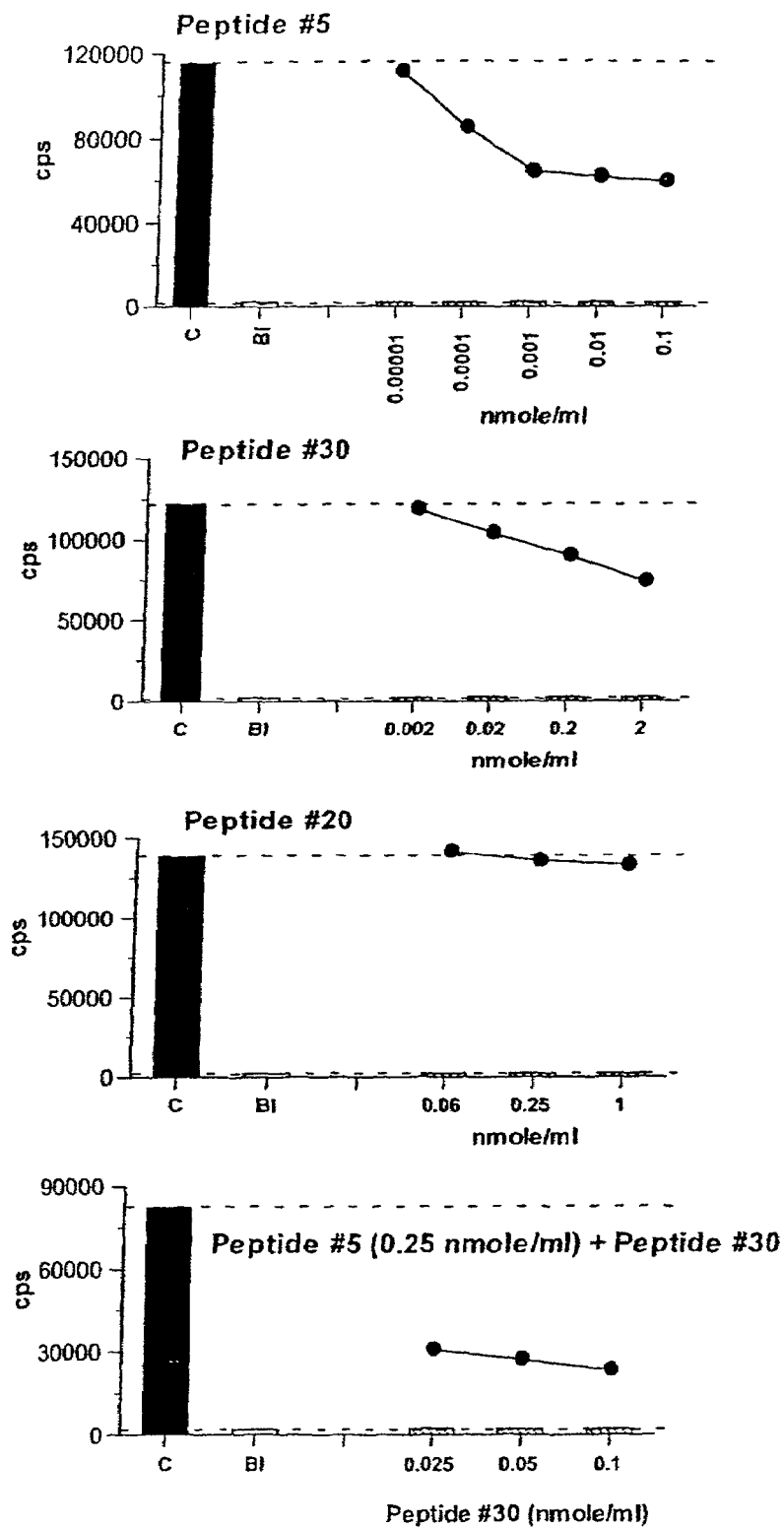
FIG. 6 shows four histograms relating to a competitive 2-site assay. These histograms show the inhibition of inhibin binding by peptide #5, #20 and #29 with As #41. Legend: C, control; Bl, blank; hatched areas peptide alone.

(iv) In a variation to the above design, biotinylated #41 was pre-incubated with peptide (0.1-1.0 micromolar) for 1.5 hours at room temperature and then added to the As #128 coated plate pre-bound with inhibin as for (i)-(iii). As seen in FIG. 6, peptide #5 showed 50% inhibition, while peptide #30 showed 25-30% but not saturating. Combination of peptide #5 and #30 led to 74% decrease. Peptide #20 showed no inhibition.

Figure 7:
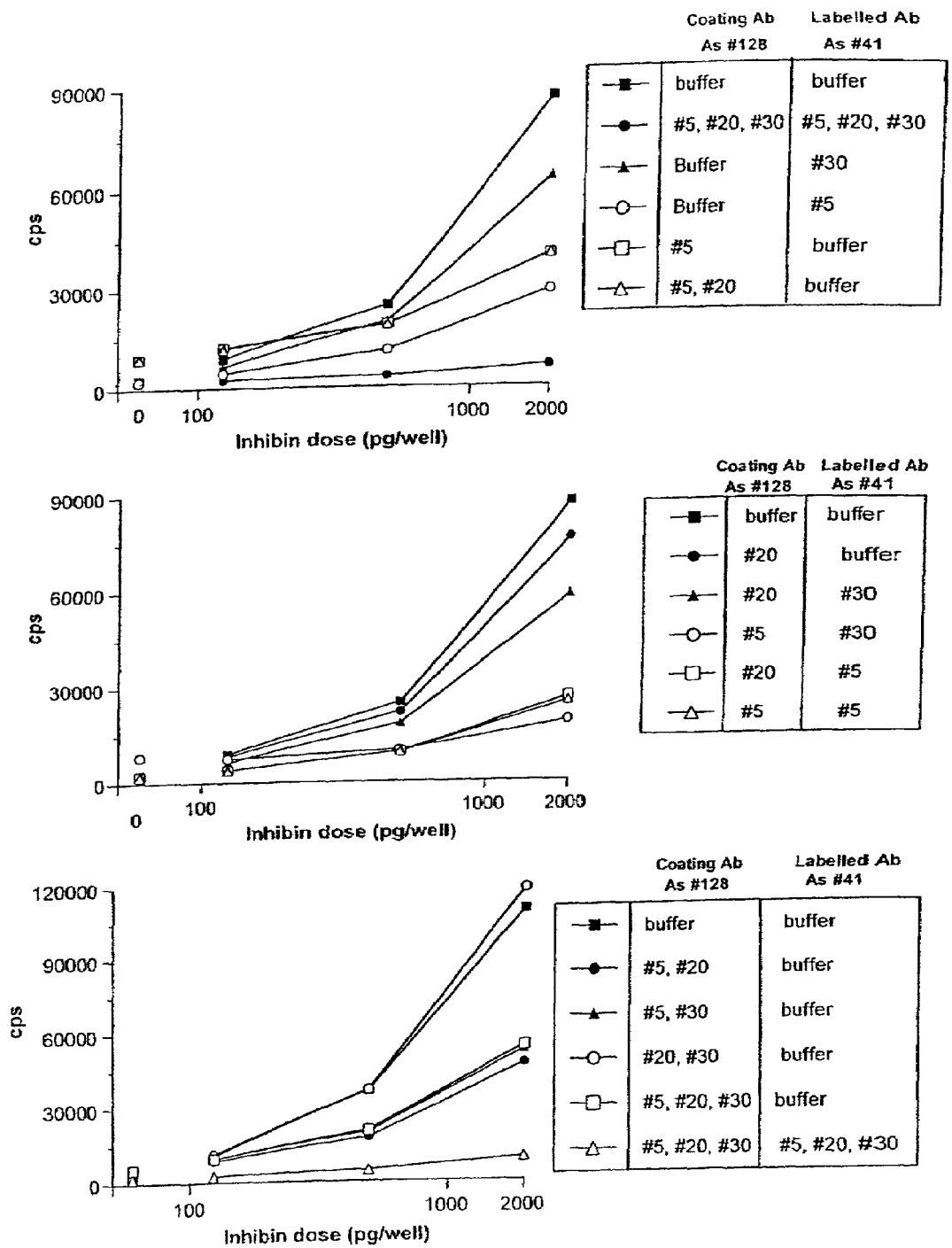
FIG. 7 depicts three graphs showing the effect of immunoabsorption with peptides #5, #20 and #30 of antisera #41 and #128 in the (alpha)C IFMA. Quantitative aspects are presented in Table 5.
Figure 8:
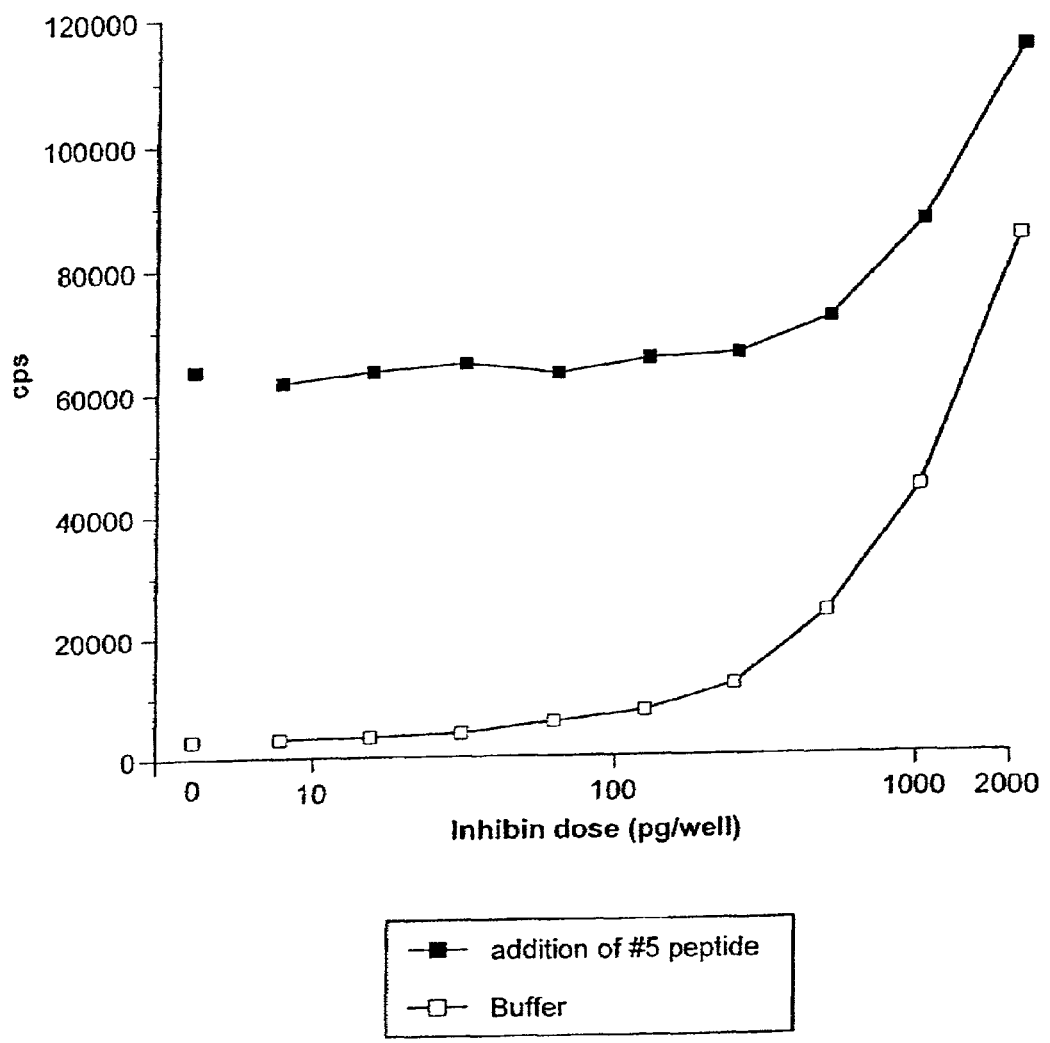
FIG. 8 depicts a graph showing the effect of immunoabsorption of antiserum #41 used as both coating and labeled antibody with peptide #5 in an IFMA format. In the absence of added inhibin, the blank (0 inhibin dose) showed considerable binding indicating that the #5 peptide is a bridge between the coated and labeled #41 antibody and thus probably containing two binding sites.
Figure 9:
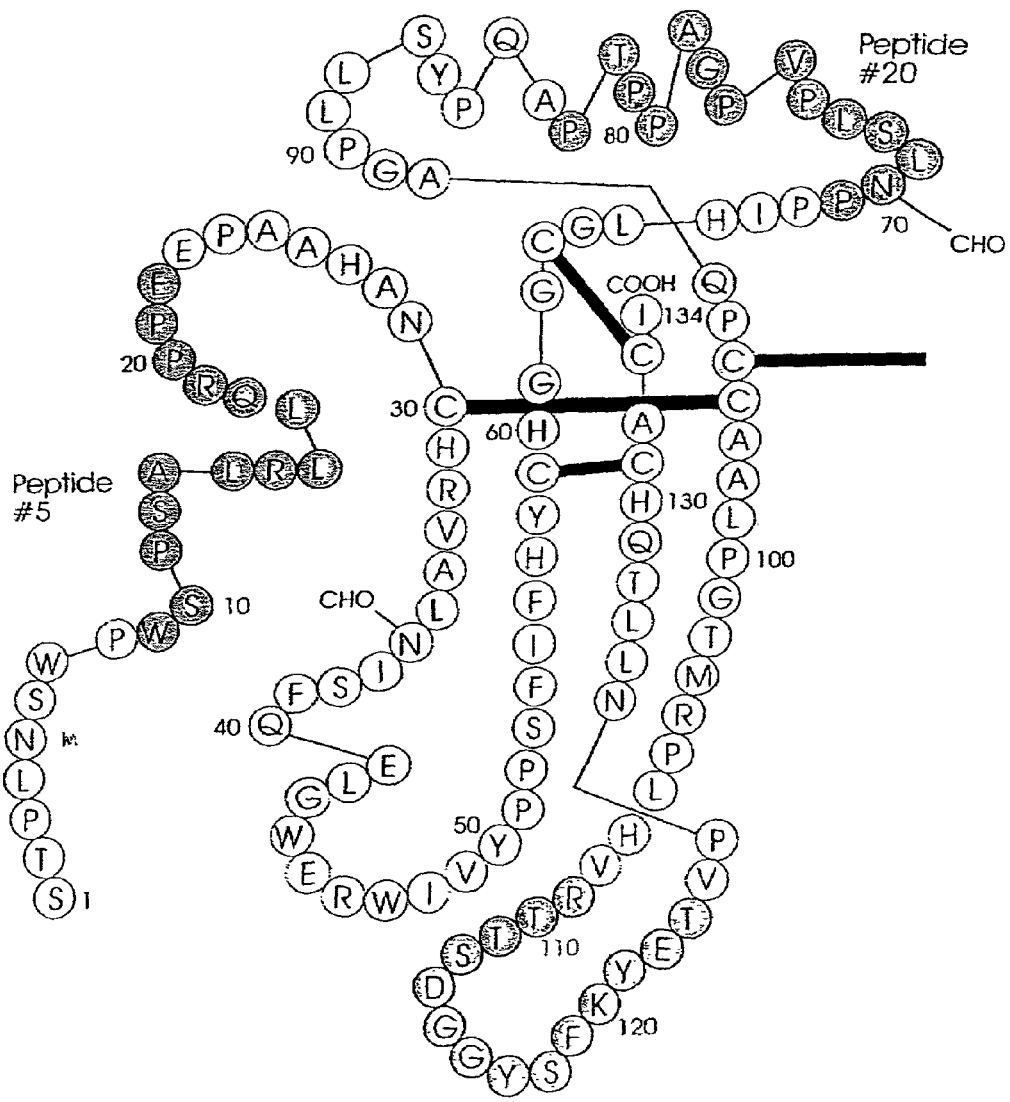
FIG. 9 illustrates a putative three-dimensional structure of the carboxyl-terminal region of the inhibin alpha subunit as adapted from the three dimensional structure of TGF(beta). The amino acid positions of peptides #5, #20 and #30 are presented as shaded areas.

As another approach, the competition of combinations of peptides at a maximum saturating dose was assessed in the IFMA (FIGS. 7-9). It can be seen in FIG. 7 that the addition of peptides #5, #20 and #30 to the IFMA resulted in an almost total suppression in binding while pre-absorption with one peptide for example resulted in a lesser suppression. This suppression in binding provides a measure of the contribution of that particular epitope to the assay.

The following conclusions were drawn from Table 5 and FIGS. 7-9.

(1) Peptides #5, #20 and #30 are responsible for the majority (95%) of inhibin binding in the (alpha)C IFMA. In relation to the capture antibody (#128), peptide #5 is the most important although peptide #20 does make a small contribution. This contribution is more evident when the #5 peptide epitope is absorbed out with #5 peptide. Peptide #5 and peptide #30 regions are the primary epitopes on As #41.

(2) In an alternative sandwich antibody assay design where As#41 was used as both as coating and labeled antibody, the addition of peptide #5 to both the coating and labeled antibodies in the absence of inhibin resulted in significant binding (FIG. 8). These results suggest that there are two epitopes on peptide #5 (termed epitopes 5a and 5b) and that the two antibodies in As #41 can bind this 14-amino acid residue peptide simultaneously. It has not been established if the same antibodies are present in As #128.

(3) Absorption of As #128 by peptides #5, #20 and #30 resulted in partial suppression (55%) only indicating that there is another major epitope in As #128 which has not been identified (FIG. 7c). This conclusion is despite the observation (FIG. 4) that the combination of peptides from all 4 regions resulted in total suppression. It is unclear where this epitope is located within the inhibin (alpha)C subunit.

(4) Why is it that peptides #20 and #30 show a low cross-reaction with inhibin in the RIA yet show a relatively high contribution in the IFMA compared to peptide #5? One explanation is that compared with peptide #5, epitopes #20 and #30 are present at high binding site concentrations although with low affinity that favors the IFM.

Example 4

Production of Mouse Anti-inhibin (alpha)C Monoclonal Antibodies

Mouse monoclonal antibodies (designated PO# Mabs) were raised against a recombinant inhibin (alpha)C subunit-beta galactosidase fusion protein based on the hybridoma procedure as outlined in Groome et al. (1994, In "Inhibin and inhibin-related proteins," Burger, Ed., Frontiers in Endocrinology, Vol. 3, Ares Serono Symposia). The hybridomas were screened and cloned against both recombinant human inhibin A and pro-(alpha)C (a fragment of the alpha subunit of inhibin).

Characterization of Mabs

Antibody Affinity

The affinity of the various Mabs for inhibin based on $ED_{25}$ values was determined by radioimmunoassay according to assay 2 of Example 2 using iodinated human inhibin A as tracer. Mabs (at an antibody dilution to give 50% maximum iodinated inhibin binding, normally 1:500-1:2000 dilutions of the original culture medium) were incubated with iodinated human recombinant inhibin A in the presence of human recombinant inhibin A overnight at room temperature. The iodinated inhibin-antibody complex was precipitated by an anti-mouse IgG serum and the radioactivity determined in a gamma counter.

Specificity

The binding of the 41 biotinylated peptides as set forth in Table 7 (peptide set 2) to the mouse monoclonal antibodies (PO# series) was assessed as follows:

a) Assay 1 (solid phase assay). The assay was undertaken as outlined in assay 1 of Example 2. Biotinylated peptides (24 micromoles/L) were initially bound to streptavidin-coated plates. Mab (at an appropriate dilution to give a detectable response, 1:1000, 1:10000 dilution of the culture medium) was then added and incubated for 1.5 hr. The amount of bound Mab was determined using horseradish peroxidase-bound anti-mouse IgG serum and enzyme activity detected at 450-630 nm using an ELISA plate reader.

b) Assay 2 (radioimmunoassay, RIA) using iodinated human inhibin A as tracer. Mabs (at an appropriate dilution, see above) were incubated with iodinated human recombinant inhibin in the presence of biotinylated peptides (0.8 and 0.08 micromoles/L final concentration) overnight at room temperature.

Results

The affinity of the PO# Mabs as determined from RIA competition studies with inhibin is presented in Tables 8 and 9.

The specificity of the Mabs based on binding of the biotinylated peptides either in a solid phase binding assay or by RIA is also presented in Tables 8 and 9.

Discussion

As seen in Table 10, the Mabs, based on their specificity to the biotinylated peptides, are directed to three epitopic regions seen with the ovine polyclonal antisera mentioned above.

a) PO#6, PO#22 are immuno-interactive with peptides 2-7 of Set 2, which correspond to peptide #5 of Table 1.

b) PO#12, PO#14 are immuno-interactive with peptides 22-27 of Set 2, which correspond to peptides #21-23 of Set 1. This region (i.e., the region defined by peptides 22-27) appears to be distinct from epitope #20 (peptides #18-20 of Set 1) although there is potential overlap of sequence. Perusal of FIGS. 1, 2 and Table 2 indicates that significant binding with As #128 is present in this region of the inhibin sequence, although less than the nearby region corresponding to peptides #18-20 (epitope #20). It is prudent to conclude that epitope #20 may comprise two epitopes, most likely #18-20 Set 1 (#19-21 Set 2, designated 20a) and #21-23 Set 1 (#22-27 Set 2, designated 20b) and that PO#12, PO#14 are immuno-interactive with the latter.

c) Mabs PO#9, PO#19, PO#23, PO#25, PO#26 are immuno-interactive with peptides 35-40 Set 2 or 30-32 Set 1. These Mabs are comparable with peptide #30 shown in Table 1.

Example 5

Development of Alpha Subunit ELISAs

An ELISA system using 96-well microtiter plates was developed consisting of one alpha subunit antibody as coating antibody and an alkaline phosphatase-linked second antibody as label. The alkaline phosphatase activity was amplified using an ELISA amplification kit (Gibco, Life Technologies, Rockville Md., USA). The plate was initially coated with monoclonal antibody at 2 micrograms/well in 0.1 M bicarbonate buffer pH 9.4 overnight at room temperature and blocked with 50 mM TRIS/HCl, 1% bovine serum albumin (BSA) pH 7.4.

ELISA Procedure

The ELISAs in application to non-serum samples consisted of 100 microliters sample or recombinant human (rh) inhibin A standard (provided by National Institute of Biological Standards and Control, Potters Bar, Herts, UK) in assay buffer (100 mM TRIS/HCl, 154 mM NaCl, 5% Triton-X-100, 10% BSA pH, 7.5) and 100 microliters assay buffer. In the assay of serum, the inhibin A standard (100 microliters) was diluted in assay buffer. Inhibin-free serum (100 microliters) was also added to make a total well volume of 200 microliters. The inhibin-free serum was obtained by incubating serum with an immobilized inhibin alpha subunit antibody. Repeated extractions resulted in no detectable inhibin immunoactivity as determined by the alpha subunit ELISAs. Serum samples were initially boiled in the presence of SDS (2% final concentration) and diluted 1:1 with assay buffer before adding 100 microliters to the wells. The inhibin-free serum and the SDS boiling steps were included to offset any potential matrix effects of serum known to affect other inhibin ELISAs although the need for these specific steps had not been assessed.

The plate was incubated with shaking overnight at room temperature. The wells were washed, and alkaline phosphatase (AP)-linked antibody added, incubated with shaking for 3 hours at room temperature and washed again. The substrate (NADPH, Gibco) was added and the plate incubated for 2 hours with shaking at room temperature. The amplifying enzymes (alcohol dehydrogenase and diaphorase, Gibco) were added and incubated for 5-15 min until appropriate color had developed. The plate was read at 490/630 nm on an ELISA plate reader.

Example 6

Characteristics of the Inhibin Alpha ELISAs

Figure 10A:
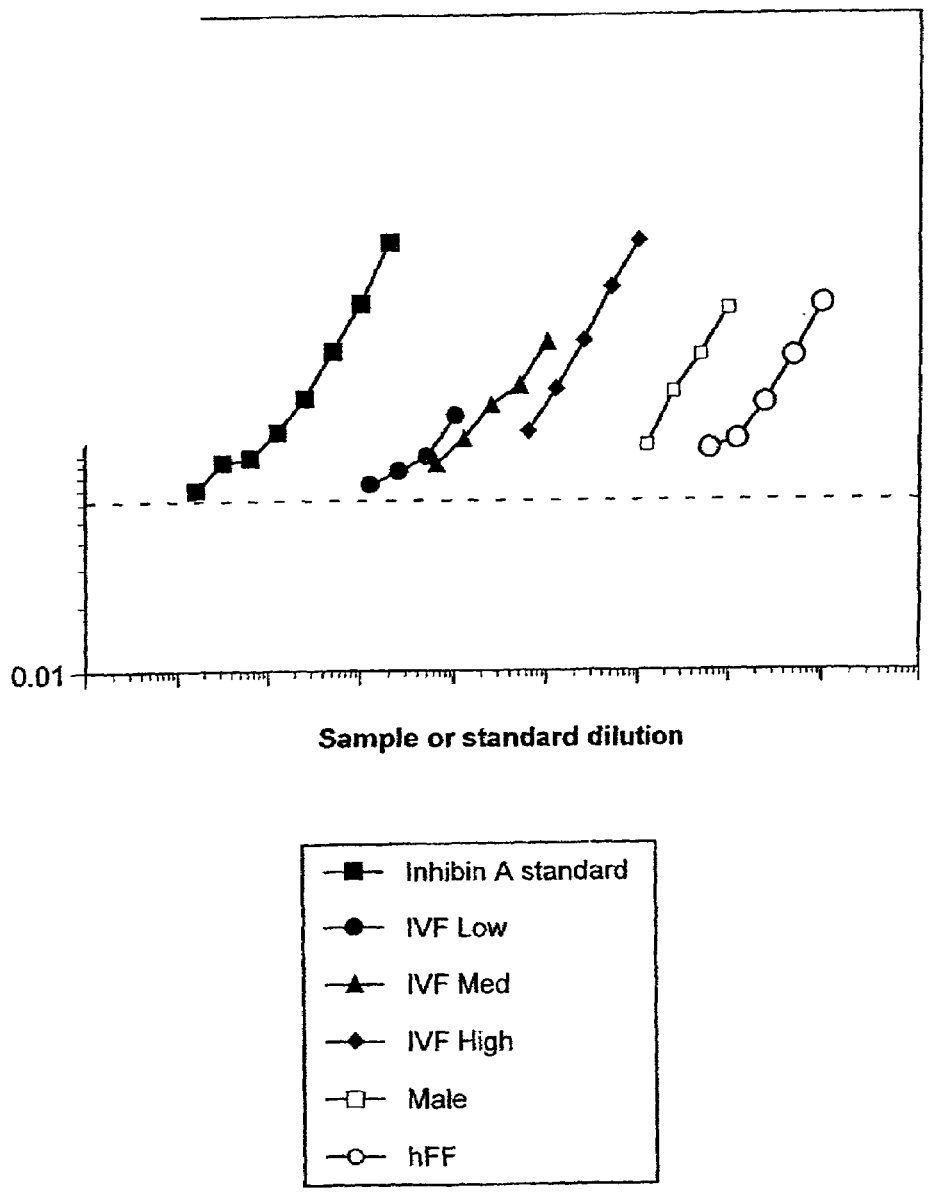
FIG. 10A shows inhibin alpha ELISA dose response curves of inhibin A standard (1.5-100 picograms/well), various serum pools (3-50 microliters/well) and human follicular fluid (hFF, XXX) using the monoclonal antibodies PO#14 and R1. Legend.
Figure 10B:
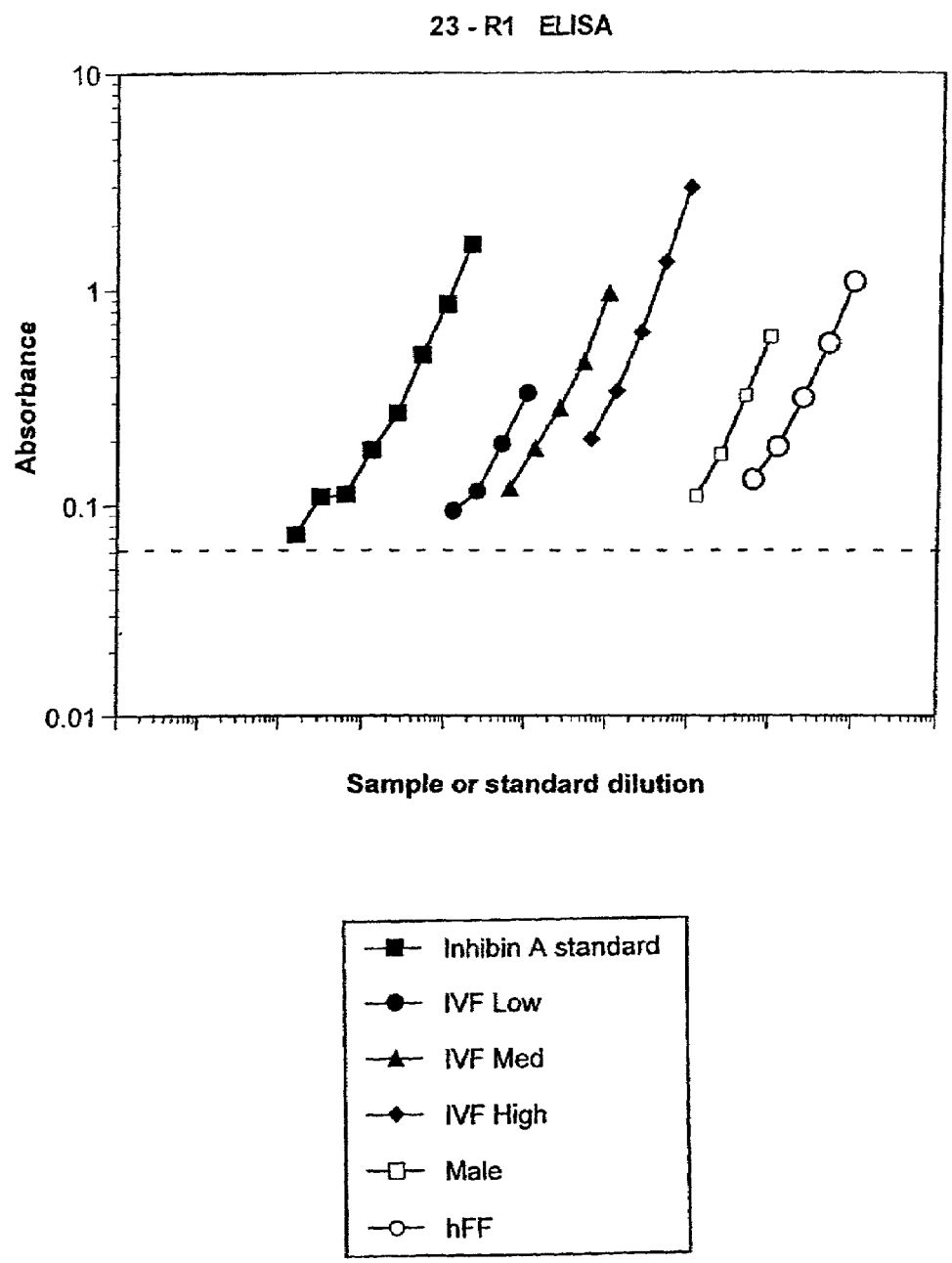
FIG. 10B shows inhibin alpha ELISA dose response curves of inhibin A standard (1.5-100 picograms/well), various serum pools (3-50 microliters/well) and human follicular fluid (hFF, XXX) using the monoclonal antibodies PO#23 and R1.

Inhibin alpha ELISAs were developed using PO#14 and PO#23 Mabs as coating antibody and AP-R1 as detection antibody. Serial dilutions of standard and serum or human follicular fluid gave parallel responses in the various assays (FIGS. 10a, 10b). The characteristics of these assays are outlined in Table 11. The sensitivity of the ELISAs based on inhibin values calculated 2 standard deviations above the assay blank ranged from 6-15 pg/mL serum. The levels of inhibin alpha in normal sera and human follicular fluid using these assays are presented in Table 13.

The specificity of the ELISAs was assessed by determining the cross-reaction of inhibin-related proteins in the various ELISAs. As seen in Table 12, in comparison with the inhibin A standard, inhibin B and the alpha subunit fragment, Pro-(alpha)C, showed different degrees of cross-reaction in the various ELISAs.

Figure 10C:
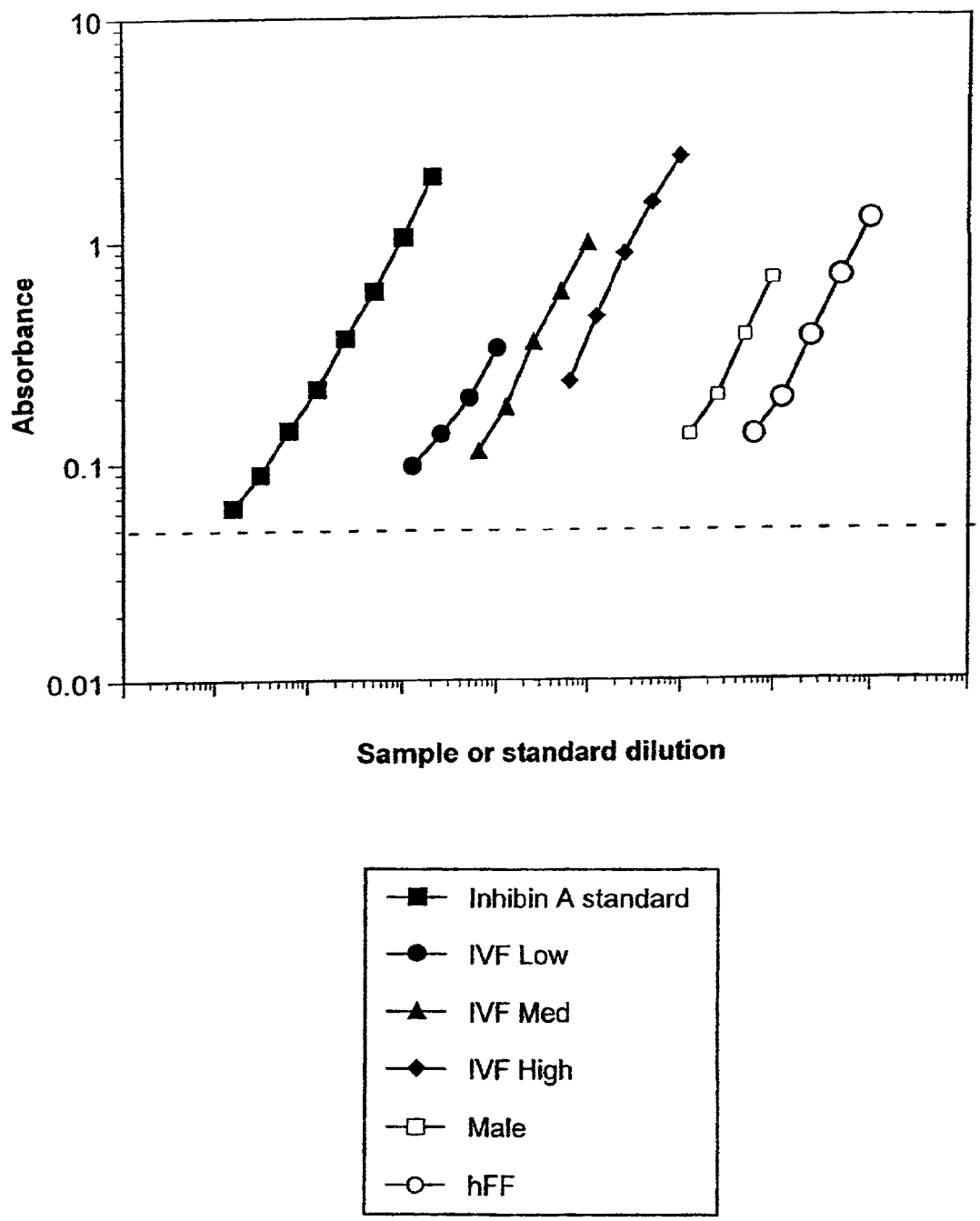
FIG. 10C shows inhibin alpha ELI SA dose response curves of inhibin A standard (1.5-100 picograms/well), various serum pools (3-50 microliters/well) and human follicular fluid (hFF, XXX) using the monoclonal antibodies PO# 14, PO#23 and R1.

As a result of an initial characterization of these ELISAs (see below), a combination of PO#14+PO#23 as coating antibodies and AP linked-R1 antibody as tracer was also assessed and its characteristics are also presented in Table 11 and 12 and FIG. 10c.

Example 7

Specificity of the Inhibin Alpha ELISAs

It was unclear from the above characterization studies what was the specificity of the various ELISA assays in terms of their ability to detect inhibin alpha subunit monomer and (alpha)(beta) subunit dimers. To characterize further, IVF serum, male serum and serum from women with ovarian granulosa cell tumours and mucinous tumours were fractionated by a combined immunoaffinity, Prep-PAGE/electroelution procedure similar to that published previously by our group (Robertson et al., 1996, J. Clin. Endocrinol. Metab. 81:669-676, Robertson et al., 1997, J. Clin. Endocrinol. Metab. 82:889-896).

Figure 11:
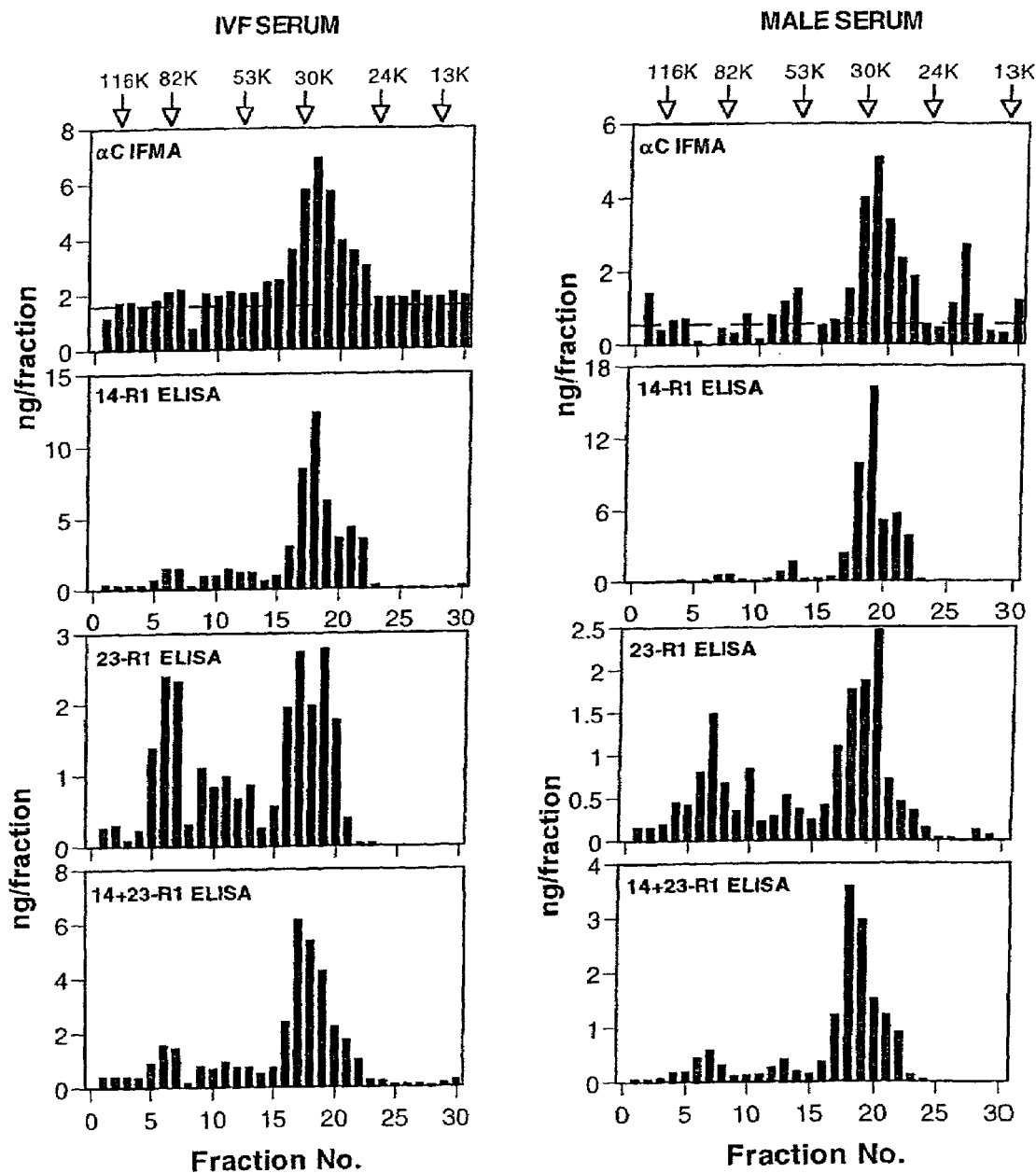
FIG. 11 illustrates molecular weight patterns of inhibin in serum from women stimulated with gonadotropins as part of an in vitro fertilization procedure (IVF serum) and male serum. The serum was fractionated using an immunoaffinity, preparative-PAGE and electroelution procedure (Robertson et al 1996, 1997, supra). Horizontal dashed line refers to detection limit.

Inhibin forms were separated into their various molecular weight forms by this procedure and thus available for assessment by the various inhibin assays. As seen in FIG. 11, a comparison of the molecular weight profiles obtained with the 14-R1 and 23-R1 ELISAs for IVF serum and male serum showed that the 14-R1 ELISA gave a molecular weight pattern similar to that seen with the Pro-(alpha)C ELISA with 25-40 k inhibin forms primarily detected. In contrast, 23-R1 ELISA detected high molecular weight forms in the 50-100 k range in greater abundance, similar to that seen with inhibin A and B ELISAs. These data suggest that 14-R1 ELISA is directed more to the alpha subunit monomer while the 23-R1 ELISA is directed more to the inhibin dimer.

Since the purpose of the proposed inhibin alpha ELISA was to detect all alpha subunit containing forms, i.e., both free alpha subunits and inhibin dimer, a further ELISA was devised consisting of both PO#14 and PO#23 as coating antibodies with AP-R1 as label, the aim of which was to combine the specificities of the 14-R1 and 23-R1 ELISAs. The characteristics of this ELISA are included in the various Tables and Figures considered for the individual ELISAs. The 14+23-R1 ELISA was more sensitive than the other inhibin alpha ELISAs with good reproducibility (Table 11). The molecular weight patterns of inhibins in IVF and male serum determined by the 14+23-R1 ELISA is a mixture of patterns of both 14-R1 and 23-R1 assays (FIG. 11).

Example 8

Application to Serum from Women with Ovarian Cancers

The application of the various ELISAs to fractionated serum from women with ovarian cancer showed a similar molecular weight pattern for all three ELISAs (FIG. 12) as different from that seen in IVF and male serum, perhaps reflecting the high levels of monomeric alpha subunit forms compared to the dimeric forms present in these cancer samples.

Figure 13:
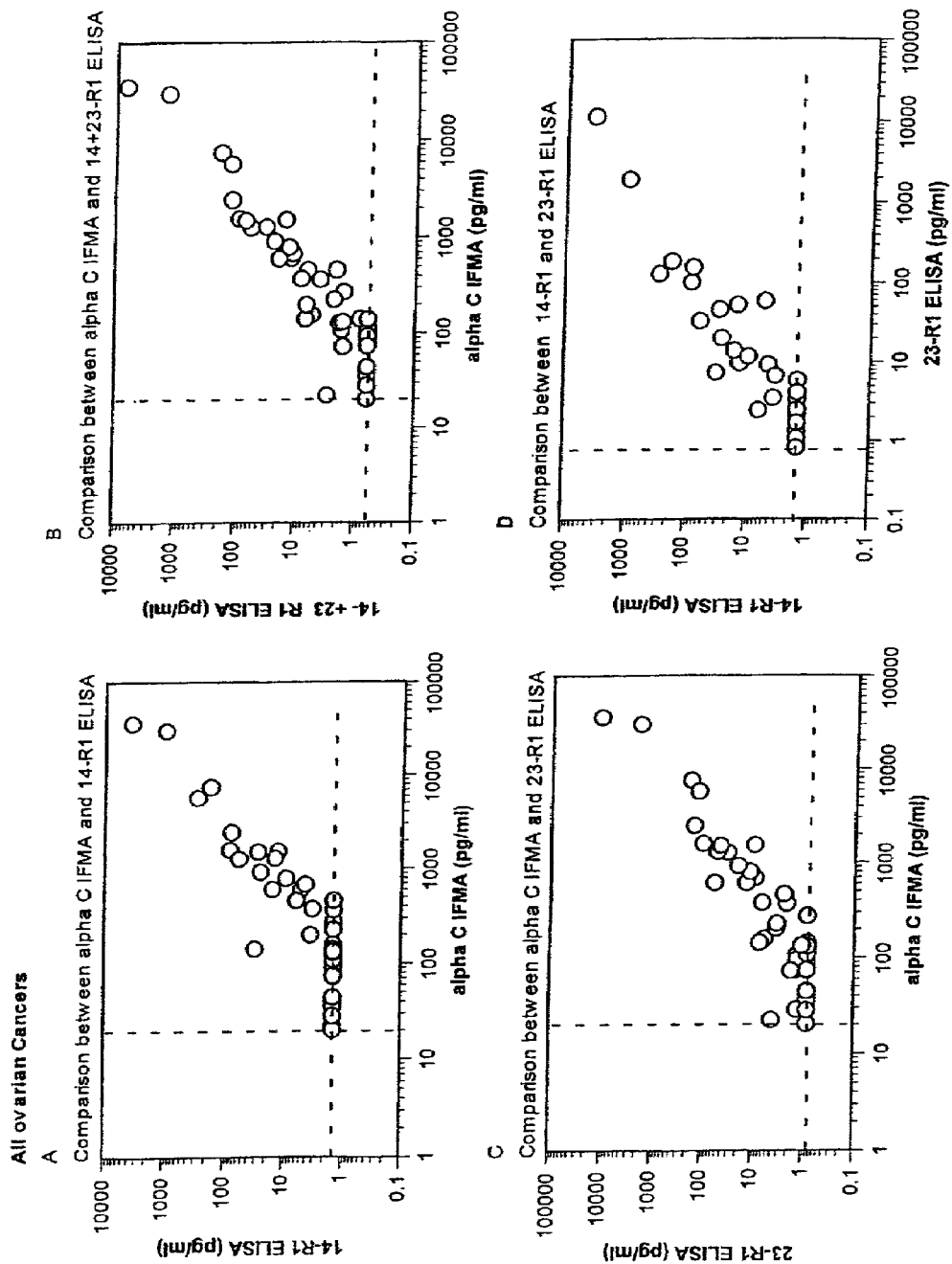
FIG. 13 shows regression analyses of serum inhibin values from women with all ovarian cancers as determined by a) IFMA and 14-R1 ELISA, b) IFMA and 23-R1 ELISA, c) IFMA and 14+23-R1 ELISA, and d) 23-R1 ELISA and 14-R1 ELISA. Dashed lines refer to the detection limits of the various assays.

The three ELISAs (14-R1, 23-R1, 14+23-R1) were then applied to serum from normal postmenopausal women (>55 years) and postmenopausal women with a range of ovarian cancers. As seen in Tables 14 and 15, in comparison with the IFMA, the three ELISAs readily detected inhibin levels in granulosa and mucinous tumours compared to normal controls with largely similar degrees of discrimination (Table 15). The 14+23-R1 ELISA showed the largest difference between cancer and control groups. Regression analysis between serum inhibin levels determined by the IFMA and each of the inhibin alpha ELISAs showed good correlations (Table 16, FIG. 13). These data suggest that 14+23-R1 is marginally better than the 14-R1 but based on the higher specificity of the 14+23-R1 ELISA for all inhibin forms, it is probably the better ovarian cancer assay.

Example 9

Other Applications of PO#14 and PO#23 Antisera
Other ELISAs

Figure 12:
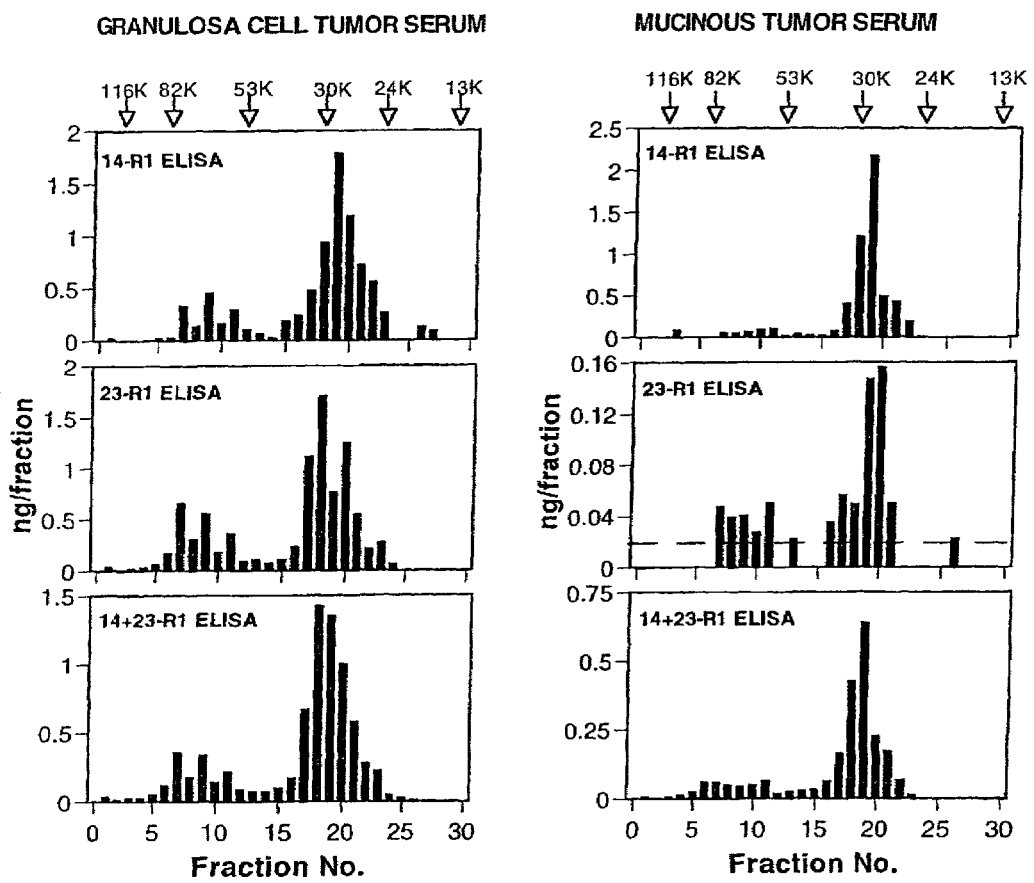
FIG. 12 shows molecular weight patterns of inhibin in serum from postmenopausal women with granulosa cell tumours and mucinous cancer. The serum was fractionated using an immunoaffinity, preparative-PAGE and electroelution procedure (Robertson et al. 1996, 1997, supra). Horizontal dashed line refers to detection limits of the various assays.

Current inhibin A and B and Pro-(alpha)C ELISAs use the R1 MAb as alpha subunit label (hereinafter referred to as the "Groome" assays and the like). Studies were undertaken to replace the R1 MAb with either the PO#14 or PO#23 monoclonal antibody. Neither MAb in combination with the (beta)B subunit MAb (C5) gave a response in the ELISA. A comparison of ELISA assays in the fractionation of IVF and male serum showed that the current Groome inhibin A ELISA (consisting of the (beta)A subunit MAb (E4) and R1) showed little differences with the other inhibin alpha ELISAs, except that higher molecular weight forms (>80 k) were detected with the Groome inhibin A ELISA (FIG. 12). However, the combination of INPRO MAb which detects the Pro-region of the alpha subunit with PO#14 (INPRO-Ap-14) detected the presence of high molecular weight forms of Pro-(alpha)C not detected with the traditional Pro-R1 MAb combination. These findings suggest that the PO#14 MAb is a better MAb than R1 in conjunction with INPRO MAb in detecting Pro-(alpha)C forms. A combination of PO#23 and INPRO resulted in an insensitive assay.

Immunocytochemistry

Previous studies by many groups have shown that the alpha subunit R1 antibody used as an immunocytochemical reagent readily detects granulosa cell tumours but not mucinous or other epithelial cell cancers. Studies using PO#14 and PO#23 as immunocytochemical reagents showed that these Mabs also detected granulosa cell tumours, but in addition PO#14 readily detected a range of tumours including ovarian mucinous epithelial cancers. These studies suggest the PO#14 may be useful in the immunocytochemical identification of mucinous tumours as well as other ovarian cancers not currently possible with R1.

GENERAL CONCLUSIONS

Five (possibly 6) epitopes on the inhibin (alpha)C subunit have been identified (see Table 5) with epitopes #5a+5b representing 65-73% of the 30 kDa inhibin binding, epitope #20a and #20b, 13%, and epitope #30, 28%, of the mixture, although following the pre-absorption of the #5 epitopes, the others take on a larger role. There is an additional epitope recognized by As #128 which has not been identified. It is unclear to what extent these various epitopes are important in the specificity of the overall assay as it is likely that they may contribute differently according to the type and form of inhibin being detected.

It would appear that an antibody to epitope 5a, which is recognized by As #128, is sufficient to act as a capture antibody, while epitopes #5b and #30 appear to be the key epitopes recognized by As #41. However it should be noted that there is a third epitope recognized by As# 128 representing 45% of the total binding which has not as yet been identified.

Epitopes in the peptide #5 sequence are located near the amino terminal of the (alpha)C subunit. Based on preliminary analysis using the peptides and the solid assay procedure presented in Assay 1, these epitopes are probably different to that detected by the inhibin (alpha)C subunit monoclonal antibody of Groome et al. (11994, Clin. Endocrinol. 40:717-723) and used in the SEROTEC™ (alpha)(beta) dimer ELISA which primarily detects peptide 3 as listed in Table 1. However, these epitopes in the peptide #5 sequence may be similar although not necessarily identical to the sequences used in the alpha-alpha inhibin assay provided commercially by the company Medgenix. (See Table 5 and FIG. 7, see Robertson et al., 1996, J. Cell. Endocrinol. Metabol. 81:669-676 for further details).

Peptides #20a, #20b and #30 as epitopes are unique. Peptide #30 also shows a high affinity to rabbit antiserum #1989, which was employed in the earlier discussed inhibin RIA. Previous studies by other workers (Lambert-Messerlian et al., 1995, J. Cell. Endocrinol. Metabol. 80:3043) had localized the As #1989 epitope on the alpha-subunit to a different region (amino acid sequences 326-341 of the full alpha subunit or amino acids 94-109 of the (alpha)C subunit region, See FIG. 9). However in the present study peptide #30 (from both the first and second series of peptides) was the only peptide to compete with inhibin for this antiserum. We thus presume that the observations by Lambert-Messerlian and colleagues are incorrect.

An interesting observation from this study is that both peptide #5 and #30 show high sequence homology across a range of species (rat, bovine, ovine, human) with 13 of 14 amino acids of both peptides common between the human and the other species. Thus an assay based on these (alpha)C subunit sequences would be appropriate in detecting inhibin alpha subunit in a range of species. Since the sequences of the (beta)A and (beta)B subunits show little or no differences over a range of species, combination of an antibody to the (beta)A/(beta)B subunit sequences and to one of these alpha-subunit peptide sequences would provide a basis for an "all species" assays of inhibin A and B. At the moment the R1 alpha-subunit antibody used in the human inhibin A and B ELISAs made by Groome show variable cross-reaction with inhibin from other species. In fact Groome has produced specific antibodies to the alpha-subunit of bovine and ovine inhibin in order to detect inhibin A and B in these species.

Three inhibin alpha ELISAs were developed to replace the IFMA as an ovarian cancer diagnostic. These assays exhibit different specificities for the various inhibin forms, however the ability of these assays to discriminate between controls and ovarian cancer was similar to that observed with the IFMA.

While the three inhibin alpha ELISAs are more sensitive than the IFMA it is unclear which assay is preferred as an ovarian cancer marker at this point. Further studies with a larger number of samples may resolve this issue. Because of the differing sensitivities between the 14-R1 and 23-R1 ELISAs, the combination assay 14+23-R1 ELISA would appear to be the most appropriate. It is worth noting that the 14+23-R1 ELISA is more sensitive than the others as well as giving the largest discrimination (difference between control values and cancer values) relative to the other ELISAs.

PO#14 and PO#23 Mabs appear to be of value in detecting particular forms of inhibin not detected by the present inhibin/Pro-(alpha)C ELISAs and are likely to be useful in developing new assays for these proteins.

PO#14 and PO#23 Mabs, and particularly PO#14 are considerably better than R1 in detecting various types of ovarian cancers by immunocytochemistry. Thus PO#14 and PO#23 Mabs appear to be useful reagents in detecting ovarian cancers by this technique.

All references, patents and patent applications referred to herein are incorporated herein by reference.

Throughout the specification, the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

TABLE 1

Initial set of peptides derived from the human (alpha)C subunit examined in this study
Peptides 1 and 2 were Chiron quality control samples and not included in this study. Single letter code for the amino acids is used. A biotinylated 4 amino acid spacer (SGSG) with an N-terminal biotin is attached to the N-terminus of each peptide. Hydro = hydrophobicity index. Linker sequence is SEQ ID NO: 77.

| # | Linker + Peptide | Hydro | Mol Wt | Peptide SEQ ID NO | Position relative to SEQ ID NO: 2 |
|---|---|---|---|---|---|
| 1,2 | quality control peptides | | | | |
| 3 | SGSG STPLMSWPWSPSAL | 0.65 | 1830.07 | 3 | 1-14 |

TABLE 1-continued

Initial set of peptides derived from the human (alpha)C subunit examined in this study
Peptides 1 and 2 were Chiron quality control samples and not included in this study. Single letter code for the amino acids is used. A biotinylated 4 amino acid spacer (SGSG) with an N-terminal biotin is attached to the N-terminus of each peptide. Hydro = hydrophobicity index. Linker sequence is SEQ ID NO: 77.

| # | Linker + Peptide | Hydro | Mol Wt | Peptide SEQ ID NO | Position relative to SEQ ID NO: 2 |
|---|---|---|---|---|---|
| 4 | SGSG MSWPWSPSALRLLQ | 0.62 | 1942.24 | 4 | 5-18 |
| 5 | SGSG WSPSALRLLQRPPE | 0.38 | 1920.18 | 5 | 9-22 |
| 6 | SGSG ALRLLQRPPEEPAA | 0.26 | 1831.09 | 6 | 13-26 |
| 7 | SGSG LQRPPEEPAAHANC | 0.18 | 1802.96 | 7 | 17-30 |
| 8 | SGSG PEEPAAHANCHRVA | 0.15 | 1771.90 | 8 | 21-34 |
| 9 | SGSG AAHANCHRVALNIS | 0.30 | 1746.92 | 9 | 25-38 |
| 10 | SGSG NCHRVALNISFQEL | 0.39 | 1914.13 | 10 | 29-42 |
| 11 | SGSG VALNISFQELGWER | 0.42 | 1932.13 | 11 | 33-46 |
| 12 | SGSG ISFQELGWERWIVY | 0.62 | 2096.34 | 12 | 37-50 |
| 13 | SGSG ELGWERWIVYPPSF | 0.61 | 2049.29 | 13 | 41-54 |
| 14 | SGSG ERWIVYPPSFIFHY | 0.69 | 2124.41 | 14 | 45-58 |
| 15 | SGSG VYPPSFIFHYCHGG | 0.65 | 1894.11 | 15 | 49-62 |
| 16 | SGSG SFIFHYCHGGCGLH | 0.63 | 1848.05 | 16 | 53-66 |
| 17 | SGSG HYCHGGCGLHIPPN | 0.48 | 1774.95 | 17 | 57-70 |
| 18 | SGSG GGCGLHIPPNLSLP | 0.56 | 1644.87 | 18 | 61-74 |
| 19 | SGSG LHIPPNLSLPVPGA | 0.60 | 1694.96 | 19 | 65-78 |
| 20 | SGSG PNLSLPVPGAPPTP | 0.49 | 1626.85 | 20 | 69-82 |
| 21 | SGSG LPVPGAPPTPAQPY | 0.49 | 1674.90 | 21 | 73-86 |
| 22 | SGSG GAPPTPAQPYSLLP | 0.47 | 1678.89 | 22 | 77-90 |
| 23 | SGSG TPAQPYSLLPGAQP | 0.42 | 1709.90 | 23 | 81-94 |
| 24 | SGSG PYSLLPGAQPCCAA | 0.57 | 1660.90 | 24 | 85-98 |
| 25 | SGSG LPGAQPCCAALPGT | 0.53 | 1568.80 | 25 | 89-102 |
| 26 | SGSG QPCCAALPGTMRPL | 0.52 | 1728.06 | 26 | 93-106 |
| 27 | SGSG AALPGTMRPLHVRT | 0.36 | 1790.10 | 27 | 97-110 |
| 28 | SGSG GTMRPLHVRTTSDG | 0.16 | 1797.99 | 28 | 101-114 |
| 29 | SGSG PLHVRTTSDGGYSF | 0.28 | 1806.93 | 29 | 105-118 |
| 30 | SGSG RTTSDGGYSFKYET | 0.05 | 1881.96 | 30 | 109-122 |
| 31 | SGSG DGGYSFKYETVPNL | 0.25 | 1859.98 | 31 | 113-126 |
| 32 | SGSG SFKYETVPNLLTQH | 0.34 | 1947.15 | 32 | 117-130 |
| 33 | SGSG ETVPNLLTQHCACI | 0.54 | 1812.06 | 33 | 121-134 |

TABLE 2

ED$_{50}$ values for the 31 peptides obtained in the RIA with the various antisera.

| Peptide No. | As#41 ED$_{50}$ nmoles/mL | As#128 ED$_{50}$ nmoles/mL | As#1989 ED$_{50}$ nmoles/mL |
|---|---|---|---|
| 3 |  | 38 | >2.5 |
| 4 | 1.3 | 3.8 | >2.5 |
| 5 | 0.000015 | 3.8 | >2.5 |
| 6 | 0.026 | 1.8 | >2.5 |
| 7 | 1.25 | 1.6 | >2.5 |
| 8 | >10 | 4.8 | >2.5 |
| 9 | >10 | >10 | >2.5 |
| 10 | >10 | >10 | >2.5 |
| 11 | >10 | >10 | >2.5 |
| 12 | >10 | >10 | >2.5 |
| 13 | >10 | >10 | >2.5 |
| 14 | >10 | >10 | >2.5 |
| 15 | >10 | >10 | >2.5 |
| 16 | >10 | >10 | >2.5 |
| 17 | 1.05 | 10 | >2.5 |
| 18 | 1.05 | 0.06 | >2.5 |
| 19 | 2.1 | <0.01 | >2.5 |
| 20 | 3.6 | 0.02 | >2.5 |
| 21 | 1 | 0.156 | >2.5 |
| 22 | 5 | 0.156 | >2.5 |
| 23 | 6.2 | 0.5 | >2.5 |
| 24 | 6.2 | 0.9 | >2.5 |
| 25 | 5 | 2 | >2.5 |
| 26 | 1 | 0.625 | >2.5 |
| 27 | 5 | 2 | >2.5 |
| 28 | 4 | 0.625 | >2.5 |
| 29 | 5 | 0.156 | >2.5 |
| 30 | 2.5 | 0.6 | <0.01 |
| 31 | 2.4 | 1.4 | >2.5 |
| 32 | 0.29 | 2.5 | >2.5 |
| 33 | 4 | 2.5 | >2.5 |

TABLE 3

ED$_{50}$ values for hr-inhibin A as standard and peptides #5, #20 and #30 obtained in the RIA with the various antisera.

| | ED$_{50}$ values (nmole/ml) | | |
|---|---|---|---|
| | As#41 | As#128 | As#1989 |
| Hr-inhibin* | 0.002-8 | 0.002 | 0.0001 |
| Peptide #5 | 0.0004 | >10 | >10 |
| Peptide #20 | >5 | 0.15 | >5 |
| Peptide #30 | >5 | >5 | 2.5 |

*human recombinant 30 kDa inhibin A

TABLE 4

The effect of pre-immunoabsorption of As#128 and/or As#41 with peptides #5, #20 and #30 in the inhibin IFMA. This data is derived from FIG. 5 and is presented as the percentage inhibition of binding of the 2ng-inhibin dose by the 3 peptides, individually or combined.

| As#128 as Coating Antibody | As#41 as Label | % suppression at 2ng inhibin |
|---|---|---|
| Buffer | buffer | 0 |
| #5, #20, #30 | #5, #20, #30 | 95 |
| Buffer | #5 | 67 |
| #5 | buffer | 55 |
| #5 | #5 | 73 |
| #5 | #30 | 80 |
| #5, #20 | buffer | 55 |
| #20 | buffer | 13 |
| #20 | #30 | 34 |
| #20 | #5 | 70 |
| Buffer | #30 | 28 |

TABLE 5

Summary of data for the 31 peptides in terms of their relative contributions in the various assays. +++++ major contribution, + minor contribution. Based on these data peptides #5, #20 and #30 were chosen. Peptide #19 may be preferred in comparison with peptide #20, however its solubility is limited based on its hydrophobicity index (see Table 1).

| Tube | #41 Antibody screen Assay 1 | #41 RIA Assay 2 | #41 2-site competitive assay Assay 3 | combination epitopes Assay 3 | Peptide No. | #128 Antibody screen Assay 1 | #128 RIA ED$_{50}$ Assay 2 | #128 2-site competitive assay Assay 3 | #1989 RIA |
|---|---|---|---|---|---|---|---|---|---|
| 3 |  |  |  |  | 3 | +++ | + | ++ |  |
| 4 | +++ | ++ |  |  | 4 | + | + | + |  |
| 5 | +++ | ++++++ | ++++ |  | 5 | + | + | ++ |  |
| 6 | +++ | +++ |  |  | 6 | + | ++ | + |  |
| 7 | +++ |  |  |  | 7 | + | ++ | + |  |

TABLE 5-continued

Summary of data for the 31 peptides in terms of their relative contributions in the various assays. +++++ major contribution, + minor contribution. Based on these data peptides #5, #20 and #30 were chosen. Peptide #19 may be preferred in comparison with peptide #20, however its solubility is limited based on its hydrophobicity index (see Table 1).

| Tube | #41 Antibody screen Assay 1 | #41 RIA Assay 2 | #41 2-site competitive assay Assay 3 | combination epitopes Assay 3 | Peptide No. | #128 Antibody screen Assay 1 | #128 RIA ED$_{50}$ Assay 2 | #128 2-site competitive assay Assay 3 | #1989 RIA |
|---|---|---|---|---|---|---|---|---|---|
| 28 | + |   | ++ |   | 18 | + | +++ | + |   |
| 29 | +++ | + | +++ | 100% 5 + 29 | 19 | + | +++ | + |   |
| 30 | +++ | ++ | +++ | 100% 5 + 30 | 20 | + | +++ | + | +++++ |
| 31 | + | ++ | ++ |   | 28 | ++ | ++ | ++ |   |
| 32 |   | +++ | ++ |   | 29 | ++ | +++ | ++ |   |
| 33 |   | ++ | + |   | 30 | ++ | ++ | ++ |   |
|   |   |   |   |   | 31 | ++ |   |   |   |
|   |   |   |   |   | 32 | ++ |   |   |   |
|   |   |   |   |   | 33 | ++ |   |   |   |

TABLE 6

Available inhibin alpha subunit antisera used in immunoassays

| Title | Ref | Assay | Specificity | (alpha)C subunit Antiserum | (alpha)C subunit sequence as antigen | epitope region (alpha)C subunit |
|---|---|---|---|---|---|---|
| Groome (R1) | 1, 2 | ELISAs | Inhibin A, B, Pro-(alpha)C | mouse monoclonal (R1) | 1-32 aa | 1-32 aa |
| Medgenix | 3 |   | inhibin, inhibin alpha subunit | polyclonal, | 1-17 aa | 1-17 aa |
|   |   |   |   | mouse monoclonal | 15-32 aa | 15-32 aa |
| Monash (#1989) This study | 4 | RIA | inhibin, inhibin alpha subunit | rabbit polyclonal (#1989) | bovine 31k inhibin | 109-122 aa |
| Monash This study | 5 | IFMA | inhibin, inhibin alpha subunit | sheep polyclonal (#128, #41) | (alpha)C subunit fusion protein | 9-22 aa |
|   |   |   |   |   | (alpha)C subunit fusion protein | 69-82 aa |
|   |   |   |   |   | (alpha)C subunit fusion protein | 109-122 aa |

1 Groome et al., 1993, Immunol. Meth. 165: 167-176.
2 Groome et al., 1994, Clin. Endocrinol. 40: 717-723.
3 Poncelet et al., 1994, Ares-Serono Symposia Series-Frontiers in Endocrinology 3: 45-54.
4 Robertson et al., 1988, J. Clin. Endocrinol. Metab. 67: 438-448.
5 Robertson et al., 1999, Clin. Chem. 45: 651-658.

TABLE 7

Second set of peptides derived from the human (alpha)C subunit examined in this study
Set 1 peptides correspond to 30 biotinylated peptides with 4 amino acid offset sequences of human (alpha)C subunit presented in Table 1. Set 2 peptides correspond to 41 biotinylated peptides with 2-4 amino acid offset sequences. The common sequence SGKG is a linker sequence. The presented Set 1 sequences are either a combination of two Set 2 sequences (for example see peptide 3 in Set 1 which is a combination of peptide 1 and 2 of Set 2) or a matching sequence with Set 1.

| Set 1 | Set 1 Offset | Set 2 | Set 2 Offset | linker SEQ ID NO: 77 | Peptide Sequence | Peptide SEQ ID NO | Position relative to SEQ ID NO: 2 |
|---|---|---|---|---|---|---|---|
| 3 | 4 | 1 | 2 | SGKG | STPLMSWPWSPSAL | 34 | 1-14 |
|   |   | 2 | 2 | SGKG | PLMSWPWSPSALRL | 35 | 3-16 |
| 4 | 4 | 3 | 2 | SGKG | MSWPWSPSALRLLQ | 36 | 5-18 |
| 4 |   | 4 | 2 | SGKG | WPWSPSALRLLQRP | 37 | 7-20 |

TABLE 7-continued

Second set of peptides derived from the human (alpha)C subunit examined in this study
Set 1 peptides correspond to 30 biotinylated peptides with 4 amino acid offset sequences of human (alpha)C subunit presented in Table 1. Set 2 peptides correspond to 41 biotinylated peptides with 2-4 amino acid offset sequences. The common sequence SGKG is a linker sequence. The presented Set 1 sequences are either a combination of two Set 2 sequences (for example see peptide 3 in Set 1 which is a combination of peptide 1 and 2 of Set 2) or a matching sequence with Set 1.

| Set 1 | Offset | Set 2 | Offset | linker SEQ ID NO: 77 | Peptide Sequence | Peptide SEQ ID NO | Position relative to SEQ ID NO: 2 |
|---|---|---|---|---|---|---|---|
| 5 | 4 | 5 | 2 | SGKG | WSPSALRLLQRPPE | 38 | 9-22 |
| 5 |   | 6 | 2 | SGKG | PSALRLLQRPPEEP | 39 | 11-24 |
| 6 | 4 | 7 | 4 | SGKG | ALRLLQRPPEEPAA | 40 | 13-26 |
| 7 | 4 | 8 | 4 | SGKG | LQRPPEEPAAHANC | 41 | 17-30 |
| 8 | 4 | 9 | 4 | SGKG | PEEPAAHANCHRVA | 42 | 21-34 |
| 9 | 4 | 10 | 4 | SGKG | AAHANCHRVALNIS | 43 | 25-38 |
| 10 | 4 | 11 | 4 | SGKG | NCHRVALNISFQEL | 44 | 29-42 |
| 11 | 4 | 12 | 4 | SGKG | VALNISFQELGWER | 45 | 33-46 |
| 12 | 4 | 13 | 4 | SGKG | ISFQELGWERWIVY | 46 | 37-50 |
| 13 | 4 | 14 | 4 | SGKG | ELGWERWIVYPPSF | 47 | 41-54 |
| 14 | 4 | 15 | 4 | SGKG | ERWIVYPPSFIFHY | 48 | 45-58 |
| 15 | 4 | 16 | 4 | SGKG | VYPPSFIFHYCHGG | 49 | 49-62 |
| 16 | 4 | 17 | 4 | SGKG | SFIFHYCHGGCGLH | 50 | 53-66 |
| 17 | 4 | 18 | 4 | SGKG | HYCHGGCGLHIPPN | 51 | 57-70 |
| 18 | 4 | 19 | 4 | SGKG | GGCGLHIPPNLSLP | 52 | 61-74 |
| 19 | 4 | 20 | 4 | SGKG | LHIPPNLSLPVPGA | 53 | 65-78 |
| 20 | 4 | 21 | 4 | SGKG | PNLSLPVPGAPPTP | 54 | 69-82 |
| 21 | 4 | 22 | 2 | SGKG | LPVPGAPPTPAQPY | 55 | 73-86 |
| 21 |   | 23 | 2 | SGKG | VPGAPPTPAQPYSL | 56 | 75-88 |
| 22 | 4 | 24 | 2 | SGKG | GAPPTPAQPYSLLP | 57 | 77-90 |
| 22 |   | 25 | 2 | SGKG | PPTPAQPYSLLPGA | 58 | 79-92 |
| 23 | 4 | 26 | 2 | SGKG | TPAQPYSLLPGAQP | 59 | 81-94 |
| 23 |   | 27 | 2 | SGKG | AQPYSLLPGAQPCC | 60 | 83-96 |
| 24 | 4 | 28 | 2 | SGKG | PYSLLPGAQPCCAA | 61 | 85-98 |
| 24 |   | 29 | 4 | SGKG | SLLPGAQPCCAALP | 62 | 87-100 |
| 25 | 4 | 30 | 4 | SGKG | LPGAQPCCAALPGT | 63 | 89-102 |
| 26 | 4 | 31 | 4 | SGKG | QPCCAALPGTMRPL | 64 | 93-106 |
| 27 | 4 | 32 | 4 | SGKG | AALPGTMRPLHVRT | 65 | 97-110 |
| 28 | 4 | 33 | 4 | SGKG | GTMRPLHVRTTSDG | 66 | 101-114 |
| 29 | 4 | 34 | 4 | SGKG | PLHVRTTSDGGYSF | 67 | 105-118 |
| 30 | 4 | 35 | 2 | SGKG | RTTSDGGYSFKYET | 68 | 109-122 |
| 30 |   | 36 | 2 | SGKG | TSDGGYSFKYETVP | 69 | 111-124 |
| 31 | 4 | 37 | 2 | SGKG | DGGYSFKYETVPNL | 70 | 113-126 |

TABLE 7-continued

Second set of peptides derived from the human (alpha)C subunit examined in this study
Set 1 peptides correspond to 30 biotinylated peptides with 4 amino acid offset sequences of human (alpha)C subunit presented in Table 1. Set 2 peptides correspond to 41 biotinylated peptides with 2-4 amino acid offset sequences. The common sequence SGKG is a linker sequence. The presented Set 1 sequences are either a combination of two Set 2 sequences (for example see peptide 3 in Set 1 which is a combination of peptide 1 and 2 of Set 2) or a matching sequence with Set 1.

| Set 1 | Set 1 Offset | Set 2 | Set 2 Offset | linker SEQ ID NO: 77 | Peptide Sequence | Peptide SEQ ID NO | Position relative to SEQ ID NO: 2 |
|---|---|---|---|---|---|---|---|
| 31 |  | 38 | 2 | SGKG | GYSFKYETVPNLLT | 71 | 115-128 |
| 32 | 4 | 39 | 2 | SGKG | SFKYETVPNLLTQH | 72 | 117-130 |
| 32 |  | 40 | 2 | SGKG | KYETVPNLLTQHCA | 73 | 119-132 |
| 33 | 4 | 41 | 4 | SGKG | ETVPNLLTQHCACI | 74 | 121-134 |

TABLE 8

Assessment of binding by solid phase binding and radioimmunoassay of the 41 biotinylated peptides to the various PO# monoclonal antibodies

| Set 2 | Offset | R1 SPB | R1 RIA | PO-6 SPB | PO-6 RIA | PO-9 SPB | PO-9 RIA | PO-12 SPB | PO-12 RIA | PO-14 SPB | PO-14 RIA |
|---|---|---|---|---|---|---|---|---|---|---|---|
| 1 | 2 |  |  |  |  |  |  |  |  |  |  |
| 2 | 2 | +++ | ΦΦΦ | +++ | a) |  |  |  |  |  |  |
| 3 | 2 | +++ | ΦΦΦ | +++ |  |  |  |  |  |  |  |
| 4 | 2 | + | ΦΦΦ | +++ |  |  |  |  |  |  |  |
| 5 | 2 | + | ΦΦΦ | +++ |  |  |  |  |  |  |  |
| 6 | 2 |  | Φ |  |  |  |  |  |  |  |  |
| 7 | 4 |  |  |  |  |  |  |  |  |  |  |
| 8 | 4 |  |  |  |  |  |  |  |  |  |  |
| 9 | 4 |  |  |  |  |  |  |  |  |  |  |
| 10 | 4 |  |  |  |  |  |  |  |  |  |  |
| 11 | 4 |  |  |  |  |  |  |  |  |  |  |
| 12 | 4 |  |  |  |  |  |  |  |  |  |  |
| 13 | 4 |  |  |  |  |  |  |  |  |  |  |
| 14 | 4 |  |  |  |  |  |  |  |  |  |  |
| 15 | 4 |  |  |  |  |  |  |  |  |  |  |
| 16 | 4 |  |  |  |  |  |  |  |  |  |  |
| 17 | 4 |  |  |  |  |  |  |  |  |  |  |
| 18 | 4 |  |  |  |  |  |  |  |  |  |  |
| 19 | 4 |  |  |  |  |  |  |  |  |  |  |
| 20 | 4 |  |  |  |  |  |  |  |  |  |  |
| 21 | 4 |  |  |  |  |  |  |  |  |  |  |
| 22 | 2 |  |  |  |  |  |  | +++ | Φ | +++ | Φ |
| 23 | 2 |  |  |  |  |  |  | +++ | ΦΦΦ | +++ | ΦΦ |
| 24 | 2 |  |  |  |  |  |  | +++ | ΦΦΦ | +++ | ΦΦΦ |
| 25 | 2 |  |  |  |  |  |  | +++ | ΦΦΦ | +++ | ΦΦΦ |
| 26 | 2 |  |  |  |  |  |  | +++ | ΦΦΦ | +++ | ΦΦΦ |
| 27 | 2 |  |  |  |  |  |  | ++ | Φ | +++ | ΦΦ |
| 28 | 2 |  |  |  |  |  |  |  |  |  |  |
| 29 | 4 |  |  |  |  |  |  |  |  |  |  |
| 30 | 4 |  |  |  |  |  |  |  |  |  |  |
| 31 | 4 |  |  |  |  |  |  |  |  |  |  |
| 32 | 4 |  |  |  |  |  |  |  |  |  |  |
| 33 | 4 |  |  |  |  |  |  |  |  |  |  |
| 34 | 4 |  |  |  |  |  |  |  |  |  |  |
| 35 | 2 |  |  |  |  | +++ | Φ |  |  |  |  |
| 36 | 2 |  |  |  |  | +++ | ΦΦΦ |  |  |  |  |
| 37 | 2 |  |  |  |  | ++ | ΦΦΦ |  |  |  |  |

TABLE 8-continued

Assessment of binding by solid phase binding and radioimmunoassay of the 41 biotinylated peptides to the various PO# monoclonal antibodies

| Set 2 | Offset | R1 SPB | R1 RIA | PO-6 SPB | PO-6 RIA | PO-9 SPB | PO-9 RIA | PO-12 SPB | PO-12 RIA | PO-14 SPB | PO-14 RIA |
|---|---|---|---|---|---|---|---|---|---|---|---|
| 38 | 2 |  |  |  |  | + | ΦΦΦ |  |  |  |  |
| 39 | 2 |  |  |  |  | (+) | Φ |  |  |  |  |
| 40 | 2 |  |  |  |  |  |  |  |  |  |  |
| 41 | 4 |  |  |  |  |  |  |  |  |  |  |

Solid phase binding = SPB;
RIA = radioimmunoassay +++;
ΦΦΦ strong effect,
+, Φ weak effect;
a) limited binding

TABLE 9

Assessment of binding by solid phase binding and radioimmunoassay of the 41 biotinylated peptides to the various PO# monoclonal antibodies

| Set 2 | Offset | PO-19 SPB | PO-19 RIA | PO-22 SPB | PO-22 RIA | PO-23 SPB | PO-23 RIA | PO-25 SPB | PO-25 RIA | PO-26 SPB | PO-26 RIA |
|---|---|---|---|---|---|---|---|---|---|---|---|
| 1 | 2 |  |  |  | ΦΦ |  |  |  |  |  |  |
| 2 | 2 |  |  | +++ | ΦΦ |  |  |  |  |  |  |
| 3 | 2 |  |  | +++ | ΦΦΦ |  |  |  |  |  |  |
| 4 | 2 |  |  | +++ | ΦΦΦ |  |  |  |  |  |  |
| 5 | 2 |  |  | +++ | ΦΦ |  |  |  |  |  |  |
| 6 | 2 |  |  |  |  |  |  |  |  |  |  |
| 7 | 4 |  |  |  |  |  |  |  |  |  |  |
| 8 | 4 |  |  |  |  |  |  |  |  |  |  |
| 9 | 4 |  |  |  |  |  |  |  |  |  |  |
| 10 | 4 |  |  |  |  |  |  |  |  |  |  |
| 11 | 4 |  |  |  |  |  |  |  |  |  |  |
| 12 | 4 |  |  |  |  |  |  |  |  |  |  |
| 13 | 4 |  |  |  |  |  |  |  |  |  |  |
| 14 | 4 |  |  |  |  |  |  |  |  |  |  |
| 15 | 4 |  |  |  |  |  |  |  |  |  |  |
| 16 | 4 |  |  |  |  |  |  |  |  |  |  |
| 17 | 4 |  |  |  |  |  |  |  |  |  |  |
| 18 | 4 |  |  |  |  |  |  |  |  |  |  |
| 19 | 4 |  |  |  |  |  |  |  |  |  |  |
| 20 | 4 |  |  |  |  |  |  |  |  |  |  |
| 21 | 4 |  |  |  |  |  |  |  |  |  |  |
| 22 | 2 |  |  |  |  |  |  |  |  |  |  |
| 23 | 2 |  |  |  |  |  |  |  |  |  |  |
| 24 | 2 |  |  |  |  |  |  |  |  |  |  |
| 25 | 2 |  |  |  |  |  |  |  |  |  |  |
| 26 | 2 |  |  |  |  |  |  |  |  |  |  |
| 27 | 2 |  |  |  |  |  |  |  |  |  |  |
| 28 | 2 |  |  |  |  |  |  |  |  |  |  |
| 29 | 4 |  |  |  |  |  |  |  |  |  |  |
| 30 | 4 |  |  |  |  |  |  |  |  |  |  |
| 31 | 4 |  |  |  |  |  |  |  |  |  |  |
| 32 | 4 |  |  |  |  |  |  |  |  |  |  |
| 33 | 4 |  |  |  |  |  |  |  |  |  |  |
| 34 | 4 |  |  |  |  |  | ΦΦ |  |  |  |  |
| 35 | 2 | +++ | ΦΦΦ |  |  | +++ | ΦΦ | +++ | ΦΦΦ | +++ | ΦΦΦ |
| 36 | 2 | +++ | ΦΦΦ |  |  | +++ | ΦΦΦ | +++ | ΦΦΦ | +++ | ΦΦΦ |
| 37 | 2 | +++ | ΦΦΦ |  |  | ++ | ΦΦΦ | ++ | ΦΦΦ | ++ | ΦΦΦ |
| 38 | 2 | ++ | ΦΦΦ |  |  | ++ | ΦΦΦ | + | ΦΦΦ | + | ΦΦΦ |
| 39 | 2 | + | ΦΦ |  |  | + | Φ | + | Φ | + | Φ |
| 40 | 2 |  |  |  |  |  | Φ | (+) | Φ | + | Φ |
| 41 | 4 |  |  |  |  |  |  |  |  |  |  |

TABLE 10

Summary of the affinity and inhibin peptide specificity of the Mabs from Table 7, 8 and 9. Biotinylated peptides Set 1 and Set 2 are included for ease of comparison with the data in the provisional patent. A comparison with Groome R1 and #1989 antibodies is also presented.

| Mab | Affinity for inhibin (ED25, nmoles/L) | Epitope region (Peptide Set 2) | Epitope region (Peptide Set 1) | Epitope designation |
|---|---|---|---|---|
| PO#6 | not tested, low | 2-7 | 3-6 | #5 |
| PO#22 | not tested, low | 2-7 | 3-6 | #5 |
| Groome R1 | 1.6 | 2-7 | 3-6 | |
| PO#12 | 37 | 22-27 | 21-23 | |
| PO#14 | 14.8 | 22-27 | 21-23 | |
| PO#9 | low affinity | 35-40 | 30-32 | #30 |
| PO#19 | 12 | 35-40 | 30-32 | #30 |
| PO#23 | 5.5 | 35-40 | 30-32 | #30 |
| PO#25 | 9.4 | 35-40 | 30-32 | #30 |
| PO#26 | low affinity | 35-40 | 30-32 | #30 |
| #1989 | 0.19 | 35 | 30 | |

TABLE 11

Characteristics of the inhibin alpha ELISAs

| Coating Antibody | Labeled antibody | working range (pg/well) | Assay sensitivity (pg/well) | Between assay variation |
|---|---|---|---|---|
| PO#14 | R1 | 1.5-100 | 1.5 | 19% (n = 7) |
| PO#23 | R1 | 0.8-100 | 0.8 | 8.3% (n = 7) |
| PO#14 + PO#23 | R1 | 0.6-100 | 0.6 | 7.3% (n = 7) |

TABLE 12

Specificity of the inhibin alpha using MAb combinations PO#14-R1, PO#23-R1 and PO#14 + PO#23-R1. Data is presented in relation to the recombinant human (rh) inhibin A standard (=100) Average of two experiments.

| Preparation | 14-R1 ELISA | 23-R1 ELSIA | 14 + 23-R1 ELISA |
|---|---|---|---|
| rh-inhibin AWHO 91/624 | 100 | 100 | 100 |
| rh-inhibin BR&D systems | 320 | 253 | 138 |
| Pro-(alpha)COB standard* | 98.5 | 41.5 | 38.5 |
| rh-activin APHIMR preparation | <0.2 | <0.2 | <0.2 |

*preparation provided as standard in Pro-(alpha)C ELISA by Oxford Bio-innovations Ltd, UK.

TABLE 13

Levels of inhibin in human serum and human follicular fluid using the inhibin alpha ELISAs

| | Inhibin concentration (pg/mL) | | |
|---|---|---|---|
| | 14-R1 ELISA | 23-R1 ELISA | 14 + 23-R1 ELISA |
| postmenopausal serum | <1.5 | <1.5 | <1.5 |
| female serum pool 1 | 14 | 28 | 22 |
| female serum pool 2 | 44 | 98 | 77 |
| female serum pool 3 | 228 | 292 | 237 |
| male serum | 100 | 64 | 46 |
| human follicular fluid | 60800 | 58800 | 46000 |

The three female pools were prepared from serum collected as part of an in vitro fertilization program and combined into the 3 pools based on their serum estradiol levels (pool 1<1 nmoles/L, pool 2<2 nmoles/L, pool 3>2 nmoles/L)

TABLE 14

Serum inhibin levels determined by various inhibin alpha assays in normal postmenopausal women and postmenopausal women with ovarian cancers. Values are presented as geometric mean ± 2SD

| | n | RIA (mU/mL) | IFMA (pg/mL) | 14-R1 ELISA (pg/mL) | 23-R1 ELISA (pg/mL) | 14 + 23-R1 ELISA (pg/mL) |
|---|---|---|---|---|---|---|
| Normal | 61 | <122 | 51.0 | 1.57 | 0.88 | 0.72 |
| | | | 15.8-164.7 | 0.71-3.49 | 0.39-1.97 | 0.23-2.32 |
| GCT | 7 | 1918 | 4320 | 113 | 229 | 165 |
| | | 109-33800 | 187-99700 | 1.15-11000 | 2.19-23400 | 1.68-16300 |
| Mucinous | 8 | 319 | 1020 | 15.6 | 15.1 | 20.9 |
| | | 22.5-4504 | 144-7286 | 0.45-535 | 0.39-583 | 0.91-477 |
| Serous | 15 | 116 | 112 | 1.83 | 1.44 | 0.97 |
| | | 44.1-305.5 | 15.1-833 | 0.45-7.46 | 0.22-9.66 | 0.10-9.54 |
| Endometrioid | 8 | 114 | 154 | 2.11 | 1.83 | 4.86 |
| | | 21-619 | 15.5-1520 | 0.24-18.7 | 0.16-21.5 | 0.40-59.1 |
| Undifferentiated | 8 | 83.4 | 74.7 | 1.4* | 1.08 | 1.08 |
| Clear cell | | 44.6-156 | 9.6-581 | | 0.44-2.65 | 0.35-3.32 | n—number of women

*below sensitivity of assay

TABLE 15

Discrimination between ovarian cancer and control groups using a variety of serum inhibin alpha assays based on the number of values detected above the upper 2SD of the control values

|  | RIA | IFMA | 14-R1 ELISA | 23-R1 ELISA | 14 + 23-R1 ELISA |
|---|---|---|---|---|---|
| Level of discrimination | 122 mU/mL* | 165 pg/mL | 3.49 pg/mL | 1.98 pg/mL | 2.33 pg/mL |
| Normal |  | 2/61 | 5/61 | 3/61 | 5/61 |
| GCT | 7/7 | 7/7 | 7/7 | 7/7 | 7/7 |
| Mucinous | 5/8 | 7/8 | 7/8 | 6/8 | 7/8 |
| Serous | 5/15 | 4/15 | 3/15 | 5/15 | 5/15 |
| Endometrioid | 3/8 | 3/8 | 1/8 | 4/8 | 3/8 |
| Undifferentiated |  |  |  |  |  |
| Clear cell | 1/8 | 1/8 | 0/8 | 1/8 | 0/8 |

*Discrimination value for RIA determined previously (Healy et al 1993)

TABLE 16

Correlation coefficients for comparisons between serum inhibin levels determined by the various assays

| X axis | Y axis | Correlation coefficient (r) | number of cases |
|---|---|---|---|
| RIA | IFMA | 0.824 | 46 |
| IFMA | 14-R1 ELISA | 0.902 | 46 |
| IFMA | 23-R1 ELISA | 0.906 | 46 |
| IFMA | 14 + 23-R1 ELISA | 0.934 | 46 |
| 14-R1 ELISA | 23-R1 ELISA | 0.946 | 46 |
| RIA | 14 + 23-R1 ELISA | 0.852 | 46 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

---

We claim:

1. An ovarian cancer diagnosis kit comprising a first isolated antigen-binding molecule and a second isolated antigen-binding molecule, wherein the first isolated antigen-binding molecule binds specifically to a first immuno-interactive sequence contained within a first region of an (alpha)C portion of a mammalian inhibin alpha subunit, wherein the first region consists of an amino acid sequence selected from residues 3-26 or 109-132 of SEQ ID NO:2, wherein the second isolated antigen-binding molecule binds specifically to a second immuno-interactive sequence contained within a second region of the (alpha)C portion of the mammalian inhibin alpha subunit, wherein the second region consists of an amino acid sequence selected from residues 73-96 of SEQ ID NO:2, and wherein at least one of the first and second antigen-binding molecules is other than a polyclonal antibody.

2. The kit of claim 1, wherein the first immuno-interactive sequence consists of the amino acid sequence selected from SEQ ID NOs:35-40 and wherein the second immuno-interactive sequence consists of an amino acid sequence selected from SEQ ID NOs:55-60.

3. The kit of claim 1, wherein the first immuno-interactive sequence consists of the amino acid sequence selected from SEQ ID NOs:68-73 and wherein the second immuno-interactive sequence consists of an amino acid sequence selected from SEQ ID NOs:55-60.

4. The kit of claim 1, wherein the first and second isolated antigen-binding molecules are monoclonal antibodies.

5. The kit of claim 1, wherein the mammalian inhibin is human inhibin.

6. An ovarian cancer diagnosis kit comprising a first isolated antigen-binding molecule, a second isolated antigen-binding molecule and a third isolated antigen-binding molecule, wherein the first isolated antigen-binding molecule binds specifically to a first immuno-interactive sequence contained within a first region of an (alpha)C portion of a mammalian inhibin alpha subunit, wherein the first region consists of residues 73-96 of SEQ ID NO:2, wherein the second isolated antigen-binding molecule binds specifically to a second immuno-interactive sequence contained within a second region of the (alpha)C portion of the mammalian inhibin alpha subunit, wherein the second region consists of residues 109-132 of SEQ ID NO:2, and wherein the third isolated antigen-binding molecule binds specifically to a third immuno-interactive sequence contained within a third region of the (alpha)C portion of the mammalian inhibin alpha subunit, wherein the third region consists of residues 3-26 of SEQ ID NO:2, and wherein at least one of the first, second and third isolated antigen-binding molecules is other than a polyclonal antibody.

7. The kit of claim 6, wherein the first immuno-interactive sequence consists of an amino acid sequence selected from SEQ ID NOs:55-60, wherein the second immuno-interactive sequence consists of the amino acid sequence selected from SEQ ID NOs:68-73 and wherein the third immuno-interactive sequence consists of an amino acid sequence selected from SEQ ID NOs:35-40.

8. The kit of claim 6, wherein the first and second isolated antigen-binding molecules are adapted for use as capture antibodies and the third isolated antigen-binding molecule is associated with a reporter molecule.

9. An ovarian cancer diagnosis kit comprising a first isolated antigen-binding molecule, a second isolated antigen-binding molecule and a third isolated antigen-binding molecule, wherein the first isolated antigen-binding molecule binds specifically to an immuno-interactive sequence contained within a first region of an (alpha)C portion of the mammalian inhibin, wherein the first region consists of an amino acid sequence selected from residues 3-26, or 109-132 of SEQ ID NO:2, wherein the second isolated antigen-binding molecule binds specifically to a second immuno-interactive sequence contained within a second region of the (alpha)C portion of the mammalian inhibin alpha subunit, wherein the second region consists of an amino acid sequence selected from residues 73-96 of SEQ ID NO:2, wherein the first isolated antigen-binding molecule binds to a different region than the second isolated antigen-binding molecule and wherein at least one of the first and second isolated antigen-binding molecules is other than a polyclonal antibody, and wherein the third isolated antigen-binding molecule binds specifically to another antigen that is aberrantly expressed in ovarian cancer.

10. The kit of claim 9, wherein the first immuno-interactive sequence consists of an amino acid sequence selected from SEQ ID NOs:35-40 and wherein the second immuno-interactive sequence consists of an amino acid sequence selected from SEQ ID NOs:55-60.

11. The kit of claim 9, wherein the first isolated antigen binding molecule binds specifically to an immuno-interactive sequence that consists of the amino acid sequence selected from SEQ ID NOs:68-73 and wherein the second immuno-interactive sequence consists of an amino acid sequence selected from SEQ ID NOs:55-60.

12. The kit of claim 9, wherein the other antigen is ovarian cancer antigen CA125.

* * * * *

SEQUENCE LISTING

<160> NUMBER OF SEQ ID NOS: 77

<210> SEQ ID NO 1
<211> LENGTH: 405
<212> TYPE: DNA
<213> ORGANISM: Artificial Sequence
<220> FEATURE:
<223> OTHER INFORMATION: alpha C fragment of human inhibin
<220> FEATURE:
<221> NAME/KEY: CDS
<222> LOCATION: (1)..(405)
<223> OTHER INFORMATION:

<400> SEQUENCE: 1

```
tca act ccc ctg atg tcc tgg cct tgg tct ccc tct gct ctg cgc ctg      48
Ser Thr Pro Leu Met Ser Trp Pro Trp Ser Pro Ser Ala Leu Arg Leu
1               5                   10                  15 ctg cag agg cct ccg gag gaa ccg gct gcc cat gcc aac tgc cac aga      96
Leu Gln Arg Pro Pro Glu Glu Pro Ala Ala His Ala Asn Cys His Arg
            20                  25                  30 gta gca ctg aac atc tcc ttc cag gag ctg ggc tgg gaa cgg tgg atc     144
Val Ala Leu Asn Ile Ser Phe Gln Glu Leu Gly Trp Glu Arg Trp Ile
        35                  40                  45 gtg tac cct ccc agt ttc atc ttc cac tac tgt cat ggt ggt tgt ggg     192
Val Tyr Pro Pro Ser Phe Ile Phe His Tyr Cys His Gly Gly Cys Gly
    50                  55                  60 ctg cac atc cca cca aac ctg tcc ctt cca gtc cct ggg gct ccc cct     240
Leu His Ile Pro Pro Asn Leu Ser Leu Pro Val Pro Gly Ala Pro Pro
65                  70                  75                  80 acc cca gcc cag ccc tac tcc ttg ctg cca ggg gcc cag ccc tgc tgt     288
Thr Pro Ala Gln Pro Tyr Ser Leu Leu Pro Gly Ala Gln Pro Cys Cys
                85                  90                  95 gct gct ctc cca ggg acc atg agg ccc cta cat gtc cgc acc acc tcg     336
```

```
Ala Ala Leu Pro Gly Thr Met Arg Pro Leu His Val Arg Thr Thr Ser
            100                 105                 110 gat gga ggt tac tct ttc aag tat gag aca gtg ccc aac ctt ctc acg      384
Asp Gly Gly Tyr Ser Phe Lys Tyr Glu Thr Val Pro Asn Leu Leu Thr
            115                 120                 125 cag cac tgt gct tgt atc taa                                          405
Gln His Cys Ala Cys Ile
        130

<210> SEQ ID NO 2
<211> LENGTH: 134
<212> TYPE: PRT
<213> ORGANISM: Artificial Sequence
<220> FEATURE:
<223> OTHER INFORMATION: alpha C fragment of human inhibin

<400> SEQUENCE: 2

Ser Thr Pro Leu Met Ser Trp Pro Trp Ser Pro Ser Ala Leu Arg Leu
1               5                   10                  15

Leu Gln Arg Pro Pro Glu Glu Pro Ala Ala His Ala Asn Cys His Arg
            20                  25                  30

Val Ala Leu Asn Ile Ser Phe Gln Glu Leu Gly Trp Glu Arg Trp Ile
        35                  40                  45

Val Tyr Pro Pro Ser Phe Ile Phe His Tyr Cys His Gly Gly Cys Gly
    50                  55                  60

Leu His Ile Pro Pro Asn Leu Ser Leu Pro Val Pro Gly Ala Pro Pro
65                  70                  75                  80

Thr Pro Ala Gln Pro Tyr Ser Leu Leu Pro Gly Ala Gln Pro Cys Cys
                85                  90                  95

Ala Ala Leu Pro Gly Thr Met Arg Pro Leu His Val Arg Thr Thr Ser
            100                 105                 110

Asp Gly Gly Tyr Ser Phe Lys Tyr Glu Thr Val Pro Asn Leu Leu Thr
            115                 120                 125

Gln His Cys Ala Cys Ile
        130

<210> SEQ ID NO 3
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 3 of TABLE 1

<400> SEQUENCE: 3

Ser Thr Pro Leu Met Ser Trp Pro Trp Ser Pro Ser Ala Leu
1               5                   10

<210> SEQ ID NO 4
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 4 of TABLE 1

<400> SEQUENCE: 4

Met Ser Trp Pro Trp Ser Pro Ser Ala Leu Arg Leu Leu Gln
1               5                   10

<210> SEQ ID NO 5
<211> LENGTH: 14
```

```
<212> TYPE: PRT
<213> ORGANISM: Artificial Sequence
<220> FEATURE:
<223> OTHER INFORMATION: inhibin alpha C amino acid sequence
      corresponding to peptide 5 of TABLE 1

<400> SEQUENCE: 5

Trp Ser Pro Ser Ala Leu Arg Leu Leu Gln Arg Pro Pro Glu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 6 of TABLE 1

<400> SEQUENCE: 6

Ala Leu Arg Leu Leu Gln Arg Pro Pro Glu Glu Pro Ala Ala
1               5                   10

<210> SEQ ID NO 7
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 7 of TABLE 1

<400> SEQUENCE: 7

Leu Gln Arg Pro Pro Glu Glu Pro Ala Ala His Ala Asn Cys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 8 of TABLE 1

<400> SEQUENCE: 8

Pro Glu Glu Pro Ala Ala His Ala Asn Cys His Arg Val Ala
1               5                   10

<210> SEQ ID NO 9
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 9 of TABLE 1

<400> SEQUENCE: 9

Ala Ala His Ala Asn Cys His Arg Val Ala Leu Asn Ile Ser
1               5                   10

<210> SEQ ID NO 10
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 10 o f TABLE 1

<400> SEQUENCE: 10

Asn Cys His Arg Val Ala Leu Asn Ile Ser Phe Gln Glu Leu
```

```
1               5                   10

<210> SEQ ID NO 11
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 11 o f TABLE 1

<400> SEQUENCE: 11

Val Ala Leu Asn Ile Ser Phe Gln Glu Leu Gly Trp Glu Arg
1               5                   10

<210> SEQ ID NO 12
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 12 o f TABLE 1

<400> SEQUENCE: 12

Ile Ser Phe Gln Glu Leu Gly Trp Glu Arg Trp Ile Val Tyr
1               5                   10

<210> SEQ ID NO 13
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 13 o f TABLE 1

<400> SEQUENCE: 13

Glu Leu Gly Trp Glu Arg Trp Ile Val Tyr Pro Pro Ser Phe
1               5                   10

<210> SEQ ID NO 14
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 14 o f TABLE 1

<400> SEQUENCE: 14

Glu Arg Trp Ile Val Tyr Pro Pro Ser Phe Ile Phe His Tyr
1               5                   10

<210> SEQ ID NO 15
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 15 o f TABLE 1

<400> SEQUENCE: 15

Val Tyr Pro Pro Ser Phe Ile Phe His Tyr Cys His Gly Gly
1               5                   10

<210> SEQ ID NO 16
<211> LENGTH: 14
<212> TYPE: PRT
<213> ORGANISM: Artificial Sequence
<220> FEATURE:
<223> OTHER INFORMATION: inhibin alpha C amino acid sequence
``` corresponding to peptide 16 of TABLE 1

<400> SEQUENCE: 16

Ser Phe Ile Phe His Tyr Cys His Gly Gly Cys Gly Leu His
1               5                   10

<210> SEQ ID NO 17
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 17 of TABLE 1

<400> SEQUENCE: 17

His Tyr Cys His Gly Gly Cys Gly Leu His Ile Pro Pro Asn
1               5                   10

<210> SEQ ID NO 18
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 18 of TABLE 1

<400> SEQUENCE: 18

Gly Gly Cys Gly Leu His Ile Pro Pro Asn Leu Ser Leu Pro
1               5                   10

<210> SEQ ID NO 19
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 19 of TABLE 1

<400> SEQUENCE: 19

Leu His Ile Pro Pro Asn Leu Ser Leu Pro Val Pro Gly Ala
1               5                   10

<210> SEQ ID NO 20
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 20 of TABLE 1

<400> SEQUENCE: 20

Pro Asn Leu Ser Leu Pro Val Pro Gly Ala Pro Pro Thr Pro
1               5                   10

<210> SEQ ID NO 21
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 21 of TABLE 1

<400> SEQUENCE: 21

Leu Pro Val Pro Gly Ala Pro Pro Thr Pro Ala Gln Pro Tyr
1               5                   10

<210> SEQ ID NO 22

-continued

```
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 22 o f TABLE 1

<400> SEQUENCE: 22

Gly Ala Pro Pro Thr Pro Ala Gln Pro Tyr Ser Leu Leu Pro
1               5                   10

<210> SEQ ID NO 23
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 23 o f TABLE 1

<400> SEQUENCE: 23

Thr Pro Ala Gln Pro Tyr Ser Leu Leu Pro Gly Ala Gln Pro
1               5                   10

<210> SEQ ID NO 24
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 24 o f TABLE 1

<400> SEQUENCE: 24

Pro Tyr Ser Leu Leu Pro Gly Ala Gln Pro Cys Cys Ala Ala
1               5                   10

<210> SEQ ID NO 25
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 25 o f TABLE 1

<400> SEQUENCE: 25

Leu Pro Gly Ala Gln Pro Cys Cys Ala Ala Leu Pro Gly Thr
1               5                   10

<210> SEQ ID NO 26
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 26 o f TABLE 1

<400> SEQUENCE: 26

Gln Pro Cys Cys Ala Ala Leu Pro Gly Thr Met Arg Pro Leu
1               5                   10

<210> SEQ ID NO 27
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 27 o f TABLE 1

<400> SEQUENCE: 27
```

-continued

```
Ala Ala Leu Pro Gly Thr Met Arg Pro Leu His Val Arg Thr
1               5                   10

<210> SEQ ID NO 28
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 28 o f TABLE 1

<400> SEQUENCE: 28

Gly Thr Met Arg Pro Leu His Val Arg Thr Thr Ser Asp Gly
1               5                   10

<210> SEQ ID NO 29
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 29 o f TABLE 1

<400> SEQUENCE: 29

Pro Leu His Val Arg Thr Thr Ser Asp Gly Gly Tyr Ser Phe
1               5                   10

<210> SEQ ID NO 30
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 30 o f TABLE 1

<400> SEQUENCE: 30

Arg Thr Thr Ser Asp Gly Gly Tyr Ser Phe Lys Tyr Glu Thr
1               5                   10

<210> SEQ ID NO 31
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 31 o f TABLE 1

<400> SEQUENCE: 31

Asp Gly Gly Tyr Ser Phe Lys Tyr Glu Thr Val Pro Asn Leu
1               5                   10

<210> SEQ ID NO 32
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 32 o f TABLE 1

<400> SEQUENCE: 32

Ser Phe Lys Tyr Glu Thr Val Pro Asn Leu Leu Thr Gln His
1               5                   10

<210> SEQ ID NO 33
<211> LENGTH: 14
<212> TYPE: PRT
<213> ORGANISM: Artificial Sequence
<220> FEATURE:
```

```
<223> OTHER INFORMATION: inhibin alpha C amino acid sequence
      corresponding to peptide 33 o f TABLE 1

<400> SEQUENCE: 33

Glu Thr Val Pro Asn Leu Leu Thr Gln His Cys Ala Cys Ile
1               5                   10

<210> SEQ ID NO 34
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 1 of TABLE 7

<400> SEQUENCE: 34

Ser Thr Pro Leu Met Ser Trp Pro Trp Ser Pro Ser Ala Leu
1               5                   10

<210> SEQ ID NO 35
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 2 of TABLE 7

<400> SEQUENCE: 35

Pro Leu Met Ser Trp Pro Trp Ser Pro Ser Ala Leu Arg Leu
1               5                   10

<210> SEQ ID NO 36
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 3 of TABLE 7

<400> SEQUENCE: 36

Met Ser Trp Pro Trp Ser Pro Ser Ala Leu Arg Leu Leu Gln
1               5                   10

<210> SEQ ID NO 37
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 4 of TABLE 7

<400> SEQUENCE: 37

Met Pro Trp Ser Pro Ser Ala Leu Arg Leu Leu Gln Arg Pro
1               5                   10

<210> SEQ ID NO 38
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 5 of TABLE 7

<400> SEQUENCE: 38

Trp Ser Pro Ser Ala Leu Arg Leu Leu Gln Arg Pro Pro Glu
1               5                   10
```

<210> SEQ ID NO 39
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 6 of TABLE 7

<400> SEQUENCE: 39

Pro Ser Ala Leu Arg Leu Leu Gln Arg Pro Pro Glu Glu Pro
1               5                   10

<210> SEQ ID NO 40
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 7 of TABLE 7

<400> SEQUENCE: 40

Ala Leu Arg Leu Leu Gln Arg Pro Pro Glu Glu Pro Ala Ala
1               5                   10

<210> SEQ ID NO 41
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 8 of TABLE 7

<400> SEQUENCE: 41

Leu Gln Arg Pro Pro Glu Glu Pro Ala Ala His Ala Asn Cys
1               5                   10

<210> SEQ ID NO 42
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 9 of TABLE 7

<400> SEQUENCE: 42

Pro Glu Glu Pro Ala Ala His Ala Asn Cys His Arg Val Ala
1               5                   10

<210> SEQ ID NO 43
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 10 o f TABLE 7

<400> SEQUENCE: 43

Ala Ala His Ala Asn Cys His Arg Val Ala Leu Asn Ile Ser
1               5                   10

<210> SEQ ID NO 44
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 11 o f TABLE 7

<400> SEQUENCE: 44

-continued

```
Asn Cys His Arg Val Ala Leu Asn Ile Ser Phe Gln Glu Leu
1               5                   10

<210> SEQ ID NO 45
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 12 o f TABLE 7

<400> SEQUENCE: 45

Val Ala Leu Asn Ile Ser Phe Gln Glu Leu Gly Trp Glu Arg
1               5                   10

<210> SEQ ID NO 46
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 13 o f TABLE 7

<400> SEQUENCE: 46

Ile Ser Phe Gln Glu Leu Gly Trp Glu Arg Trp Ile Val Tyr
1               5                   10

<210> SEQ ID NO 47
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 14 o f TABLE 7

<400> SEQUENCE: 47

Glu Leu Gly Trp Glu Arg Trp Ile Val Tyr Pro Pro Ser Phe
1               5                   10

<210> SEQ ID NO 48
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 15 o f TABLE 7

<400> SEQUENCE: 48

Glu Arg Trp Ile Val Tyr Pro Pro Ser Phe Ile Phe His Tyr
1               5                   10

<210> SEQ ID NO 49
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 16 o f TABLE 7

<400> SEQUENCE: 49

Val Tyr Pro Pro Ser Phe Ile Phe His Tyr Cys His Gly Gly
1               5                   10

<210> SEQ ID NO 50
<211> LENGTH: 14
<212> TYPE: PRT
<213> ORGANISM: Artificial Sequence
```

```
<220> FEATURE:
<223> OTHER INFORMATION: inhibin alpha C amino acid sequence
      corresponding to peptide 17 o f TABLE 7

<400> SEQUENCE: 50

Ser Phe Ile Phe His Tyr Cys His Gly Gly Cys Gly Leu His
1               5                   10

<210> SEQ ID NO 51
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 18 o f TABLE 7

<400> SEQUENCE: 51

His Tyr Cys His Gly Gly Cys Gly Leu His Ile Pro Pro Asn
1               5                   10

<210> SEQ ID NO 52
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 19 o f TABLE 7

<400> SEQUENCE: 52

Gly Gly Cys Gly Leu His Ile Pro Pro Asn Leu Ser Leu Pro
1               5                   10

<210> SEQ ID NO 53
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 20 o f TABLE 7

<400> SEQUENCE: 53

Leu His Ile Pro Pro Asn Leu Ser Leu Pro Val Pro Gly Ala
1               5                   10

<210> SEQ ID NO 54
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 21 o f TABLE 7

<400> SEQUENCE: 54

Pro Asn Leu Ser Leu Pro Val Pro Gly Ala Pro Pro Thr Pro
1               5                   10

<210> SEQ ID NO 55
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 22 o f TABLE 7

<400> SEQUENCE: 55

Leu Pro Val Pro Gly Ala Pro Pro Thr Pro Ala Gln Pro Tyr
1               5                   10
```

<210> SEQ ID NO 56
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 23 o f TABLE 7

<400> SEQUENCE: 56

Val Pro Gly Ala Pro Pro Thr Pro Ala Gln Pro Tyr Ser Leu
1               5                   10

<210> SEQ ID NO 57
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 24 o f TABLE 7

<400> SEQUENCE: 57

Gly Ala Pro Pro Thr Pro Ala Gln Pro Tyr Ser Leu Leu Pro
1               5                   10

<210> SEQ ID NO 58
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 25 o f TABLE 7

<400> SEQUENCE: 58

Pro Pro Thr Pro Ala Gln Pro Tyr Ser Leu Leu Pro Gly Ala
1               5                   10

<210> SEQ ID NO 59
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 26 o f TABLE 7

<400> SEQUENCE: 59

Thr Pro Ala Gln Pro Tyr Ser Leu Leu Pro Gly Ala Gln Pro
1               5                   10

<210> SEQ ID NO 60
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 27 o f TABLE 7

<400> SEQUENCE: 60

Ala Gln Pro Tyr Ser Leu Leu Pro Gly Ala Gln Pro Cys Cys
1               5                   10

<210> SEQ ID NO 61
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 28 o f TABLE 7

-continued

```
<400> SEQUENCE: 61

Pro Tyr Ser Leu Leu Pro Gly Ala Gln Pro Cys Cys Ala Ala
1               5                   10

<210> SEQ ID NO 62
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 29 o f TABLE 7

<400> SEQUENCE: 62

Ser Leu Leu Pro Gly Ala Gln Pro Cys Cys Ala Ala Leu Pro
1               5                   10

<210> SEQ ID NO 63
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 30 o f TABLE 7

<400> SEQUENCE: 63

Leu Pro Gly Ala Gln Pro Cys Cys Ala Ala Leu Pro Gly Thr
1               5                   10

<210> SEQ ID NO 64
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 31 o f TABLE 7

<400> SEQUENCE: 64

Gln Pro Cys Cys Ala Ala Leu Pro Gly Thr Met Arg Pro Leu
1               5                   10

<210> SEQ ID NO 65
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 32 o f TABLE 7

<400> SEQUENCE: 65

Ala Ala Leu Pro Gly Thr Met Arg Pro Leu His Val Arg Thr
1               5                   10

<210> SEQ ID NO 66
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 33 o f TABLE 7

<400> SEQUENCE: 66

Gly Thr Met Arg Pro Leu His Val Arg Thr Thr Ser Asp Gly
1               5                   10

<210> SEQ ID NO 67
<211> LENGTH: 14
<212> TYPE: PRT
```

-continued

```
<213> ORGANISM: Artificial Sequence
<220> FEATURE:
<223> OTHER INFORMATION: inhibin alpha C amino acid sequence
      corresponding to peptide 34 of TABLE 7

<400> SEQUENCE: 67

Pro Leu His Val Arg Thr Thr Ser Asp Gly Gly Tyr Ser Phe
1               5                   10

<210> SEQ ID NO 68
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 35 of TABLE 7

<400> SEQUENCE: 68

Arg Thr Thr Ser Asp Gly Gly Tyr Ser Phe Lys Tyr Glu Thr
1               5                   10

<210> SEQ ID NO 69
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 36 of TABLE 7

<400> SEQUENCE: 69

Thr Ser Asp Gly Gly Tyr Ser Phe Lys Tyr Glu Thr Val Pro
1               5                   10

<210> SEQ ID NO 70
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 37 of TABLE 7

<400> SEQUENCE: 70

Asp Gly Gly Tyr Ser Phe Lys Tyr Glu Thr Val Pro Asn Leu
1               5                   10

<210> SEQ ID NO 71
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 38 of TABLE 7

<400> SEQUENCE: 71

Gly Tyr Ser Phe Lys Tyr Glu Thr Val Pro Asn Leu Leu Thr
1               5                   10

<210> SEQ ID NO 72
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 39 of TABLE 7

<400> SEQUENCE: 72

Ser Phe Lys Tyr Glu Thr Val Pro Asn Leu Leu Thr Gln His
1               5                   10
```

```
<210> SEQ ID NO 73
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 40 o f TABLE 7

<400> SEQUENCE: 73

Lys Tyr Glu Thr Val Pro Asn Leu Leu Thr Gln His Cys Ala
1               5                   10

<210> SEQ ID NO 74
<211> LENGTH: 14
<212> TYPE: PRT
<213> ORGANISM: Artificial Sequence
<220> FEATURE:
<223> OTHER INFORMATION: inhibin alpha C amino acid sequence
      corresponding to peptide 41 o f TABLE 7

<400> SEQUENCE: 74

Glu Thr Val Pro Asn Leu Leu Thr Gln His Cys Ala Cys Ile
1               5                   10

<210> SEQ ID NO 75
<211> LENGTH:
<212> TYPE:
<213> ORGANISM:

<400> SEQUENCE: 75

000

<210> SEQ ID NO 76
<211> LENGTH: 4
<212> TYPE: PRT
<213> ORGANISM: Artificial Sequence
<220> FEATURE:
<223> OTHER INFORMATION: Linker Sequence

<400> SEQUENCE: 76

Ser Gly Ser Gly
1

<210> SEQ ID NO 77
<211> LENGTH: 4
<212> TYPE: PRT
<213> ORGANISM: Artificial Sequence
<220> FEATURE:
<223> OTHER INFORMATION: linker sequence

<400> SEQUENCE: 77

Ser Gly Ser Gly
1
```